US011471532B2

(12) United States Patent
Javaheri et al.

(10) Patent No.: US 11,471,532 B2
(45) Date of Patent: Oct. 18, 2022

(54) **METHODS FOR TREATMENT OF *H. PYLORI* INFECTIONS**

(71) Applicants: TECHNISCHE UNIVERSITÄT MÜNCHEN, Munich (DE); MAX-PLANCK-GESELLSCHAFT ZUR FÖRDERUNG DER WISSENSCHAFTEN E.V., Munich (DE)

(72) Inventors: Anahita Javaheri, Munich (DE); Tobias Kruse, Munich (DE); Markus Gerhard, Munich (DE); Bernhard B. Singer, Essen (DE); Daniel Hornburg, Munich (DE); Han Remaut, Vertrijk (BE); Matthias Mann, Munich (DE); Felix Meissner, Gauting (DE); Steffen Backert, Erlangen (DE)

(73) Assignees: MAX-PLANCK-GESELLSCHAFT ZUR FÖRDERUNG, Munich (DE); DER WISSENSCHAFT EN E.V., Munich (DE); TECHNISCHE UNIVERSITÄT MÜNCHEN, Munich (DE)

( * ) Notice: Subject to any disclaimer, the term of this patent is extended or adjusted under 35 U.S.C. 154(b) by 355 days.

(21) Appl. No.: 16/317,753

(22) PCT Filed: Jul. 20, 2017

(86) PCT No.: PCT/EP2017/068297

§ 371 (c)(1), (2) Date: Jan. 14, 2019

(87) PCT Pub. No.: WO2018/015468

PCT Pub. Date: Jan. 25, 2018

(65) Prior Publication Data

US 2021/0008207 A1 Jan. 14, 2021

(30) Foreign Application Priority Data

Jul. 20, 2016 (EP) .................................... 16180430

(51) Int. Cl.
*A61K 38/00* (2006.01)
*A61K 45/06* (2006.01)

(52) U.S. Cl.
CPC .............. *A61K 45/06* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,025,164 | A | 2/2000 | Bolin et al. |
| 6,372,260 | B1 | 4/2002 | Andersson et al. |
| 6,576,244 | B1 | 6/2003 | Weltzin et al. |
| 6,838,089 | B1 | 1/2005 | Carlsson et al. |
| 2002/0151462 | A1 | 10/2002 | Lissolo |
| 2004/0033240 | A1 | 2/2004 | Guy et al. |
| 2005/0063987 | A1 | 3/2005 | Knapp et al. |
| 2005/0175629 | A1 | 8/2005 | Del Giudice |
| 2006/0193866 | A1 | 8/2006 | Meinke et al. |
| 2007/0026018 | A1 | 2/2007 | Ellis et al. |
| 2007/0042448 | A1 | 2/2007 | Boneca et al. |

FOREIGN PATENT DOCUMENTS

| | | | |
|---|---|---|---|
| EP | 1508572 | A4 | 8/2006 |
| EP | 2082750 | A1 | 7/2009 |
| WO | WO 2001/083531 | A1 | 11/2001 |
| WO | WO 2001/083533 | A1 | 11/2001 |
| WO | WO 2002/002141 | A2 | 1/2002 |
| WO | WO 2002/066501 | A2 | 8/2002 |
| WO | WO 2004/094467 | A2 | 11/2004 |
| WO | WO 2008/046650 | A1 | 4/2008 |
| WO | WO 2010/050903 | A1 | 5/2010 |
| WO | WO 2011/018779 | A1 | 2/2011 |
| WO | WO 2011/081598 | A1 | 7/2011 |
| WO | WO 2012/031530 | A1 | 3/2012 |
| WO | WO 2013/164652 | A2 | 11/2013 |

OTHER PUBLICATIONS

Zhang et al. "CEACAM6 promotes tumor migration, invasion, and metastasis in gastric cancer". Acta Biochim Biophys Sin 2014, 46: 283-290. (Year: 2014).*

Oxford English Dictionary, "ligand", definition "b." from 1997 Draft Addition, accessed May 17, 2021 from www.oed.com/view/Entry/108156 (Year: 1997).*

Holsten, L. "Characterization of new adhesion receptors of Helicobacter pylori and its role in translocation of the cytotoxin CagA", dissertation, Ludwig Maximilians University in Munich, 2015 (Machine translation of German original titled "Charakterisierung neuer Adhäsinrezeptoren von Helicobact . . . ") (Year: 2015).*

Testerman et al. Helicobacter pylori: Physiology and Genetics. Chapter 34, "Adherence and Colonization"; Washington (DC) ASM Press; 2001 (online version accessed on May 14, 2021 from www.ncbi.nlm.nih.gov/books/NBK2437/?report=printable) (Year: 2001).*

Sela-Culang et al in "The structural basis of antibody-antigen recognition"; Frontiers in Immunology, vol. 4, Article 302, Oct. 2013. (Year: 2013).*

(Continued)

*Primary Examiner* — Elly-Gerald Stoica
(74) *Attorney, Agent, or Firm* — Leydig, Voit & Mayer, Ltd.

(57) ABSTRACT

The present invention relates to inhibitors of the interaction between *H. pylori* HopQ and a member of the carcinoembryonic antigen-related cell adhesion molecule (CEACAM) family as well as to immunogenic compositions based on *H. pylori* HopQ. The present invention further relates to the use of the inhibitors and immunogenic compositions for preventing or treating a disease or disorder caused by or associated with *H. pylori.*

6 Claims, 27 Drawing Sheets

Specification includes a Sequence Listing.

(56) References Cited

OTHER PUBLICATIONS

International Search Report and Written Opinion, PCT/EP2017/068297, dated Oct. 27, 2017, 16 pages.
Lea Charlotte Holsten: "Charakterisierung: neuer Adhasinrezeptoren von Helicobacter pylori und deren Rolle bei der Translokation des Cytotoxins CagA," Dissertation, Jul. 7, 2015, 148 pages.
Verena Koeniger: 11 CEACAMs as novel receptors for Helicobacter pylori outer membrane protein HopQ, Dissertation, Nov. 2, 2015, 144 pages.
Koeniger et al., "Helicobacter pylori exploits human CEACAMs via HopQ for adherence and translocation of CagA," Nature Microbiology 2(16188):1-12, Oct. 17, 2016.
Javaheri et al., "Helicobacter pylori adhesin HopQ engages in a virulence-enhancing interaction with human CEACAMs," Nature Microbiology 2(16189):1-13, Oct. 17, 2016.
Database Medline, US National Library of Medicine (NLM), Bethesda, MD, US, 1996, Forman D: "Helicobacter pylori and gastric cancer," Database accession No. NLM8722403.
Apostolopoulos et al. (2013) "Targeting Antigens to Dendritic Cell Receptors for Vaccine Development," Journal of Drug Delivery 2013: 869718, pp. 1-22.
Belogolova et al. (2013) "Helicobacter pylori outer membrane protein HopQ identified as a novel T4SS-associated virulence factor," Cell Microbiol. 15(11):1896-1912.
Blaser et al. (1995) "Infection with Helicobacter pylori strains possessing cagA is associated with an increased risk of developing adenocarcinoma of the stomach," Cancer research 55(10):2111-2115.
Cao et al. (2002) "Two different families of hopQ alleles in Helicobacter pylori," Journal of Clinical Microbiology 40(12):4504-4511.
EP Office Action, dated Jul. 7, 2020, in European Patent Application No. 17 749 134.7, 8 pp.
Forman (1996) "Helicobacter pylori and gastric cancer," Scandinavian Journal of Gastroenterology Supplement 214:31-33, discussion 40-3 / Database accession No. NLM8722403.
Fox et al. (1998) "Hepatic *Helicobacter* species identified in bile and gallbladder tissue from Chileans with chronic cholecystitis," Gastroenterology 114(4):755-763.
Fox (2002) "The non-Helicobacter pylori helicobacters: their expanding role in gastrointestinal and systemic diseases," Gut 50:273-283.
Gao et al. (2010) "The evolution of Helicobacter pylori antibiotics resistance over 10 years in Beijing, China," Helicobacter 15(5):460-466.
Gómez-Gascón et al. (2012) "Exploring the pan-surfome of *Streptococcus suis*: Looking for common protein antigens," J Proteomics 75(18):5654-5666, Article in Press.
Graham et al. (2005) "The time to eradicate gastric cancer is now," Gut 54(6):735-738.
Hytönen et al. (2006) "Use of flow cytometry for the adhesion analysis of *Streptococcus pyogenes* mutant strains to epithelial cells: investigation of the possible role of surface pullulanase and cysteine protease, and the transcriptional regulator Rgg," BMC Microbiol. 6(18), doi:10.1186/1471-2180-6-18, 8 pp.
Jemal et al. (2011) "Global cancer statistics," CA: a cancer journal for clinicians 61(2):69-90.
Kalali et al. (2014) "H. pylori virulence factors: influence on immune system and pathology," Mediators of Inflammation 2014: 426309, 9 pp.
Koebnik et al. (2000) "Structure and function of bacterial outer membrane proteins: barrels in a nutshell," Molecular Microbiology 37(2):239-253.
Kwok et al. (2007) "Helicobacter exploits integrin for type IV secretion and kinase activation," Nature 449(7164):862-866.
Matsukura et al. (2002) "Association between Helicobacter bilis in bile and biliary tract malignancies: H. bilis in bile from Japanese and Thai patients with benign and malignant diseases in the biliary tract," Jpn J Cancer Res. 93(7):842-847.
Mori et al. (2012) "Chimeric flagellin as the self-adjucanting antigen for the activation of immune response against Helicobacter pylori," Vaccine 30(40):5856-5863.
Nomura et al. (1994) "Helicobacter pylori infection and the risk for duodenal and gastric ulceration," Annals of internal medicine 120(12):977-981.
Parsonnet et al. (1991) "Helicobacter pylori infection and the risk of gastric carcinoma," New England Journal of Medicine 325(16):1127-1131.
Perez-Perez et al. (2004) "Epidemology of Helicobacter pylori infection," Helicobacter 9(Supp. 1): 1-6.
Pisani et al. (2008) "Cross-Reactivity between Immune Responses to Helicobacter bilis and Helicobacter pylori in a Population in Thailand at High Risk of Developing Cholangiocarcinoma," Clin Vaccine Immunol. 15(9):1363-1368.
Shiota et al. (2010) "Population-based strategies for Helicobacter pylori-associated disease management: a Japanese perspective," Expert review of gastroenterology & hepatology 4(2):149-156.
Singer et al. (2014) "Soluble CEACAM8 interacts with CEACAM1 inhibiting TLR2-triggered immune responses," PLoS One 9(4): e94106, pp. 1-12.
Sioud et al. (2013) "A novel peptide carrier for efficient targeting of antigens and nucleic acids to dendritic cells," FASEB J. 27(8):3272-3283.
Song et al. (publicly available Jun. 2015) "A novel chimeric flagellum fused with the multi-epitope vaccine CTB-UE prevents Helicobacter pylori-induced gastric cancer in a BALB/c mouse model," Appl Microbiol Biotechnol. (Nov. 2015) 99(22):9495-9502.
Tchoupa et al. (2014) "Signaling by epithelial members of the CEACAM family—mucosal docking sites for pathogenic bacteria," Cell Commun Signal 12:27, 10 pp.
United States Centers for Disease Control and Prevention (2011) "A CDC framework for preventing infectious diseases," accessed Dec. 20, 2012, 33 pp.

* cited by examiner

| Stomach biopsies | No. of samples | No. Of CEACAM1 positive samples with staining score | | | |
|---|---|---|---|---|---|
| | | 0 | 1 | 2 | 3 |
| Normal | 10 | 8 | 2 | 1 | 0 |
| Gastritis | 10 | 3 | 3 | 3 | 1 | a

```
                               20                           40                        60
P13688 CEAM1_HUMAN N_Domain  QLTTESMPFN VAEGKEVLLL VHNLPQQLFG YSWYKGERVD GNRQIVGYAI GTQQATPGPA 60
 P16573 CEAM1_RAT N_Domain   --------.P. .V.ESS.... T.....EFQV FY....VTTTG L.SE.AR.IR SSNTSQTE.. 53
P31809 CEAM1_MOUSE N_Domain  EV.I.AV.PQ ...DNN.... ......LA.GA FA....NTTA IDKE.ARFVP NSNMNFT.Q. 60
                               80                          100
P13688 CEAM1_HUMAN N_Domain  NSGRETIYPN ASLLIQNVTQ NDTGFYTLQV IKSDLVNEEA TGQFHVYP 108
 P16573 CEAM1_RAT N_Domain   Y...V...S. G..FF...NK T.E.P...S. .DKQFNPIQT SV..R.-- 99
P31809 CEAM1_MOUSE N_Domain  Y....I..S. G...F.MI.M K.M.V...DM TDENYRRTQ. .VR...H. 108
``` b

Fig. 4

| Accession | Description | Score | Unique Peptides | PSMs | Area | AAs | MW [kDa] |
|---|---|---|---|---|---|---|---|
| B5Z8H1 | Outer membrane protein hopQ | 34.29 | 5 | 9 | 4.714E8 | 641 | 69.9 |
| B5Z6D0 | Outer membrane protein hopZ | 31.74 | 4 | 8 | 7.565E8 | 666 | 72.4 |
| B5Z783 | Outer membrane protein sabB | 23.37 | 5 | 7 | 8.180E8 | 638 | 70.7 |
| B5Z7R8 | Outer membrane protein hopC | 14.40 | 3 | 3 | 6.037E8 | 517 | 56.2 |
| B5ZA84 | Outer membrane protein babA | 8.0 | 1 | 2 | 4.238E8 | 744 | 80.8 |
| B5Z786 | Outer membrane protein sabA | 6.66 | 2 | 2 | 2.580E8 | 651 | 72.1 |

SEQUENCE LISTING

<160> NUMBER OF SEQ ID NOS: 33

<210> SEQ ID NO 1
<211> LENGTH: 641
<212> TYPE: PRT
<213> ORGANISM: Helicobacter pylori

<400> SEQUENCE: 1

```
Met Lys Lys Thr Lys Lys Thr Ile Leu Leu Ser Leu Thr Leu Ala Ala
1               5                   10                  15

Ser Leu Leu His Ala Glu Asp Asn Gly Val Phe Leu Ser Val Gly Tyr
            20                  25                  30

Gln Ile Gly Glu Ala Val Gln Lys Val Lys Asn Ala Asp Lys Val Gln
        35                  40                  45

Lys Leu Ser Asp Thr Tyr Glu Gln Leu Ser Arg Leu Leu Thr Asn Asp
    50                  55                  60

Asn Gly Thr Asn Ser Lys Thr Ser Ala Gln Ala Ile Asn Gln Ala Val
65                  70                  75                  80

Asn Asn Leu Asn Glu Arg Ala Lys Thr Leu Ala Gly Gly Thr Thr Asn
                85                  90                  95

Ser Pro Ala Tyr Gln Ala Thr Leu Leu Ala Leu Arg Ser Val Leu Gly
            100                 105                 110

Leu Trp Asn Ser Met Gly Tyr Ala Val Ile Cys Gly Gly Tyr Thr Lys
        115                 120                 125

Ser Pro Gly Glu Asn Asn Gln Lys Asp Phe His Tyr Thr Asp Glu Asn
    130                 135                 140

Gly Asn Gly Thr Thr Ile Asn Cys Gly Gly Ser Thr Asn Ser Asn Gly
145                 150                 155                 160

Thr His Ser Tyr Asn Gly Thr Asn Thr Leu Lys Ala Asp Lys Asn Val
                165                 170                 175

Ser Leu Ser Ile Glu Gln Tyr Glu Lys Ile His Glu Ala Tyr Gln Ile
            180                 185                 190

Leu Ser Lys Ala Leu Lys Gln Ala Gly Leu Ala Pro Leu Asn Ser Lys
        195                 200                 205

Gly Glu Lys Leu Glu Ala His Val Thr Thr Ser Lys Tyr Gln Gln Asp
    210                 215                 220

Asn Gln Thr Lys Thr Thr Thr Ser Val Ile Asp Thr Thr Asn Asp Ala
225                 230                 235                 240

Gln Asn Leu Leu Thr Gln Ala Gln Thr Ile Val Asn Thr Leu Lys Asp
                245                 250                 255

Tyr Cys Pro Ile Leu Ile Ala Lys Ser Ser Ser Ser Asn Gly Gly Thr
            260                 265                 270

Asn Asn Ala Asn Thr Pro Ser Trp Gln Thr Ala Gly Gly Gly Lys Asn
        275                 280                 285

Ser Cys Ala Thr Phe Gly Ala Glu Phe Ser Ala Ala Ser Asp Met Ile
    290                 295                 300

Asn Asn Ala Gln Lys Ile Val Gln Glu Thr Gln Gln Leu Ser Ala Asn
305                 310                 315                 320

Gln Pro Lys Asn Ile Thr Gln Pro His Asn Leu Asn Leu Asn Ser Pro
                325                 330                 335

Ser Ser Leu Thr Ala Leu Ala Gln Lys Met Leu Lys Asn Ala Gln Ser
            340                 345                 350

Gln Ala Glu Ile Leu Lys Leu Ala Asn Gln Val Glu Ser Asp Phe Asn
        355                 360                 365
```

```
Lys Leu Ser Ser Gly His Leu Lys Asp Tyr Ile Gly Lys Cys Asp Ala
    370                 375                 380

Ser Ala Ile Ser Ser Ala Asn Met Thr Met Gln Asn Gln Lys Asn Asn
385                 390                 395                 400

Trp Gly Asn Gly Cys Ala Gly Val Glu Glu Thr Gln Ser Leu Leu Lys
                405                 410                 415

Thr Ser Ala Ala Asp Phe Asn Asn Gln Thr Pro Gln Ile Asn Gln Ala
            420                 425                 430

Gln Asn Leu Ala Asn Thr Leu Ile Gln Glu Leu Gly Asn Asn Pro Phe
        435                 440                 445

Arg Asn Met Gly Met Ile Ala Ser Ser Thr Thr Asn Asn Gly Ala Leu
    450                 455                 460

Asn Gly Leu Gly Val Gln Val Gly Tyr Lys Gln Phe Phe Gly Glu Lys
465                 470                 475                 480

Lys Arg Trp Gly Leu Arg Tyr Tyr Gly Phe Phe Asp Tyr Asn His Ala
                485                 490                 495

Tyr Ile Lys Ser Asn Phe Phe Asn Ser Ala Ser Asp Val Trp Thr Tyr
            500                 505                 510

Gly Val Gly Ser Asp Leu Leu Phe Asn Phe Ile Asn Asp Lys Asn Thr
        515                 520                 525

Asn Phe Leu Gly Lys Asn Asn Lys Ile Ser Phe Gly Leu Phe Gly Gly
    530                 535                 540

Ile Ala Leu Ala Gly Thr Ser Trp Leu Asn Ser Gln Phe Val Asn Leu
545                 550                 555                 560

Lys Thr Ile Ser Asn Val Tyr Ser Ala Lys Val Asn Thr Ala Asn Phe
                565                 570                 575

Gln Phe Leu Phe Asn Leu Gly Leu Arg Thr Asn Leu Ala Arg Pro Lys
            580                 585                 590

Lys Lys Asp Ser His His Ala Ala Gln His Gly Met Glu Leu Gly Val
        595                 600                 605

Lys Ile Pro Thr Ile Asn Thr Asn Tyr Tyr Ser Phe Leu Asp Thr Lys
    610                 615                 620

Leu Glu Tyr Arg Arg Leu Tyr Ser Val Tyr Leu Asn Tyr Val Phe Ala
625                 630                 635                 640

Tyr

<210> SEQ ID NO 2
<211> LENGTH: 1926
<212> TYPE: DNA
<213> ORGANISM: Helicobacter pylori

<400> SEQUENCE: 2
atgaaaaaaa cgaaaaaaac aattttgctt tctctaactc ttgcggcatc actcttgcat      60
gctgaagaca acggcgtttt tttaagcgtg ggttatcaaa tcggtgaagc ggttcaaaaa     120
gtgaaaaacg ccgacaaggt gcaaaaactt tcagacactt atgaacaatt aagccggctt     180
ttaaccaacg ataatggcac aaactcaaag acaagcgcgc aagcgatcaa ccaagcggtt     240
aataatttga acgaacgcgc aaaaacttta gccggtggga caaccaattc ccctgcctat     300
caagccacgc ttttagcgtt gagatcggtg ttagggctat ggaatagcat gggttatgcg     360
gtcatatgcg gaggctatac caaaagtcca ggcgaaaaca atcaaaaaga tttccactac     420
accgatgaga atggcaacgg cactacaatc aattgcggtg ggagcacaaa tagtaatggc     480
actcatagtt ataatggcac aaatacatta aaagcagaca aaaatgtttc tctatctatt     540
```

```
gagcaatatg aaaaaatcca tgaagcttat cagattcttt caaaagcttt aaaacaagct    600
gggcttgctc ctttaaatag caaaggggaa aaattagaag cgcatgtaac cacatcaaag    660
tatcaacaag ataatcaaac taaaacgaca acttctgtta ttgatacgac taatgatgcg    720
caaaatcttt tgactcaagc gcaaacgatt gtcaataccc ttaaagatta ttgccccata    780
ttgatagcga aatcttctag tagtaatggc ggaactaata acgcaaacac cccttcatgg    840
caaacagccg gtggcggcaa aaattcatgc gcgacttttg gcgcggagtt tagtgccgct    900
tcagacatga ttaataatgc gcaaaaaatc gttcaagaaa cccaacaact cagcgccaac    960
caaccaaaaa atatcacaca accccataat ctcaacctta actctcctag cagtcttacg   1020
gctttagctc aaaaaatgct caaaaacgcg caatctcaag cagaaatttt aaaactagcc   1080
aatcaagtgg agagcgattt taacaaactt tcttcaggcc atcttaaaga ctacataggg   1140
aaatgcgatg cgagcgctat aagcagtgcg aatatgacaa tgcaaaatca aaagaacaat   1200
tgggggaacg ggtgtgctgg cgtggaagaa actcagtctt tgttaaaaac aagcgccgct   1260
gattttaaca accaaacgcc tcaaatcaat caagcacaaa acctagccaa cacccttatt   1320
caagaacttg gcaacaaccc ttttaggaat atgggcatga tcgcttcttc aaccacgaat   1380
aacggcgcct tgaatggtct tggggtgcaa gtgggttata agcaattttt tggagaaaag   1440
aaaagatggg ggttaaggta ttatggtttc tttgattaca accacgccta catcaaatcc   1500
aatttcttta actcggcttc tgatgtgtgg acttatgggg tgggtagcga tttgttgttt   1560
aatttcatca acgataaaaa caccaacttt ttaggcaaga ataacaagat ttcttttggg   1620
ctttttggag gcatcgcctt agcagggact tcatggctta attctcaatt cgtgaattta   1680
aaaaccatca gcaatgtcta tagcgctaaa gtgaatacgg ctaatttcca atttttattc   1740
aatttgggct tgagaaccaa tctcgctagg cctaagaaaa aagatagcca tcatgcagct   1800
caacatggca tggaattggg cgtgaaaatc cctaccatta acacgaatta ctattctttt   1860
ctagacacca aactagaata tagaaggctt tatagcgtgt atctcaatta tgtgttcgct   1920
tattaa                                                              1926
```

<210> SEQ ID NO 3
<211> LENGTH: 641
<212> TYPE: PRT
<213> ORGANISM: Helicobacter pylori

<400> SEQUENCE: 3

```
Met Lys Lys Thr Lys Lys Thr Ile Leu Leu Ser Leu Thr Leu Ala Ala
1               5                   10                  15

Ser Leu Leu His Ala Glu Asp Asn Gly Val Phe Leu Ser Val Gly Tyr
            20                  25                  30

Gln Ile Gly Glu Ala Val Gln Lys Val Lys Asn Ala Asp Lys Val Gln
        35                  40                  45

Lys Leu Ser Asp Thr Tyr Glu Gln Leu Ser Arg Leu Leu Thr Asn Asp
    50                  55                  60

Asn Gly Thr Asn Ser Lys Thr Ser Ala Gln Ala Ile Asn Gln Ala Val
65                  70                  75                  80

Asn Asn Leu Asn Glu Arg Ala Lys Thr Leu Ala Gly Gly Thr Thr Asn
                85                  90                  95

Ser Pro Ala Tyr Gln Ala Thr Leu Leu Ala Leu Arg Ser Val Leu Gly
            100                 105                 110

Leu Trp Asn Ser Met Gly Tyr Ala Val Ile Cys Gly Gly Tyr Thr Lys
        115                 120                 125
```

```
Ser Pro Gly Glu Asn Asn Gln Lys Asp Phe His Tyr Thr Asp Glu Asn
    130                 135                 140

Gly Asn Gly Thr Thr Ile Asn Cys Gly Gly Ser Thr Asn Ser Asn Gly
145                 150                 155                 160

Thr His Ser Ser Ser Gly Thr Asn Thr Leu Lys Ala Asp Lys Asn Val
                165                 170                 175

Ser Leu Ser Ile Glu Gln Tyr Glu Lys Ile His Glu Ala Tyr Gln Ile
            180                 185                 190

Leu Ser Lys Ala Leu Lys Gln Ala Gly Leu Ala Pro Leu Asn Ser Lys
        195                 200                 205

Gly Glu Lys Leu Glu Ala His Val Thr Thr Ser Lys Pro Glu Asn Asn
    210                 215                 220

Ser Gln Thr Lys Thr Thr Thr Ser Val Ile Asp Thr Thr Asn Asp Ala
225                 230                 235                 240

Gln Asn Leu Leu Thr Gln Ala Gln Thr Ile Val Asn Thr Leu Lys Asp
                245                 250                 255

Tyr Cys Pro Met Leu Ile Ala Lys Ser Ser Ser Glu Ser Ser Gly Ala
            260                 265                 270

Ala Thr Thr Asn Ala Pro Ser Trp Gln Thr Ala Gly Gly Gly Lys Asn
        275                 280                 285

Ser Cys Ala Thr Phe Gly Ala Glu Phe Ser Ala Ala Ser Asp Met Ile
    290                 295                 300

Asn Asn Ala Gln Lys Ile Val Gln Glu Thr Gln Gln Leu Ser Ala Asn
305                 310                 315                 320

Gln Pro Lys Asn Ile Thr Gln Pro His Asn Leu Asn Leu Asn Thr Pro
                325                 330                 335

Ser Ser Leu Thr Ala Leu Ala Gln Lys Met Leu Lys Asn Ala Gln Ser
            340                 345                 350

Gln Ala Glu Ile Leu Lys Leu Ala Asn Gln Val Glu Ser Asp Phe Asn
        355                 360                 365

Lys Leu Ser Ser Gly His Leu Lys Asp Tyr Ile Gly Lys Cys Asp Ala
    370                 375                 380

Ser Ala Ile Ser Ser Ala Asn Met Thr Met Gln Asn Gln Lys Asn Asn
385                 390                 395                 400

Trp Gly Asn Gly Cys Ala Gly Val Glu Glu Thr Leu Ser Ser Leu Lys
                405                 410                 415

Thr Ser Ala Ala Asp Phe Asn Asn Gln Thr Pro Gln Ile Asn Gln Ala
            420                 425                 430

Gln Asn Leu Ala Asn Thr Leu Ile Gln Glu Leu Gly Asn Asn Pro Phe
        435                 440                 445

Arg Asn Met Gly Met Ile Ala Ser Ser Thr Thr Asn Asn Gly Ala Leu
    450                 455                 460

Asn Gly Leu Gly Val Gln Val Gly Tyr Lys Gln Phe Phe Gly Glu Lys
465                 470                 475                 480

Lys Arg Trp Gly Leu Arg Tyr Tyr Gly Phe Phe Asp Tyr Asn His Ala
                485                 490                 495

Tyr Ile Lys Ser Asn Phe Phe Asn Ser Ala Ser Asp Val Trp Thr Tyr
            500                 505                 510

Gly Val Gly Ser Asp Leu Leu Phe Asn Phe Ile Asn Asp Lys Asn Thr
        515                 520                 525

Asn Phe Leu Gly Lys Asn Asn Lys Ile Ser Val Gly Phe Phe Gly Gly
    530                 535                 540
```

```
Ile Ala Leu Ala Gly Thr Ser Trp Leu Asn Ser Gln Phe Val Asn Leu
545                 550                 555                 560

Lys Thr Ile Ser Asn Val Tyr Ser Ala Lys Val Asn Thr Ala Asn Phe
                565                 570                 575

Gln Phe Leu Phe Asn Leu Gly Leu Arg Thr Asn Leu Ala Arg Pro Lys
            580                 585                 590

Lys Lys Asp Ser His His Ala Ala Gln His Gly Met Glu Leu Gly Val
        595                 600                 605

Lys Ile Pro Thr Ile Asn Thr Asn Tyr Tyr Ser Phe Leu Asp Thr Lys
    610                 615                 620

Leu Glu Tyr Arg Arg Leu Tyr Ser Val Tyr Leu Asn Tyr Val Phe Ala
625                 630                 635                 640

Tyr
```

<210> SEQ ID NO 4
<211> LENGTH: 1926
<212> TYPE: DNA
<213> ORGANISM: Helicobacter pylori

<400> SEQUENCE: 4

```
atgaaaaaaa cgaaaaaaac gattctgctt tctctaactc tcgcggcgtc attgctccat      60
gctgaagaca acggcgtttt tttaagcgtg ggttatcaaa tcggtgaagc ggttcaaaaa     120
gtgaaaaacg ccgacaaggt gcaaaaactt tcagacactt atgaacaatt aagccggctt     180
ttaaccaacg ataatggcac aaactcaaag acaagcgcgc aagcgatcaa ccaagcggtt     240
aataatttga acgaacgcgc aaaaacttta gccggtggga caaccaattc ccctgcctat     300
caagccacgc ttttagcgtt gagatcggtg ttagggctat ggaatagcat gggttatgcg     360
gtcatatgcg gaggttatac caaaagtcca ggcgaaaaca atcaaaaaga tttccactac     420
accgatgaga atggcaatgg cactacaatc aattgcggtg ggagcacaaa tagtaatggc     480
actcatagtt ctagtggcac aaatacatta aaagcagaca aaaatgtttc tctatctatt     540
gagcaatatg aaaaaatcca tgaagcttat cagattcttt caaaagcttt aaaacaagcc     600
gggcttgctc ctttaaatag caaaggggaa aagttagaag cgcatgtaac cacatcaaaa     660
ccagaaaata atagtcaaac taaaacgaca acttctgtta ttgatacgac taatgatgcg     720
caaaatcttt tgactcaagc gcaaacgatt gtcaataccc ttaaagatta ttgccccatg     780
ttgatagcga aatctagtag tgaaagtagt ggcgcagcta ctacaaacgc cccttcatgg     840
caaacagccg gtggcggcaa aaattcatgt gcgacttttg gtgcggagtt tagtgccgct     900
tcagacatga ttaataatgc gcaaaaaatc gttcaagaaa cccaacaact cagcgccaac     960
caaccaaaaa atatcacaca accccataat ctcaacctta acacccctag cagtcttacg    1020
gctttagctc aaaaaatgct caaaaatgcg caatctcaag cagaaatttt aaaactagcc    1080
aatcaagtgg agagcgattt taacaaactt tcttcaggcc atcttaaaga ctacataggg    1140
aaatgcgatg cgagcgctat aagcagtgcg aatatgacaa tgcaaaatca aaagaacaat    1200
tgggggaacg ggtgtgctgg cgtggaagaa actctgtctt cattaaaaac aagtgccgct    1260
gattttaaca accaaacgcc acaaatcaat caagcgcaaa acctagccaa cacccttatt    1320
caagaacttg gcaacaaccc ttttaggaat atgggcatga tcgcttcttc aaccacgaat    1380
aacggcgcct tgaatggcct tggggtgcaa gtgggttata agcaattttt tggggaaaag    1440
aaaagatggg ggttaaggta ttatggtttc tttgattaca accacgccta tatcaaatcc    1500
aatttcttta actcggcttc tgatgtgtgg acttatgggg tgggcagcga tttattgttt    1560
```

```
aatttcatca atgataaaaa caccaacttt ttaggcaaga ataacaagat ttcagtggga   1620
ttttttggag gtatcgcctt agcagggact tcatggctta attctcaatt cgtgaattta   1680
aaaaccatca gcaatgttta tagcgctaaa gtgaatacgg ctaacttcca atttttattc   1740
aatttgggct tgagaaccaa tctcgctaga cctaagaaaa aagatagtca tcatgcggct   1800
caacatggca tggaattggg cgtgaaaatc cctaccatta acacgaatta ttattctttt   1860
ctagacacta aactagaata tcgaaggctt tatagcgtgt atctcaatta tgtgtttgcc   1920
tattaa                                                              1926
```

```
<210> SEQ ID NO 5
<211> LENGTH: 632
<212> TYPE: PRT
<213> ORGANISM: Helicobacter pylori
<400> SEQUENCE: 5

Met Lys Lys Thr Lys Lys Thr Ile Leu Leu Ser Leu Thr Leu Ala Ser
1               5                   10                  15

Ser Leu Leu His Ala Glu Asp Asn Gly Val Phe Leu Ser Val Gly Tyr
            20                  25                  30

Gln Ile Gly Glu Ala Val Gln Lys Val Lys Asn Ala Asp Lys Val Gln
        35                  40                  45

Lys Leu Ser Asp Ala Tyr Glu Asn Leu Asn Lys Leu Leu Ala Asn His
    50                  55                  60

Ser His Ser Asn Pro Glu Ala Ile Asn Ala Asn Ser Ala Thr Ala Ile
65                  70                  75                  80

Asn Gln Ala Ile Gly Asn Leu Asn Ala Asn Thr Gln Asn Leu Ile Asp
                85                  90                  95

Lys Thr Asp Asn Ser Pro Ala Tyr Gln Ala Thr Leu Leu Ala Leu Lys
            100                 105                 110

Ser Thr Val Gly Leu Trp Asn Ser Ile Ala Tyr Ala Val Ile Cys Gly
        115                 120                 125

Gly Tyr Thr Asp Lys Pro Asn His Asn Thr Thr Glu Thr Phe Tyr Asn
    130                 135                 140

Gln Pro Gly Gln Gly Ser Asp Ser Ile Thr Cys Gly Gly His Val Gly
145                 150                 155                 160

Leu Leu Gln Ala Gly Lys Asn Asn Ser Leu Ser Ile Glu Gln Phe Ala
                165                 170                 175

Thr Leu Asn Lys Ala Tyr Gln Ile Ile Gln Ala Ala Leu Lys Gln Gly
            180                 185                 190

Leu Pro Ala Leu Ser Asp Thr Lys Lys Thr Val Glu Val Thr Ile Lys
        195                 200                 205

Thr Ala Thr Asn Ala Asn Asn Ile Asn Val Asn Asn Asn Asn Asn
    210                 215                 220

Ala Ala Asp Thr Thr Val Ser Ile Thr Asp Thr Phe Ile Asn Asp Ala
225                 230                 235                 240

Gln Asn Leu Leu Thr Gln Ala Gln Thr Ile Ile Asn Thr Leu Gln Asp
                245                 250                 255

Asn Cys Pro Gln Leu Lys Gly Lys Ser Ser Ser Asn Gly Gly Thr Asn
            260                 265                 270

Gly Ala Asn Thr Pro Ser Trp Gln Thr Gly Ala Asn Gln Asn Ser Cys
        275                 280                 285

Ser Val Phe Gly Thr Glu Phe Ser Ala Ile Ser Asp Met Ile Ser Asn
    290                 295                 300
```

```
Ala Gln Asn Ile Val Gln Glu Thr Gln Gln Leu Asn Thr Thr Pro Leu
305                 310                 315                 320

Lys Ser Ile Ala Gln Pro Asn Asn Phe Asn Leu Asn Ser Pro Asn Ser
                325                 330                 335

Ile Ala Leu Ala Gln Ser Met Leu Lys Asn Ala Gln Ser Gln Ala Ala
            340                 345                 350

Val Leu Lys Leu Ala Asn Gln Val Gly Ser Asp Phe Asn Arg Ile Ser
        355                 360                 365

Thr Gly Val Leu Lys Asn Tyr Ile Glu Glu Cys Asn Ala Asn Ala Ser
    370                 375                 380

Ser Glu Ser Val Ser Ser Asn Thr Trp Gly Lys Gly Cys Ala Gly Val
385                 390                 395                 400

Lys Gln Thr Leu Thr Ser Leu Glu Asn Ser Asn Ala Ser Phe Ser Ser
                405                 410                 415

Gln Thr Pro Gln Ile Asn Gln Ala Gln Asn Leu Ala Asn Thr Ile Val
            420                 425                 430

Gln Glu Leu Gly His Asn Pro Phe Lys Arg Val Gly Ile Ile Ser Ser
        435                 440                 445

Gln Thr Asn Asn Gly Ala Met Asn Gly Leu Gly Val Gln Val Gly Tyr
    450                 455                 460

Lys Gln Phe Phe Gly Glu Lys Lys Arg Trp Gly Leu Arg Tyr Tyr Gly
465                 470                 475                 480

Phe Phe Asp Tyr Asn His Thr Tyr Ile Lys Ser Asn Phe Phe Asn Ser
                485                 490                 495

Ala Ser Asp Val Trp Thr Tyr Gly Val Gly Ser Asp Leu Leu Phe Asn
            500                 505                 510

Phe Ile Asn Asp Lys Asn Thr Asn Phe Leu Gly Lys Asn Asn Gln Ile
        515                 520                 525

Ser Val Gly Leu Phe Gly Gly Ile Ala Leu Ala Gly Thr Ser Trp Leu
    530                 535                 540

Asn Ser Gln Phe Val Asn Leu Lys Thr Ile Ser Asn Val Tyr Ser Ala
545                 550                 555                 560

Lys Val Asn Thr Ala Asn Phe Gln Phe Leu Phe Asn Leu Gly Leu Arg
                565                 570                 575

Thr Asn Leu Ala Arg Pro Lys Lys Lys Asp Ser His His Ala Gly Gln
            580                 585                 590

His Gly Met Glu Leu Gly Val Lys Ile Pro Thr Ile Asn Thr Asn Tyr
        595                 600                 605

Tyr Ser Phe Leu Asp Thr Lys Leu Glu Tyr Arg Arg Leu Tyr Ser Val
    610                 615                 620

Tyr Leu Asn Tyr Val Phe Ala Tyr
625                 630
```

<210> SEQ ID NO 6
<211> LENGTH: 1899
<212> TYPE: DNA
<213> ORGANISM: Helicobacter pylori

<400> SEQUENCE: 6

```
atgaaaaaaa cgaaaaaaac gattctgctt tctctaactc ttgcgtcatc attgctccat     60
gctgaagaca acggcgtttt tttaagcgtg ggctatcaaa tcggtgaagc ggttcaaaaa    120
gtgaaaaacg ccgacaaggt gcaaaaactt tcagacgctt atgaaaactt aaacaagctt    180
ttagctaatc acagccactc caatccagaa gcgattaacg caaacagcgc cacagcgatc    240
```

```
aatcaagcga ttggtaattt aaacgcaaac acgcaaaatt taattgataa aacagacaat    300
tcccctgcct atcaagccac gcttttagcg ctaaaatcca cggtggggtt atggaatagc    360
atagcctacg ccgtcatatg cggaggctat acggataaac ccaatcacaa caccacagaa    420
actttttaca accagccagg acaaggttca gattcaatca cttgcggtgg gcatgtgggg    480
ttacttcaag caggcaaaaa taattctcta tccattgaac aatttgcaac gctcaataaa    540
gcgtatcaaa tcatccaagc cgctttgaaa caaggtctcc ctgctttaag cgatacaaaa    600
aaaacggtgg aagtaaccat taaaacagca accaacgcta acaacattaa tgtcaataat    660
aacaataaca atgctgctga cactacagtt agcataactg atacttttat taacgatgca    720
caaaaccttt taacccaagc gcaaaccatc atcaacaccc ttcaagacaa ttgcccgcaa    780
ttgaaaggga agtctagtag caatggtgga actaatggcg caaacacccc ttcatggcaa    840
acaggcgcta accaaaattc gtgcagcgtt tttggcacgg aatttagcgc tatttcagac    900
atgattagta acgctcaaaa catcgttcaa gaaacccaac agcttaatac caccccacta    960
aaaagcatcg cgcaacccaa caatttcaac cttaactccc ctaatagtat cgctttggct   1020
caaagcatgc tcaaaaacgc tcaatctcaa gcagcggttt taaaactggc caatcaagtg   1080
gggagcgatt ttaatagaat ttctacagga gttcttaaaa actatataga agaatgcaat   1140
gcgaatgctt caagtgaaag cgtttctagt aacacttggg ggaaaggctg cgcgggcgtg   1200
aaacaaactc taacttcgct agaaaatagc aacgcttctt tttctagcca aacgcctcaa   1260
atcaatcaag cgcaaaacct cgctaacacc attgttcaag aactcggtca taacccttc   1320
aaacgggtgg gcatcattag ctctcaaacc aataacgggg cgatgaatgg ccttggggtg   1380
caagtgggtt ataagcaatt ttttggagaa aagaaaagat gggggttaag gtattatggt   1440
ttctttgatt acaaccacac ctatatcaaa tccaatttct ttaactcggc ttctgatgtg   1500
tggacttatg gggtgggcag cgatttattg tttaacttca tcaacgataa aaacaccaac   1560
tttttaggta agaataacca gatttcagtg gggctttttg gggaatcgc cttagcaggg   1620
acttcatggc ttaattctca attcgtgaat ttaaaaacca tcagcaatgt ctatagcgct   1680
aaagtgaata cggctaattt ccaattttta ttcaatttgg gcttgagaac caatctcgct   1740
agacctaaga aaaaagatag ccatcatgcg ggtcaacatg gcatggaatt gggcgtgaaa   1800
atccctacca ttaacacgaa ttactattct tttctagaca ctaaactaga atataggagg   1860
ctttatagcg tgtatctcaa ttatgtgttt gcctattaa                          1899
```

<210> SEQ ID NO 7
<211> LENGTH: 12
<212> TYPE: PRT
<213> ORGANISM: Artificial Sequence
<220> FEATURE:
<223> OTHER INFORMATION: Targeting peptide

<400> SEQUENCE: 7

```
Asn Trp Tyr Leu Pro Trp Leu Gly Thr Asn Asp Trp
1               5                   10
```

<210> SEQ ID NO 8
<211> LENGTH: 53
<212> TYPE: DNA
<213> ORGANISM: Artificial Sequence
<220> FEATURE:
<223> OTHER INFORMATION: Forward primer

<400> SEQUENCE: 8
gtttaacttt aagaaggaga tatacaaatg gcggttcaaa aagtgaaaaa cgc 53

<210> SEQ ID NO 9
<211> LENGTH: 50
<212> TYPE: DNA
<213> ORGANISM: Artificial Sequence
<220> FEATURE:
<223> OTHER INFORMATION: Reverse primer

<400> SEQUENCE: 9
tcaagcttat taatgatgat gatgatggtg ggcgccgtta ttcgtggttg 50

<210> SEQ ID NO 10
<211> LENGTH: 43
<212> TYPE: DNA
<213> ORGANISM: Artificial Sequence
<220> FEATURE:
<223> OTHER INFORMATION: Forward primer

<400> SEQUENCE: 10
caccatcatc atcatcatta ataagcttga tccggctgct aac 43

<210> SEQ ID NO 11
<211> LENGTH: 30
<212> TYPE: DNA
<213> ORGANISM: Artificial Sequence
<220> FEATURE:
<223> OTHER INFORMATION: Reverse primer

<400> SEQUENCE: 11
gtttaacttt aagaaggaga tatacaaatg 30

<210> SEQ ID NO 12
<211> LENGTH: 23
<212> TYPE: DNA
<213> ORGANISM: Artificial Sequence
<220> FEATURE:
<223> OTHER INFORMATION: Forward primer

<400> SEQUENCE: 12
ggtgacgctc agaacctgct gac 23

<210> SEQ ID NO 13
<211> LENGTH: 23
<212> TYPE: DNA
<213> ORGANISM: Artificial Sequence
<220> FEATURE:
<223> OTHER INFORMATION: Reverse primer

<400> SEQUENCE: 13
accaccttta gagttcagcg gag 23

<210> SEQ ID NO 14
<211> LENGTH: 38
<212> TYPE: PRT
<213> ORGANISM: Artificial Sequence
<220> FEATURE:
<223> OTHER INFORMATION: HopQ-ID+HA

<400> SEQUENCE: 14

Glu Lys Leu Glu Ala His Val Thr Thr Ser Lys Tyr Gln Gln Asp Asn
1 5 10 15

Gln Thr Lys Thr Thr Thr Ser Val Ile Asp Thr Thr Asn Tyr Pro Tyr
20 25 30

```
Asp Val Pro Asp Tyr Ala
        35

<210> SEQ ID NO 15
<211> LENGTH: 641
<212> TYPE: PRT
<213> ORGANISM: Helicobacter pylori

<400> SEQUENCE: 15

Met Lys Lys Thr Lys Lys Thr Ile Leu Leu Ser Leu Thr Leu Ala Ser
1               5                   10                  15

Ser Leu Leu His Ala Glu Asp Asn Gly Val Phe Leu Ser Val Gly Tyr
            20                  25                  30

Gln Ile Gly Glu Ala Val Gln Lys Val Lys Asn Ala Asp Lys Val Gln
        35                  40                  45

Lys Leu Ser Asp Thr Tyr Glu Gln Leu Ser Arg Leu Leu Thr Asn Asp
    50                  55                  60

Asn Gly Thr Asn Ser Lys Thr Ser Ala Gln Ala Ile Asn Gln Ala Val
65                  70                  75                  80

Asn Asn Leu Asn Glu Arg Ala Lys Thr Leu Ala Gly Gly Thr Thr Asn
                85                  90                  95

Ser Pro Ala Tyr Gln Ala Thr Leu Leu Ala Leu Arg Ser Val Leu Gly
            100                 105                 110

Leu Trp Asn Ser Met Gly Tyr Ala Val Ile Cys Gly Gly Tyr Thr Lys
        115                 120                 125

Ser Pro Gly Glu Asn Asn Gln Lys Asn Phe His Tyr Thr Asp Glu Asn
    130                 135                 140

Gly Asn Gly Thr Thr Ile Asn Cys Gly Gly Ser Thr Asn Ser Asn Gly
145                 150                 155                 160

Thr His Ser Ser Asn Gly Thr Asn Thr Leu Lys Ala Asp Lys Asn Val
                165                 170                 175

Ser Leu Ser Ile Glu Gln Tyr Glu Lys Ile His Glu Ser Tyr Gln Ile
            180                 185                 190

Leu Ser Lys Ala Leu Lys Gln Ala Gly Leu Ala Pro Leu Asn Ser Lys
        195                 200                 205

Gly Glu Lys Leu Glu Ala His Val Thr Thr Ser Lys Tyr Gln Gln Asp
    210                 215                 220

Ser Gln Thr Lys Thr Thr Thr Ser Val Ile Asp Thr Thr Asn Asp Ala
225                 230                 235                 240

Gln Asn Leu Leu Thr Gln Ala Gln Thr Ile Val Asn Thr Leu Lys Asp
                245                 250                 255

Tyr Cys Pro Met Leu Ile Ala Lys Ser Ser Ser Gly Ser Gly Gly Gly
            260                 265                 270

Ala Ala Thr Asn Thr Pro Ser Trp Gln Thr Ala Gly Gly Gly Lys Asn
        275                 280                 285

Ser Cys Glu Thr Phe Gly Ala Glu Phe Ser Ala Ala Ser Asp Met Ile
    290                 295                 300

Asn Asn Ala Gln Lys Ile Val Gln Glu Thr Gln Gln Leu Ser Ala Asn
305                 310                 315                 320

Gln Pro Lys Asn Ile Thr Gln Pro His Asn Leu Asn Leu Asn Thr Pro
                325                 330                 335

Ser Ser Leu Thr Ala Leu Ala Gln Lys Met Leu Lys Asn Ala Gln Ser
            340                 345                 350

Gln Ala Glu Ile Leu Lys Leu Ala Asn Gln Val Glu Ser Asp Phe Asn
        355                 360                 365
```

```
Lys Leu Ser Ser Gly His Leu Lys Asp Tyr Ile Gly Lys Cys Asp Met
    370                 375                 380

Ser Ala Ile Ser Ser Thr Asn Met Thr Met Gln Ser Gln Lys Asn Asn
385                 390                 395                 400

Trp Gly Asn Gly Cys Ala Gly Val Glu Glu Thr Leu Thr Ser Leu Lys
                405                 410                 415

Thr Ser Ala Ala Asp Phe Asn Asn Gln Thr Pro Gln Ile Asn Gln Ala
            420                 425                 430

Gln Asn Leu Ala Asn Thr Leu Ile Gln Glu Leu Gly Asn Asn Pro Phe
        435                 440                 445

Arg Asn Met Gly Met Ile Ala Ser Ser Thr Thr Asn Asn Gly Ala Leu
    450                 455                 460

Asn Gly Leu Gly Val Gln Val Gly Tyr Lys Gln Phe Phe Gly Glu Lys
465                 470                 475                 480

Lys Arg Trp Gly Leu Arg Tyr Tyr Gly Phe Phe Asp Tyr Asn His Ala
                485                 490                 495

Tyr Ile Lys Ser Asn Phe Phe Asn Ser Ala Ser Asp Val Trp Thr Tyr
            500                 505                 510

Gly Val Gly Ser Asp Leu Leu Phe Asn Phe Ile Asn Asp Lys Asn Thr
        515                 520                 525

Asn Phe Leu Gly Lys Asn Asn Gln Ile Ser Phe Gly Leu Phe Gly Gly
    530                 535                 540

Ile Ala Leu Ala Gly Thr Ser Trp Leu Asn Ser Gln Phe Val Asn Leu
545                 550                 555                 560

Lys Thr Ile Ser Asn Val Tyr Ser Ala Lys Val Asn Thr Ala Asn Phe
                565                 570                 575

Gln Phe Leu Phe Asn Leu Gly Leu Arg Thr Asn Leu Ala Arg Pro Lys
            580                 585                 590

Lys Lys Asp Ser His His Ala Ala Gln His Gly Ile Glu Leu Gly Val
        595                 600                 605

Lys Ile Pro Thr Ile Asn Thr Asn Tyr Tyr Ser Phe Leu Asp Thr Lys
    610                 615                 620

Leu Glu Tyr Arg Arg Leu Tyr Ser Val Tyr Leu Asn Tyr Val Phe Ala
625                 630                 635                 640

Tyr
```

<210> SEQ ID NO 16
<211> LENGTH: 1926
<212> TYPE: DNA
<213> ORGANISM: Helicobacter pylori

<400> SEQUENCE: 16

```
atgaaaaaaa cgaaaaaaac gattctgctt tctctaactc ttgcgtcatc attgctccat     60
gctgaagaca acggcgtttt tttaagcgtg ggttatcaaa ttggtgaagc ggttcaaaaa    120
gtgaaaaacg ccgacaaggt gcaaaaactt tcagacactt atgaacaatt aagccggctt    180
ttaaccaacg ataatggcac aaactcaaag acaagcgcgc aagcgatcaa ccaagcggtt    240
aataatttga acgaacgcgc aaaaacttta gccggtggga caaccaattc ccctgcctat    300
caagccacgc ttttagcgtt aagatcggtg ttagggctat ggaatagcat gggttatgcg    360
gtcatatgcg gaggttatac caaaagtcca ggcgaaaaca atcaaaaaaa tttccactac    420
accgatgaga atggcaacgg cactacaatc aattgcggtg ggagcacaaa tagtaatggc    480
actcatagtt ctaatggcac aaatacatta aaagcagaca aaaatgtttc tctatctatt    540
```

```
gagcaatatg aaaaaatcca tgaatcctat cagattcttt caaaagcttt aaaacaagcc    600
gggcttgctc ctttaaatag caaaggggaa aagttagaag cgcatgtaac cacatcaaag    660
tatcaacaag atagtcaaac taaaacgaca acttctgtta ttgatacgac taatgatgcg    720
caaaatcttt tgactcaagc gcaaacgatt gtcaataccc ttaaagatta ttgccccatg    780
ttgatagcga aatctagtag tggaagtggt ggcggagctg ctacaaacac cccttcatgg    840
caaacagccg gtggcggcaa aaattcatgc gagacttttg gtgcggagtt tagtgccgct    900
tcagacatga ttaataatgc gcaaaaaatc gttcaagaaa cccaacaact cagcgccaac    960
caaccaaaaa atatcacaca accccataat ctcaacctta acacccctag cagtcttacg   1020
gctttagctc aaaaaatgct caaaaacgcg caatctcaag cagaaatttt aaaactagcc   1080
aatcaagtgg agagcgattt taacaaactt tcttcaggcc atcttaaaga ctacataggg   1140
aaatgcgata tgagtgctat aagcagtacg aatatgacaa tgcaaagtca aaagaacaat   1200
tgggggaacg ggtgcgctgg cgtggaagaa actctaactt cattaaaaac aagcgccgct   1260
gattttaaca accaaacgcc tcaaatcaat caagcgcaaa acctagctaa caccccttatt  1320 caagaacttg gcaacaaccc ttttaggaat atgggcatga tcgcttcttc aaccacgaat   1380
aacggcgcct tgaatggcct tggggtgcaa gtgggttata agcaattttt tggagaaaag   1440
aaaagatggg ggttgagata ttatggtttc tttgattaca accacgccta tatcaaatcc   1500
aatttcttta attcggcttc tgatgtgtgg acttatgggg tgggtagcga tttattgttt   1560
aatttcatca acgataaaaa caccaacttt ttaggcaaga ataaccagat ttcttttggg   1620
ctttttggag gaatcgcctt agcagggact tcatggctta attctcaatt cgtgaattta   1680
aaaaccatca gcaatgtcta tagcgctaaa gtgaatacgg ctaacttcca atttttattc   1740
aatctcggct tgagaaccaa tctcgctagg cctaagaaaa aagatagcca tcatgcggct   1800
caacatggca tagaattagg cgtgaaaatc cctaccatta acacgaatta ctattctttt   1860
ctagacacta aactagaata tagaaggctt tatagcgtgt atctcaatta tgtgttcgcg   1920
tattaa                                                              1926
```

```
<210> SEQ ID NO 17
<211> LENGTH: 14
<212> TYPE: PRT
<213> ORGANISM: Artificial Sequence
<220> FEATURE:
<223> OTHER INFORMATION: General consensus sequence
<220> FEATURE:
<221> NAME/KEY: MISC_FEATURE
<222> LOCATION: (5)..(5)
<223> OTHER INFORMATION: Xaa is Thr or Tyr or is deleted
<220> FEATURE:
<221> NAME/KEY: MISC_FEATURE
<222> LOCATION: (6)..(6)
<223> OTHER INFORMATION: Xaa is Lys or Asn or is deleted
<220> FEATURE:
<221> NAME/KEY: MISC_FEATURE
<222> LOCATION: (7)..(7)
<223> OTHER INFORMATION: Xaa is Ser, Lys, Asn or Thr or is deleted
<220> FEATURE:
<221> NAME/KEY: MISC_FEATURE
<222> LOCATION: (9)..(9)
<223> OTHER INFORMATION: Xaa is Gly, Ser, Gln, Arg, Thr, Ile or Val or
      is deleted
<220> FEATURE:
<221> NAME/KEY: MISC_FEATURE
<222> LOCATION: (11)..(11)
<223> OTHER INFORMATION: Xaa is Asn or Gly or is deleted
<220> FEATURE:
<221> NAME/KEY: MISC_FEATURE
```

<222> LOCATION: (12)..(12)
<223> OTHER INFORMATION: Xaa is Asn or His or is deleted

<400> SEQUENCE: 17

Cys Gly Gly Tyr Xaa Xaa Xaa Pro Xaa Glu Xaa Xaa Gln Lys
1 5 10

<210> SEQ ID NO 18
<211> LENGTH: 30
<212> TYPE: PRT
<213> ORGANISM: Artificial Sequence
<220> FEATURE:
<223> OTHER INFORMATION: General consensus sequence
<220> FEATURE:
<221> NAME/KEY: MISC_FEATURE
<222> LOCATION: (4)..(4)
<223> OTHER INFORMATION: Xaa is Ser, Gly, Asn, Thr or Phe or is deleted
<220> FEATURE:
<221> NAME/KEY: MISC_FEATURE
<222> LOCATION: (5)..(5)
<223> OTHER INFORMATION: Xaa is Thr or Ile or is deleted
<220> FEATURE:
<221> NAME/KEY: MISC_FEATURE
<222> LOCATION: (6)..(6)
<223> OTHER INFORMATION: Xaa is Asn, Gly or Lys or is deleted
<220> FEATURE:
<221> NAME/KEY: MISC_FEATURE
<222> LOCATION: (7)..(7)
<223> OTHER INFORMATION: Xaa is Ser or Ala or is deleted
<220> FEATURE:
<221> NAME/KEY: MISC_FEATURE
<222> LOCATION: (8)..(8)
<223> OTHER INFORMATION: Xaa is Asn or Asp or is deleted
<220> FEATURE:
<221> NAME/KEY: MISC_FEATURE
<222> LOCATION: (10)..(10)
<223> OTHER INFORMATION: Xaa is Gln, Lys or Arg or is deleted
<220> FEATURE:
<221> NAME/KEY: MISC_FEATURE
<222> LOCATION: (11)..(11)
<223> OTHER INFORMATION: Xaa is Thr, Val or Ser or is deleted
<220> FEATURE:
<221> NAME/KEY: MISC_FEATURE
<222> LOCATION: (12)..(12)
<223> OTHER INFORMATION: Xaa is His, Gln or Tyr or is deleted
<220> FEATURE:
<221> NAME/KEY: MISC_FEATURE
<222> LOCATION: (13)..(13)
<223> OTHER INFORMATION: Xaa is Ser or Asn or is deleted
<220> FEATURE:
<221> NAME/KEY: MISC_FEATURE
<222> LOCATION: (14)..(14)
<223> OTHER INFORMATION: Xaa is Ser, Pro or Asn or is deleted
<220> FEATURE:
<221> NAME/KEY: MISC_FEATURE
<222> LOCATION: (15)..(15)
<223> OTHER INFORMATION: Xaa is Asn or Ser or is deleted
<220> FEATURE:
<221> NAME/KEY: MISC_FEATURE
<222> LOCATION: (17)..(17)
<223> OTHER INFORMATION: Xaa is Thr or Val
<220> FEATURE:
<221> NAME/KEY: MISC_FEATURE
<222> LOCATION: (18)..(18)
<223> OTHER INFORMATION: Xaa is Asn or Ser
<220> FEATURE:
<221> NAME/KEY: MISC_FEATURE
<222> LOCATION: (19)..(19)
<223> OTHER INFORMATION: Xaa is Thr, Leu or Met or is deleted
<220> FEATURE:
<221> NAME/KEY: MISC_FEATURE
<222> LOCATION: (21)..(21)
<223> OTHER INFORMATION: Xaa is Lys or Pro or is deleted
<220> FEATURE:
<221> NAME/KEY: MISC_FEATURE
<222> LOCATION: (23)..(23)
<223> OTHER INFORMATION: Xaa is Asp, Gly or Ala or is deleted

```
<220> FEATURE:
<221> NAME/KEY: MISC_FEATURE
<222> LOCATION: (25)..(25)
<223> OTHER INFORMATION: Xaa is Asn or Gly or is deleted
<220> FEATURE:
<221> NAME/KEY: MISC_FEATURE
<222> LOCATION: (26)..(26)
<223> OTHER INFORMATION: Xaa is Val or Ser or is deleted

<400> SEQUENCE: 18

Cys Gly Gly Xaa Xaa Xaa Xaa Xaa Gly Xaa Xaa Xaa Xaa Xaa Xaa Gly
1               5                   10                  15

Xaa Xaa Xaa Leu Xaa Ala Xaa Lys Xaa Xaa Ser Leu Ser Ile
            20                  25                  30

<210> SEQ ID NO 19
<211> LENGTH: 33
<212> TYPE: PRT
<213> ORGANISM: Artificial Sequence
<220> FEATURE:
<223> OTHER INFORMATION: General consensus sequence
<220> FEATURE:
<221> NAME/KEY: MISC_FEATURE
<222> LOCATION: (3)..(3)
<223> OTHER INFORMATION: Xaa is Met, Ile or Val or is deleted
<220> FEATURE:
<221> NAME/KEY: MISC_FEATURE
<222> LOCATION: (6)..(6)
<223> OTHER INFORMATION: Xaa is Ala or Gly or is deleted
<220> FEATURE:
<221> NAME/KEY: MISC_FEATURE
<222> LOCATION: (7)..(7)
<223> OTHER INFORMATION: Xaa is Lys or Arg or is deleted
<220> FEATURE:
<221> NAME/KEY: MISC_FEATURE
<222> LOCATION: (8)..(8)
<223> OTHER INFORMATION: Xaa is Ser or Thr or is deleted
<220> FEATURE:
<221> NAME/KEY: MISC_FEATURE
<222> LOCATION: (9)..(9)
<223> OTHER INFORMATION: Xaa is Ser or Thr or is deleted
<220> FEATURE:
<221> NAME/KEY: MISC_FEATURE
<222> LOCATION: (10)..(10)
<223> OTHER INFORMATION: Xaa is Ser, Asn or Gly or is deleted
<220> FEATURE:
<221> NAME/KEY: MISC_FEATURE
<222> LOCATION: (11)..(11)
<223> OTHER INFORMATION: Xaa is Gly, Asn, Glu, Ser or Asp or is deleted
<220> FEATURE:
<221> NAME/KEY: MISC_FEATURE
<222> LOCATION: (12)..(12)
<223> OTHER INFORMATION: Xaa is Ser, Gly or Asn or is deleted
<220> FEATURE:
<221> NAME/KEY: MISC_FEATURE
<222> LOCATION: (13)..(13)
<223> OTHER INFORMATION: Xaa is Ser, Met, Gly, Asn or Thr or is deleted
<220> FEATURE:
<221> NAME/KEY: MISC_FEATURE
<222> LOCATION: (14)..(14)
<223> OTHER INFORMATION: Xaa is Gly, Ala, Thr, Ser, Asn or Met or is
      deleted
<220> FEATURE:
<221> NAME/KEY: MISC_FEATURE
<222> LOCATION: (15)..(15)
<223> OTHER INFORMATION: Xaa is Gly, Asn, Thr, Ala or Val or is deleted
<220> FEATURE:
<221> NAME/KEY: MISC_FEATURE
<222> LOCATION: (16)..(16)
<223> OTHER INFORMATION: Xaa is Ala, Asn, Gly or Ser or is deleted
<220> FEATURE:
<221> NAME/KEY: MISC_FEATURE
<222> LOCATION: (17)..(17)
<223> OTHER INFORMATION: Xaa is Thr, Asn, Ala, Gly or Ser or is deleted
<220> FEATURE:
<221> NAME/KEY: MISC_FEATURE
```

<222> LOCATION: (18)..(18)
<223> OTHER INFORMATION: Xaa is Thr or Ala or is deleted
<220> FEATURE:
<221> NAME/KEY: MISC_FEATURE
<222> LOCATION: (20)..(20)
<223> OTHER INFORMATION: Xaa is Thr or Ala or is deleted
<220> FEATURE:
<221> NAME/KEY: MISC_FEATURE
<222> LOCATION: (25)..(25)
<223> OTHER INFORMATION: Xaa is Thr or Ile or is deleted
<220> FEATURE:
<221> NAME/KEY: MISC_FEATURE
<222> LOCATION: (26)..(26)
<223> OTHER INFORMATION: Xaa is Ala, Ser, Thr or Asn or is deleted
<220> FEATURE:
<221> NAME/KEY: MISC_FEATURE
<222> LOCATION: (27)..(27)
<223> OTHER INFORMATION: Xaa is Gly or Ser or is deleted
<220> FEATURE:
<221> NAME/KEY: MISC_FEATURE
<222> LOCATION: (28)..(28)
<223> OTHER INFORMATION: Xaa is Gly or Asn or is deleted
<220> FEATURE:
<221> NAME/KEY: MISC_FEATURE
<222> LOCATION: (29)..(29)
<223> OTHER INFORMATION: Xaa is Gly, Leu or Ser or is deleted
<220> FEATURE:
<221> NAME/KEY: MISC_FEATURE
<222> LOCATION: (32)..(32)
<223> OTHER INFORMATION: Xaa is Ser or Ala or is deleted

<400> SEQUENCE: 19

```
Cys Pro Xaa Leu Ile Xaa Xaa Xaa Xaa Xaa Xaa Xaa Xaa Xaa Xaa Xaa
1               5                   10                  15

Xaa Xaa Asn Xaa Pro Ser Trp Gln Xaa Xaa Xaa Xaa Xaa Lys Asn Xaa
            20                  25                  30

Cys
```

<210> SEQ ID NO 20
<211> LENGTH: 41
<212> TYPE: PRT
<213> ORGANISM: Artificial Sequence
<220> FEATURE:
<223> OTHER INFORMATION: General consensus sequence
<220> FEATURE:
<221> NAME/KEY: MISC_FEATURE
<222> LOCATION: (3)..(3)
<223> OTHER INFORMATION: Xaa is Gly or Asp or is deleted
<220> FEATURE:
<221> NAME/KEY: MISC_FEATURE
<222> LOCATION: (4)..(4)
<223> OTHER INFORMATION: Xaa is His or Tyr or is deleted
<220> FEATURE:
<221> NAME/KEY: MISC_FEATURE
<222> LOCATION: (7)..(7)
<223> OTHER INFORMATION: Xaa is Asp or Asn or is deleted
<220> FEATURE:
<221> NAME/KEY: MISC_FEATURE
<222> LOCATION: (10)..(10)
<223> OTHER INFORMATION: Xaa is Gly or Arg or is deleted
<220> FEATURE:
<221> NAME/KEY: MISC_FEATURE
<222> LOCATION: (14)..(14)
<223> OTHER INFORMATION: Xaa is Met, Ala or Val or is deleted
<220> FEATURE:
<221> NAME/KEY: MISC_FEATURE
<222> LOCATION: (16)..(16)
<223> OTHER INFORMATION: Xaa is Ala or Gly or is deleted
<220> FEATURE:
<221> NAME/KEY: MISC_FEATURE
<222> LOCATION: (17)..(17)
<223> OTHER INFORMATION: Xaa is Ile or Val or is deleted
<220> FEATURE:
<221> NAME/KEY: MISC_FEATURE
<222> LOCATION: (19)..(19)

<223> OTHER INFORMATION: Xaa is Ser or Gly or is deleted
<220> FEATURE:
<221> NAME/KEY: MISC_FEATURE
<222> LOCATION: (20)..(20)
<223> OTHER INFORMATION: Xaa is any amino acid or is deleted
<220> FEATURE:
<221> NAME/KEY: MISC_FEATURE
<222> LOCATION: (21)..(21)
<223> OTHER INFORMATION: Xaa is any amino acid or is deleted
<220> FEATURE:
<221> NAME/KEY: MISC_FEATURE
<222> LOCATION: (22)..(22)
<223> OTHER INFORMATION: Xaa is any amino acid or is deleted
<220> FEATURE:
<221> NAME/KEY: MISC_FEATURE
<222> LOCATION: (23)..(23)
<223> OTHER INFORMATION: Xaa is Thr, Ala or Ser or is deleted
<220> FEATURE:
<221> NAME/KEY: MISC_FEATURE
<222> LOCATION: (26)..(26)
<223> OTHER INFORMATION: Xaa is Thr or Ala or is deleted
<220> FEATURE:
<221> NAME/KEY: MISC_FEATURE
<222> LOCATION: (27)..(27)
<223> OTHER INFORMATION: Xaa is Met, Pro, Ala or Gln or is deleted
<220> FEATURE:
<221> NAME/KEY: MISC_FEATURE
<222> LOCATION: (28)..(28)
<223> OTHER INFORMATION: Xaa is Gln, Arg, Lys or His or is deleted
<220> FEATURE:
<221> NAME/KEY: MISC_FEATURE
<222> LOCATION: (29)..(29)
<223> OTHER INFORMATION: Xaa is Ser or Asn or is deleted
<220> FEATURE:
<221> NAME/KEY: MISC_FEATURE
<222> LOCATION: (30)..(30)
<223> OTHER INFORMATION: Xaa is Gln or Met or is deleted
<220> FEATURE:
<221> NAME/KEY: MISC_FEATURE
<222> LOCATION: (32)..(32)
<223> OTHER INFORMATION: Xaa is Asn or Ser or is deleted
<220> FEATURE:
<221> NAME/KEY: MISC_FEATURE
<222> LOCATION: (33)..(33)
<223> OTHER INFORMATION: Xaa is Asn or Thr or is deleted
<220> FEATURE:
<221> NAME/KEY: MISC_FEATURE
<222> LOCATION: (34)..(34)
<223> OTHER INFORMATION: Xaa is Thr, Asn or Ile or is deleted
<220> FEATURE:
<221> NAME/KEY: MISC_FEATURE
<222> LOCATION: (37)..(37)
<223> OTHER INFORMATION: Xaa is Asn or Lys or is deleted

<400> SEQUENCE: 20

Ser Ser Xaa Xaa Leu Lys Xaa Tyr Ile Xaa Lys Cys Asp Xaa Ser Xaa
1 5 10 15

Xaa Ser Xaa Xaa Xaa Xaa Xaa Asn Met Xaa Xaa Xaa Xaa Xaa Lys Xaa
20 25 30

Xaa Xaa Trp Gly Xaa Gly Cys Ala Gly
35 40

<210> SEQ ID NO 21
<211> LENGTH: 14
<212> TYPE: PRT
<213> ORGANISM: Artificial Sequence
<220> FEATURE:
<223> OTHER INFORMATION: Peptide

<400> SEQUENCE: 21

Cys Gly Gly Tyr Thr Lys Ser Pro Gly Glu Asn Asn Gln Lys
1 5 10

<210> SEQ ID NO 22
<211> LENGTH: 29
<212> TYPE: PRT
<213> ORGANISM: Artificial Sequence
<220> FEATURE:
<223> OTHER INFORMATION: Peptide

<400> SEQUENCE: 22

Cys Gly Gly Ser Thr Asn Ser Asn Gly Thr His Ser Ser Asn Gly Thr
1 5 10 15

Asn Thr Leu Lys Ala Asp Lys Asn Val Ser Leu Ser Ile
20 25

<210> SEQ ID NO 23
<211> LENGTH: 30
<212> TYPE: PRT
<213> ORGANISM: Artificial Sequence
<220> FEATURE:
<223> OTHER INFORMATION: Consensus sequence

<400> SEQUENCE: 23

Cys Gly Gly Ser Thr Asn Ser Asn Gly Gln Thr His Ser Ser Asn Gly
1 5 10 15

Thr Asn Thr Leu Lys Ala Asp Lys Asn Val Ser Leu Ser Ile
20 25 30

<210> SEQ ID NO 24
<211> LENGTH: 33
<212> TYPE: PRT
<213> ORGANISM: Artificial Sequence
<220> FEATURE:
<223> OTHER INFORMATION: Peptide

<400> SEQUENCE: 24

Cys Pro Met Leu Ile Ala Lys Ser Ser Ser Gly Ser Gly Gly Gly Ala
1 5 10 15

Ala Thr Asn Thr Pro Ser Trp Gln Thr Ala Gly Gly Gly Lys Asn Ser
20 25 30

Cys

<210> SEQ ID NO 25
<211> LENGTH: 33
<212> TYPE: PRT
<213> ORGANISM: Artificial Sequence
<220> FEATURE:
<223> OTHER INFORMATION: Consensus sequence

<400> SEQUENCE: 25

Cys Pro Met Leu Ile Ala Lys Ser Ser Ser Gly Ser Ser Gly Gly Ala
1 5 10 15

Thr Thr Asn Thr Pro Ser Trp Gln Thr Ala Gly Gly Gly Lys Asn Ser
20 25 30

Cys

<210> SEQ ID NO 26
<211> LENGTH: 37
<212> TYPE: PRT
<213> ORGANISM: Artificial Sequence
<220> FEATURE:
<223> OTHER INFORMATION: Peptide

<400> SEQUENCE: 26

Ser Ser Gly His Leu Lys Asp Tyr Ile Gly Lys Cys Asp Met Ser Ala
1 5 10 15

```
Ile Ser Ser Thr Asn Met Thr Met Gln Ser Gln Lys Asn Asn Trp Gly
            20                  25                  30

Asn Gly Cys Ala Gly
        35

<210> SEQ ID NO 27
<211> LENGTH: 38
<212> TYPE: PRT
<213> ORGANISM: Artificial Sequence
<220> FEATURE:
<223> OTHER INFORMATION: Consensus sequence

<400> SEQUENCE: 27

Ser Ser Gly His Leu Lys Asp Tyr Ile Gly Lys Cys Asp Ala Ser Ala
1               5                   10                  15

Ile Ser Ser Ala Asn Met Thr Met Gln Asn Gln Lys Asn Asn Thr Trp
            20                  25                  30

Gly Asn Gly Cys Ala Gly
        35

<210> SEQ ID NO 28
<211> LENGTH: 108
<212> TYPE: PRT
<213> ORGANISM: Homo sapiens

<400> SEQUENCE: 28

Gln Leu Thr Thr Glu Ser Met Pro Phe Asn Val Ala Glu Gly Lys Glu
1               5                   10                  15

Val Leu Leu Leu Val His Asn Leu Pro Gln Gln Leu Phe Gly Tyr Ser
            20                  25                  30

Trp Tyr Lys Gly Glu Arg Val Asp Gly Asn Arg Gln Ile Val Gly Tyr
        35                  40                  45

Ala Ile Gly Thr Gln Gln Ala Thr Pro Gly Pro Ala Asn Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro
            100                 105

<210> SEQ ID NO 29
<211> LENGTH: 110
<212> TYPE: PRT
<213> ORGANISM: Homo sapiens

<400> SEQUENCE: 29

Lys Leu Thr Ile Glu Ser Thr Pro Phe Asn Val Ala Glu Gly Lys Glu
1               5                   10                  15

Val Leu Leu Leu Val His Asn Leu Pro Gln His Leu Phe Gly Tyr Ser
            20                  25                  30

Trp Tyr Lys Gly Glu Arg Val Asp Gly Asn Arg Gln Ile Ile Gly Tyr
        35                  40                  45

Val Ile Gly Thr Gln Gln Ala Thr Pro Gly Pro Ala Tyr Ser Gly Arg
    50                  55                  60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
```

```
                85                  90                  95

Asn Glu Glu Ala Thr Gly Gln Phe Arg Val Tyr Pro Glu Leu
            100                 105                 110

<210> SEQ ID NO 30
<211> LENGTH: 108
<212> TYPE: PRT
<213> ORGANISM: Homo sapiens

<400> SEQUENCE: 30

Lys Leu Thr Ile Glu Ser Thr Pro Phe Asn Val Ala Glu Gly Lys Glu
1               5                   10                  15

Val Leu Leu Leu Ala His Asn Leu Pro Gln Asn Arg Ile Gly Tyr Ser
            20                  25                  30

Trp Tyr Lys Gly Glu Arg Val Asp Gly Asn Ser Leu Ile Val Gly Tyr
        35                  40                  45

Val Ile Gly Thr Gln Gln Ala Thr Pro Gly Pro Ala Tyr Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro
            100                 105

<210> SEQ ID NO 31
<211> LENGTH: 108
<212> TYPE: PRT
<213> ORGANISM: Homo sapiens

<400> SEQUENCE: 31

Gln Leu Thr Ile Glu Ala Val Pro Ser Asn Ala Ala Glu Gly Lys Glu
1               5                   10                  15

Val Leu Leu Leu Val His Asn Leu Pro Gln Asp Pro Arg Gly Tyr Asn
            20                  25                  30

Trp Tyr Lys Gly Glu Thr Val Asp Ala Asn Arg Arg Ile Ile Gly Tyr
        35                  40                  45

Val Ile Ser Asn Gln Gln Ile Thr Pro Gly Pro Ala Tyr Ser Asn Arg
    50                  55                  60

Glu Thr Ile Tyr Pro Asn Ala Ser Leu Leu Met Arg Asn Val Thr Arg
65                  70                  75                  80

Asn Asp Thr Gly Ser Tyr Thr Leu Gln Val Ile Lys Leu Asn Leu Met
                85                  90                  95

Ser Glu Glu Val Thr Gly Gln Phe Ser Val His Pro
            100                 105

<210> SEQ ID NO 32
<211> LENGTH: 99
<212> TYPE: PRT
<213> ORGANISM: Rattus norvegicus

<400> SEQUENCE: 32

Pro Pro Asn Val Val Glu Glu Ser Ser Val Leu Leu Leu Thr His Asn
1               5                   10                  15

Leu Pro Gln Glu Phe Gln Val Phe Tyr Trp Tyr Lys Val Thr Thr Thr
            20                  25                  30

Gly Leu Asn Ser Glu Ile Ala Arg Tyr Ile Arg Ser Ser Asn Thr Ser
        35                  40                  45
```

-continued

```
Gln Thr Glu Pro Ala Tyr Ser Gly Arg Val Thr Ile Tyr Ser Asn Gly
    50                  55                  60

Ser Leu Phe Phe Gln Asn Val Asn Lys Thr Asp Glu Gly Pro Tyr Thr
65                  70                  75                  80

Leu Ser Val Ile Asp Lys Gln Phe Asn Pro Ile Gln Thr Ser Val Gln
                85                  90                  95

Phe Arg Val

<210> SEQ ID NO 33
<211> LENGTH: 108
<212> TYPE: PRT
<213> ORGANISM: Mus musculus

<400> SEQUENCE: 33

Glu Val Thr Ile Glu Ala Val Pro Pro Gln Val Ala Glu Asp Asn Asn
1               5                   10                  15

Val Leu Leu Leu Val His Asn Leu Pro Leu Ala Leu Gly Ala Phe Ala
            20                  25                  30

Trp Tyr Lys Gly Asn Thr Thr Ala Ile Asp Lys Glu Ile Ala Arg Phe
        35                  40                  45

Val Pro Asn Ser Asn Met Asn Phe Thr Gly Gln Ala Tyr Ser Gly Arg
    50                  55                  60

Glu Ile Ile Tyr Ser Asn Gly Ser Leu Leu Phe Gln Met Ile Thr Met
65                  70                  75                  80

Lys Asp Met Gly Val Tyr Thr Leu Asp Met Thr Asp Glu Asn Tyr Arg
                85                  90                  95

Arg Thr Gln Ala Thr Val Arg Phe His Val His Pro
            100                 105
```

METHODS FOR TREATMENT OF *H. PYLORI* INFECTIONS

CROSS-REFERENCE TO RELATED APPLICATIONS

This application is a U.S. National Stage Application under 35 U.S.C. § 371 of International Application No. PCT/EP2017/068297, filed Jul. 20, 2017, which claims the benefit of and priority to European Patent Application No. 16180430.7, filed Jul. 20, 2016. Each of these applications is hereby incorporated by reference in its entirety.

REFERENCE TO A SEQUENCE LISTING

A sequence listing containing SEQ ID NOs: 1-33 is provided herewith in a computer-readable nucleotide/amino acid .txt file and is specifically incorporated by reference. The name of the ASCII text file is 120-18 US seqlisting 14apr2020, date of creation is Apr. 14, 2020, and the size is 50k bytes.

TECHNICAL FIELD OF THE INVENTION

The present invention relates to inhibitors of the interaction between *H. pylori* HopQ and a member of the carcinoembryonic antigen-related cell adhesion molecule (CEACAM) family as well as to immunogenic compositions based on *H. pylori* HopQ. The present invention further relates to the use of the inhibitors and immunogenic compositions for preventing or treating a disease or disorder caused by or associated with *H. pylori.*

BACKGROUND OF THE INVENTION

*Helicobacter pylori* (*H. pylori*) is a microaerophilic gram-negative bacterium, able to persist lifelong in the human stomach. *H. pylori* infection is the most common bacterial infectious disease in humans: about half of the worldwide population is infected with *H. pylori*, depending on the socioeconomic status of the region (Perez-Perez et al., 2004). The infection is associated with numerous gastric diseases such as chronic atrophic gastritis, peptic ulcers, stomach or gastric cancer and the mucosa associated lymphoid tissue (MALT) lymphoma (Nomura et al., 1994; Forman, 1996; Parsonnet et al., 1991; Blaser et al., 1995). *H. pylori* is the main cause of gastric cancer—the third most common type of cancer with 983.000 cases worldwide in 2011 (Jemal et al., 2011).

Gastric cancer is associated with considerable socio-economic costs. Treating a single patient with gastric cancer currently costs about EUR 50.000. Prevention of gastric cancer includes early treatment of infection caused by *H. pylori*. According to estimates, at least one third of individuals with an infection caused by *H. pylori* require treatment. At present, it is difficult to predict which patients will develop the subsequent diseases associated with an *H. pylori* infection. Based on the results of numerous studies, general treatment of the *H. pylori* infection to prevent gastric carcinoma is cost efficient, as it would prevent over 95% of cases (Graham & Shiotani, 2005). Therapy is clearly indicated for patients with gastric ulcers, precancerous or definitive gastric cancer, relatives of gastric cancer patients, as well as patients requiring long-term therapy with non-steroidal anti-inflammatory drugs (including aspirin for cardiovascular diseases). Due to high gastric cancer rates in Japan, the treatment of all individuals infected with *H. pylori* is recommended there, despite steadily increasing antibiotic resistance rates (Shiota et al., 2010).

The standard therapy of infections caused by *H. pylori* to date consists of two antibiotics combined with a proton pump inhibitor such as omeprazole. The cost of a one-week treatment is approximately EUR 200 per patient. This therapy has significant side effects in some patients and leads to a steep increase in resistant pathogens. Because second- and third-line therapies often fail, about 10% of all patients can no longer be treated today (Gao et al., 2010), which could rise to an estimated 60% by 2020.

Furthermore, an increasing number of *Helicobacter* species (other than *H. pylori*) that colonize the enterohepatic tract of animals and humans have been identified in recent years and suggested to be involved in various diseases (Fox, 2002). For example, *H. bilis* has been associated with diseases such as cholecystitis, gallbladder cancer and biliary tract malignancies (Fox et al., 1998; Matsukura et al., 2002; Pisani et al., 2008).

Thus, there is a need for novel therapeutic approaches for preventing or treating diseases or disorders caused by or associated with *Helicobacter*, e.g., *H. pylori* or *H. bilis*. For example, if a vaccine against *H. pylori* were available, it would benefit millions of patients and reduce healthcare costs significantly. Vaccines are highly effective in combating prevalent infectious diseases. In fact, the U.S. Center of Disease Control called vaccination the most effective method for preventing infectious diseases (U.S. CDC, 2011). However, to date, there is no effective vaccine for humans against *H. pylori* available. When designing a vaccine, target screening and selection is detrimental to successfully achieving pan protection (Gómez-Gascón et al., 2012). Optimal antigens for vaccination should not only be conserved but also be essential for colonization, maintenance of infection, or pathogenicity. Therefore, antigens which enable direct interaction of bacteria with its host could provide preferred targets for vaccination and therapy in general.

SUMMARY OF THE INVENTION

In one aspect, the present invention relates to an inhibitor of the interaction between *Helicobacter pylori* HopQ and a member of the carcinoembryonic antigen-related cell adhesion molecule (CEACAM) family for use in a method of preventing or treating a disease or disorder caused by or associated with *H. pylori.*

In one embodiment, the inhibitor inhibits binding of *H. pylori* HopQ to the member of the CEACAM family and/or HopQ-CEACAM-mediated signaling.

In one embodiment, the inhibitor inhibits binding of *H. pylori* HopQ to the member of the CEACAM family, preferably to an extracellular domain of the member of the CEACAM family, more preferably to the N-domain of the member of the CEACAM family.

In one embodiment, the member of the CEACAM family is expressed on the surface of epithelial cells, endothelial cells and/or immune cells.

In one embodiment, the member of the CEACAM family is selected from the group consisting of human CEACAM family members, non-human primate CEACAM family members and rat CEACAM family members.

In one embodiment, the member of the CEACAM family is selected from the group consisting of CEACAM1, CEACAM3, CEACAM5 and CEACAM6.

In one embodiment, *H. pylori* HopQ is a type I HopQ protein or a type II HopQ protein.

In one embodiment, the inhibitor is selected from the group consisting of (a) (poly-)peptide ligands or peptidomimetic ligands binding to *H. pylori* HopQ, preferably to an extracellular domain of *H. pylori* HopQ;

(b) (poly-)peptide ligands or peptidomimetic ligands binding to the member of the CEACAM family, preferably to an extracellular domain of the member of the CEACAM family, more preferably to the N-domain of the member of the CEACAM family;

(c) nucleic acid molecules encoding the (poly-)peptide ligands of (a) and (b);

(d) nucleic acid ligands binding to *H. pylori* HopQ, preferably to an extracellular domain of *H. pylori* HopQ;

(e) nucleic acid ligands binding to the member of the CEACAM family, preferably to an extracellular domain of the member of the CEACAM family, more preferably to the N-domain of the member of the CEACAM family;

(f) inhibitory nucleic acid molecules inhibiting the expression of the member of the CEACAM family or of *H. pylori* HopQ;

(g) small molecules binding to *H. pylori* HopQ, preferably to an extracellular domain of *H. pylori* HopQ; and (h) small molecules binding to the member of the CEACAM family, preferably to an extracellular domain of the member of the CEACAM family, more preferably to the N-domain of the member of the CEACAM family.

In one embodiment, the (poly-)peptide ligands are selected from the group consisting of antibodies, antibody derivatives, antibody mimetics, peptide aptamers and soluble fragments of the member of the CEACAM family or of *H. pylori* HopQ.

In one embodiment, the peptidomimetic ligands are selected from the group consisting of peptoids, beta-peptides and D-peptides.

In one embodiment, the nucleic acid ligands are selected from the group consisting of DNA aptamers, RNA aptamers and XNA aptamers.

In one embodiment, the inhibitory nucleic acid molecules are selected from the group consisting of siRNAs, shRNAs, miRNAs and antisense DNA or RNA molecules.

In one embodiment, the extracellular domain of *H. pylori* HopQ is the insertion domain of *H. pylori* HopQ.

In one embodiment, the extracellular domain of *H. pylori* HopQ is loop A, loop B, loop C or loop D of *H. pylori* HopQ, wherein loop A is located between helix H3 and strand S1 of *H. pylori* HopQ;

loop B is located between strand S2 and helix H4 of *H. pylori* HopQ;

loop C is located between helix H5 and helix H6 of *H. pylori* HopQ; and loop D is located between helix H7 and helix H8 of *H. pylori* HopQ.

In one embodiment, the inhibitor is comprised in a pharmaceutical composition.

In one embodiment, the disease or disorder caused by or associated with *H. pylori* is selected from the group consisting of *H. pylori* infection and gastroduodenal disorders caused by *H. pylori.*

In one embodiment, the gastroduodenal disorders caused by *H. pylori* are selected from the group consisting of gastritis, chronic gastritis, gastric atrophy, gastric or duodenal ulcer, stomach cancer and MALT lymphoma.

In another aspect, the present invention relates to an in vitro method for identifying a drug candidate for preventing or treating a disease or disorder caused by or associated with *H. pylori*, the method comprising (a) contacting (i) a CEACAM protein or a functional fragment thereof with (ii) a *H. pylori* HopQ protein or a functional fragment thereof and (iii) a test compound, and (b) determining whether the test compound inhibits the interaction between the CEACAM protein or the functional fragment thereof and the *H. pylori* HopQ protein or the functional fragment thereof, wherein a test compound inhibiting the interaction between the CEACAM protein or the functional fragment thereof and the *H. pylori* HopQ protein or the functional fragment thereof is identified as a drug candidate for preventing or treating a disease or disorder caused by or associated with *H. pylori.*

In one embodiment, step (b) comprises determining whether the test compound inhibits binding of the *H. pylori* HopQ protein or the functional fragment thereof to the CEACAM protein or the functional fragment thereof, wherein, preferably, the functional fragment of the *H. pylori* HopQ protein comprises an extracellular domain or a fragment thereof, and/or the functional fragment of the CEACAM protein comprises an extracellular domain or a fragment thereof, preferably the N-domain, and/or determining whether the test compound inhibits HopQ-CEACAM-mediated signaling.

In one embodiment, the CEACAM protein is selected from the group consisting of human CEACAM proteins, non-human primate CEACAM proteins and rat CEACAM proteins.

In one embodiment, the CEACAM protein is selected from the group consisting of CEACAM1, CEACAM3, CEACAM5 and CEACAM6.

In one embodiment, the *H. pylori* HopQ protein is a type I HopQ protein or a type II HopQ protein.

In one embodiment, the extracellular domain of *H. pylori* HopQ is the insertion domain of *H. pylori* HopQ or a functional fragment thereof.

In one embodiment, the extracellular domain of *H. pylori* HopQ is loop A, loop B, loop C or loop D of *H. pylori* HopQ or a functional fragment of any of the foregoing, wherein loop A is located between helix H3 and strand S1 of *H. pylori* HopQ;

loop B is located between strand S2 and helix H4 of *H. pylori* HopQ;

loop C is located between helix H5 and helix H6 of *H. pylori* HopQ; and loop D is located between helix H7 and helix H8 of *H. pylori* HopQ.

In one embodiment, the extracellular domain of *H. pylori* HopQ is loop A, loop B or loop C of *H. pylori* HopQ or a functional fragment of any of the foregoing.

In one embodiment, the test compound is selected from the group consisting of (poly-)peptides, peptidomimetics, nucleic acid molecules and small molecules.

In another aspect, the present invention relates to the use of a CEACAM protein or a functional fragment thereof being able to interact with *H. pylori* HopQ for studying *H. pylori* infection or identifying a drug candidate for preventing or treating a disease or disorder caused by or associated with *H. pylori.*

In a further aspect, the present invention relates to the use of a cell heterologously expressing a CEACAM protein or a functional fragment thereof being able to interact with *H. pylori* HopQ for studying *H. pylori* infection or identifying a drug candidate for preventing or treating a disease or disorder caused by or associated with *H. pylori.*

In yet another aspect, the present invention relates to the use of a non-human transgenic animal heterologously expressing a CEACAM protein or a functional fragment thereof being able to interact with *H. pylori* HopQ for studying *H. pylori* infection or identifying a drug candidate for preventing or treating a disease or disorder caused by or associated with *H. pylori*.

In one embodiment of the above uses, the CEACAM protein is selected from the group consisting of human CEACAM proteins, non-human primate CEACAM proteins and rat CEACAM proteins.

In one embodiment, the CEACAM protein is selected from the group consisting of CEACAM1, CEACAM3, CEACAM5 and CEACAM6.

In one embodiment of the above method or uses, the disease or disorder caused by or associated with *H. pylori* is selected from the group consisting of *H. pylori* infection and gastroduodenal disorders caused by *H. pylori*.

In one embodiment, the gastroduodenal disorders caused by *H. pylori* are selected from the group consisting of gastritis, chronic gastritis, gastric atrophy, gastric or duodenal ulcer, stomach cancer and MALT lymphoma.

In another aspect, the present invention relates to an inhibitor of the interaction between *H. pylori* HopQ and a member of the carcinoembryonic antigen-related cell adhesion molecule (CEACAM) family, wherein the inhibitor is selected from the group consisting of (a) (poly-)peptide ligands or peptidomimetic ligands binding to an extracellular domain of *H. pylori* HopQ;

(b) (poly-)peptide ligands or peptidomimetic ligands binding to the N-domain of the member of the CEACAM family;

(c) nucleic acid molecules encoding the (poly-)peptide ligands of (a) and (b);

(d) nucleic acid ligands binding to an extracellular domain of *H. pylori* HopQ;

(e) nucleic acid ligands binding to the N-domain of the member of the CEACAM family;

(f) inhibitory nucleic acid molecules inhibiting the expression of the member of the CEACAM family or of *H. pylori* HopQ;

(g) small molecules binding to an extracellular domain of *H. pylori* HopQ; and (h) small molecules binding to the N-domain of the member of the CEACAM family.

In one embodiment, the (poly-)peptide ligands are selected from the group consisting of antibodies, antibody derivatives, antibody mimetics, peptide aptamers and soluble fragments of the member of the CEACAM family or of *H. pylori* HopQ.

In one embodiment, the peptidomimetic ligands are selected from the group consisting of peptoids, beta-peptides and D-peptides.

In one embodiment, the nucleic acid ligands are selected from the group consisting of DNA aptamers, RNA aptamers and XNA aptamers.

In one embodiment, the inhibitory nucleic acid molecules are selected from the group consisting of siRNAs, shRNAs, miRNAs and antisense DNA or RNA molecules.

In one embodiment, the extracellular domain of *H. pylori* HopQ is the insertion domain of *H. pylori* HopQ.

In one embodiment, the extracellular domain of *H. pylori* HopQ is loop A, loop B, loop C or loop D of *H. pylori* HopQ, wherein loop A is located between helix H3 and strand S1 of *H. pylori* HopQ;

loop B is located between strand S2 and helix H4 of *H. pylori* HopQ;

loop C is located between helix H5 and helix H6 of *H. pylori* HopQ; and loop D is located between helix H7 and helix H8 of *H. pylori* HopQ.

In one embodiment, the (poly-)peptide ligands or peptidomimetic ligands are selected from soluble fragments of the member of the CEACAM family or of *H. pylori* HopQ and peptidomimetic variants thereof, respectively.

In one embodiment, the soluble fragments of *H. pylori* HopQ comprise the insertion domain of *H. pylori* HopQ or a functional fragment thereof.

In one embodiment, the soluble fragments of *H. pylori* HopQ comprise loop A, loop B, loop C or loop D of *H. pylori* HopQ or a functional fragment of any of the foregoing, wherein loop A is located between helix H3 and strand S1 of *H. pylori* HopQ;

loop B is located between strand S2 and helix H4 of *H. pylori* HopQ;

loop C is located between helix H5 and helix H6 of *H. pylori* HopQ; and loop D is located between helix H7 and helix H8 of *H. pylori* HopQ.

In one embodiment, the member of the CEACAM family is selected from the group consisting of human CEACAM family members, non-human primate CEACAM family members and rat CEACAM family members.

In one embodiment, the member of the CEACAM family is selected from the group consisting of CEACAM1, CEACAM3, CEACAM5 and CEACAM6.

In yet another aspect, the present invention relates to an immunogenic composition comprising (a) at least one isolated (poly-)peptide comprising (i) the amino acid sequence of *H. pylori* HopQ; or (ii) an immunogenic variant thereof; or (iii) an immunogenic fragment of (i) or (ii); or (b) at least one nucleic acid molecule encoding an isolated (poly-)peptide according to item (a).

In one embodiment, the isolated (poly-)peptide is a recombinant (poly-)peptide.

In one embodiment, the immunogenic fragment comprises an extracellular domain of *H. pylori* HopQ.

In one embodiment, the extracellular domain of *H. pylori* HopQ is the insertion domain of *H. pylori* HopQ or a functional fragment thereof.

In one embodiment, the extracellular domain of *H. pylori* HopQ is loop A, loop B, loop C or loop D of *H. pylori* HopQ or a functional fragment of any of the foregoing, wherein loop A is located between helix H3 and strand S1 of *H. pylori* HopQ;

loop B is located between strand S2 and helix H4 of *H. pylori* HopQ;

loop C is located between helix H5 and helix H6 of *H. pylori* HopQ; and loop D is located between helix H7 and helix H8 of *H. pylori* HopQ.

In one embodiment, the isolated (poly-)peptide is a fusion protein.

In one embodiment, the nucleic acid molecule is DNA or RNA, wherein, preferably, the nucleic acid molecule is contained in a vector.

In one embodiment, the immunogenic composition further comprises at least one adjuvant.

In one embodiment, the immunogenic composition is a vaccine.

In one embodiment, the immunogenic composition elicits an immune response comprising the secretion of antibodies, wherein, preferably, the antibodies inhibit the interaction between *H. pylori* HopQ and a member of the carcinoembryonic antigen-related cell adhesion molecule (CEACAM) family.

In a further aspect, the present invention relates to an immunogenic composition as defined above for use as a medicament.

In yet another aspect, the present invention relates to an immunogenic composition as defined above for use in a method of preventing or treating a disease or disorder caused by or associated with *H. pylori*, wherein, preferably, the disease or disorder is selected from the group consisting of *H. pylori* infection and gastroduodenal disorders caused by *H. pylori*.

In one embodiment, the gastroduodenal disorders are selected from the group consisting of gastritis, chronic gastritis, gastric or duodenal ulcer, stomach cancer and MALT lymphoma.

In another aspect, the present invention relates to a CEACAM protein or a functional fragment thereof being able to interact with *H. pylori* HopQ for use in a method of preventing or treating a disease or disorder caused by or associated with *H. pylori*, wherein the CEACAM protein or functional fragment thereof is attached to a solid support, preferably a non-cellular solid support.

In one embodiment, the disease or disorder is selected from the group consisting of *H. pylori* infection and gastroduodenal disorders caused by *H. pylori*, wherein, preferably, the gastroduodenal disorders are selected from the group consisting of gastritis, chronic gastritis, gastric or duodenal ulcer, stomach cancer and MALT lymphoma.

In one embodiment, the CEACAM protein is selected from the group consisting of CEACAM1, CEACAM3, CEACAM5 and CEACAM6.

In one embodiment, the solid support is a microsphere.

DESCRIPTION OF THE FIGURES

FIG. 8*d*), which houses the adhesin's carbohydrate binding site, $HopQ^{AD}$ holds a beta-hairpin insertion domain (HopQ-ID) between helices H4 and H5. (b) Mean ELISA titers (n=4; ±s.d.) of $HopQ^{AD}$ or mutant $HopQ^{AD}$ lacking the HopQ-ID ($HopQ^{AD}\Delta$ID) binding to increasing concentrations of C1ND. Loss of the HopQ-ID results in a ~10-fold reduction in binding affinity. (c) SDS and native page of C1ND stained with Coomassie-blue ("C") or with $HopQ^{AD}$ in a far western blot ("HopQ") experiment. SDS and native-PAGE shows three glycosylation forms of C1ND in addition to the non-glycosylated protein (lower band). $HopQ^{AD}$ selectively binds the C1ND under non-denaturing conditions, demonstrating the implication of a strong protein-protein component in the HopQ-CEACAM interaction.

DETAILED DESCRIPTION OF THE INVENTION

Figure 1:
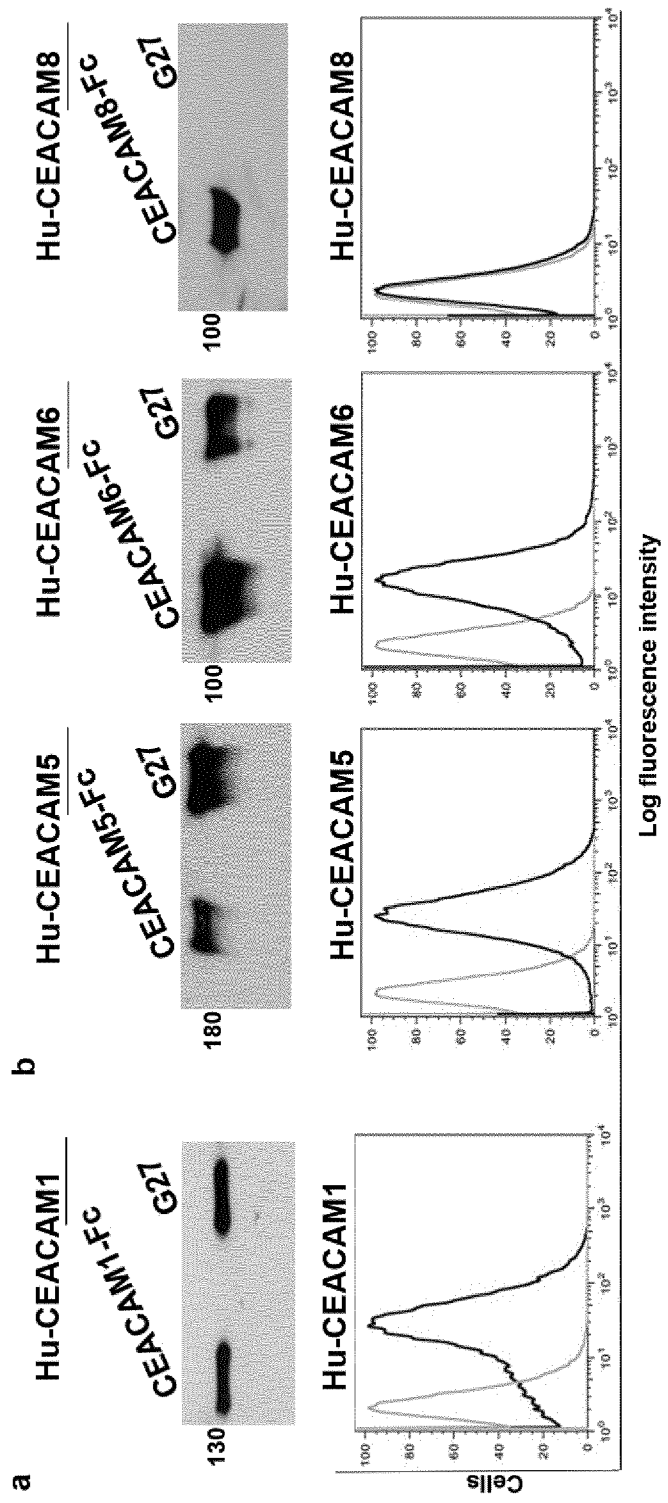
FIG. 1 shows that *H. pylori* employs the N-terminal domain of hu-CEACAM1 and binds CEACAM5 and CEACAM6 but not CEACAM8. Pull down experiments of live *H. pylori* and (a) hu-CEACAM1-Fc and (b) hu-CEACAM5-Fc, hu-CEACAM6-Fc or hu-CEACAM8-Fc, respectively, were analyzed by western blot and flow cytometry (n=3). (c) IHC staining of human normal stomach, gastritis and gastric cancer for CEACAM1, CEACAM5 and CEACAM6. Scale bars, 50 μm. (d) hu-CEACAM1ΔN-Fc was detected by western blot or cells were stained with α-hu-IgG-FITC and the fluorescence intensity of bacteria was analyzed by flow cytometry. (e) *H. pylori* incubated with GFP-tagged CEACAM1 variants analyzed by flow cytometry and the ratio of CEACAM variants binding to bacteria was measured. One-way ANOVA, P value=0.009, n. s.: not significant. Error bars indicate s.e.m. (f) Pull down experiments of *H. pylori* strains incubated with de-glycosylated hu-CEACAM1-Fc.
Figure 1:
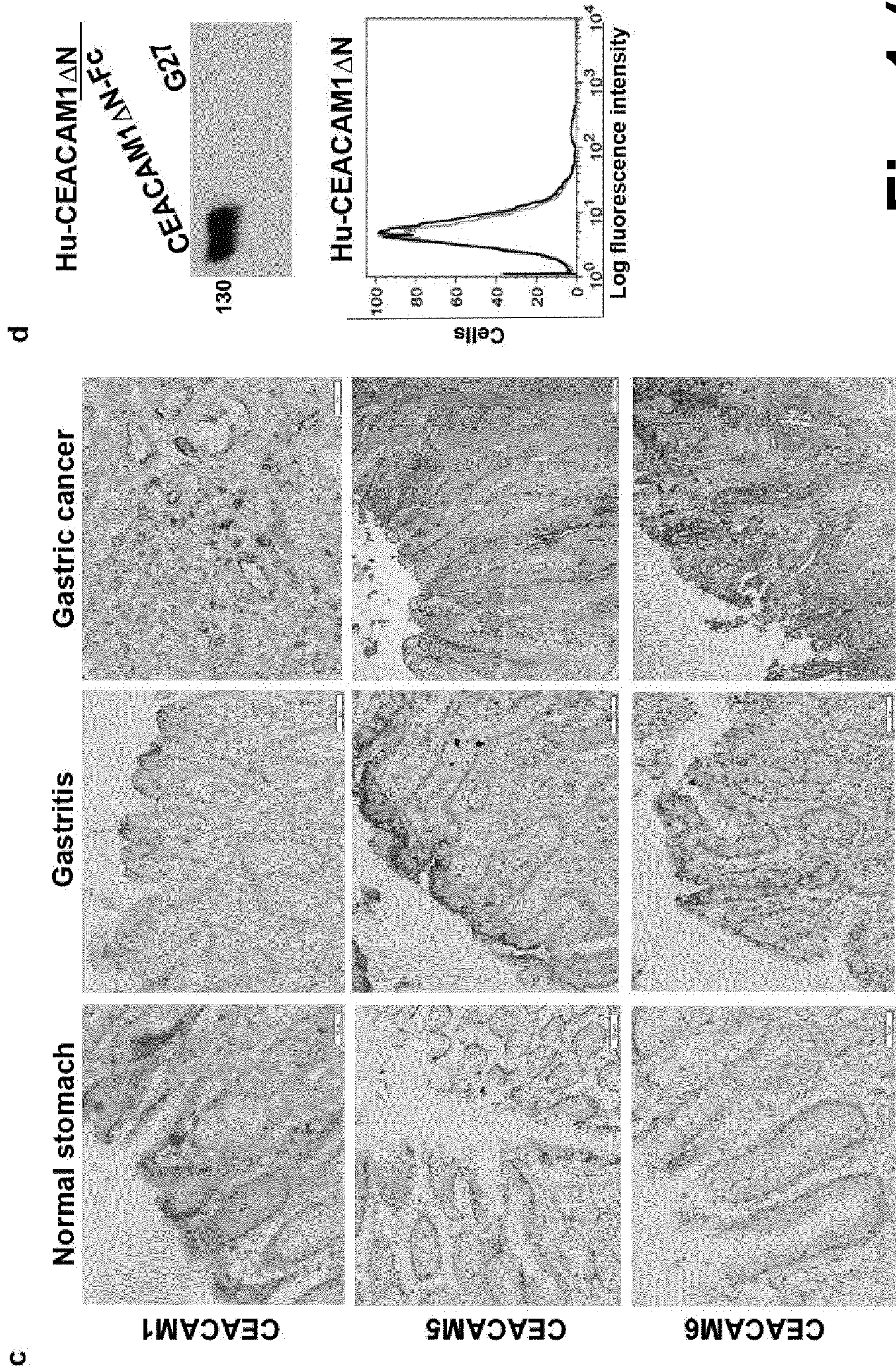
Figure 1:
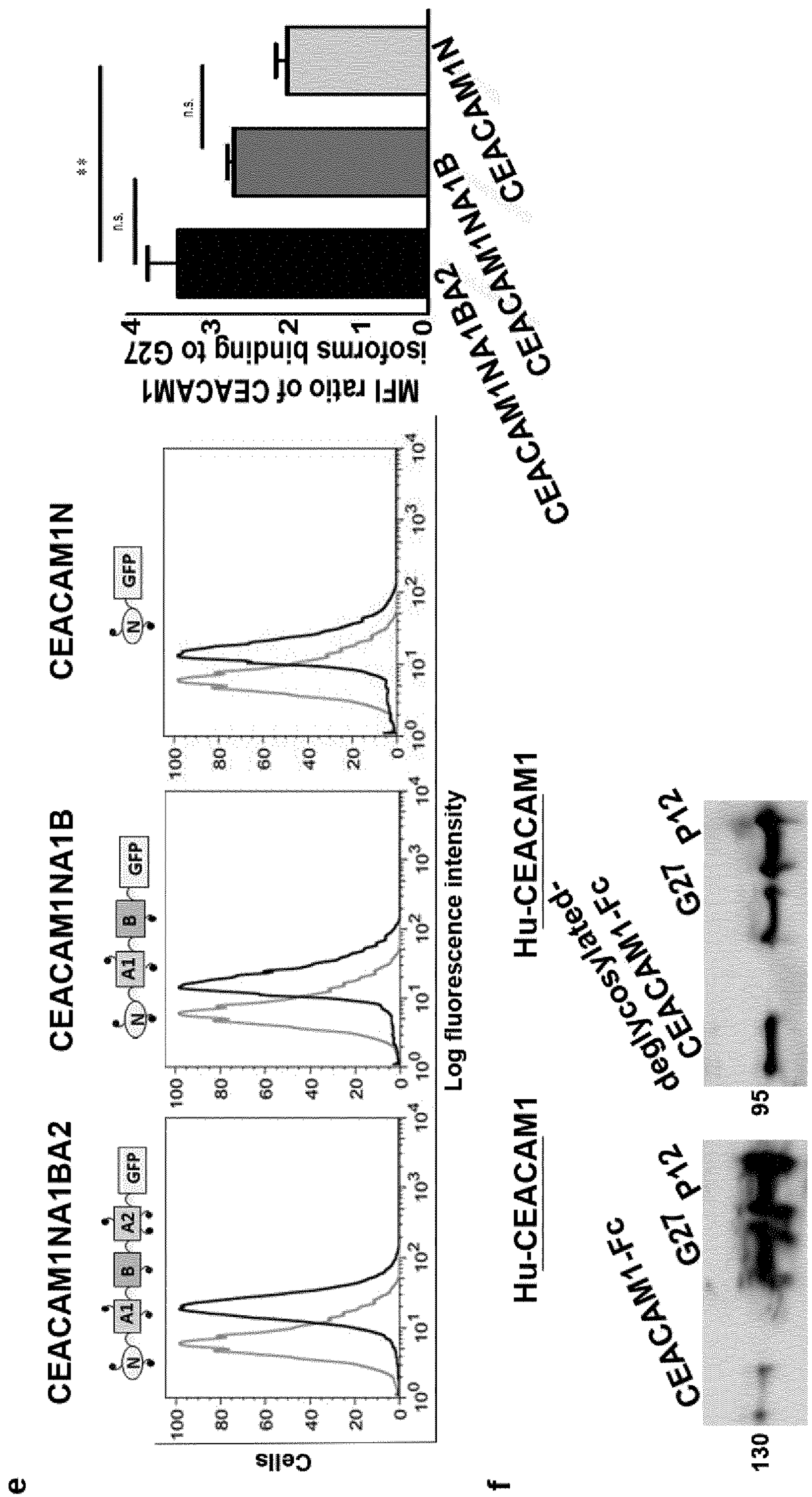

Although the present invention is described in detail above and below, it is to be understood that this invention is not limited to the particular methodologies, protocols and reagents described herein as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art.

In the following, certain elements of the present invention will be described. These elements may be listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments, which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 3rd Edition, J. Sambrook et al. eds., Cold Spring Harbor Laboratory Press, Cold Spring Harbor 2000).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

*H. pylori* specifically colonizes the human gastric epithelium and is the major causative agent for ulcer disease and gastric cancer development. The inventors have identified members of the carcinoembryonic antigen-related cell adhesion molecule (CEACAM) family as important receptors of all human *H. pylori* isolates and show that HopQ is a novel surface-exposed adhesin that specifically binds human CEACAM1, CEACAM3, CEACAM5 and CEACAM6. *H. pylori* binding to the CEACAM1 N-domain induces CEACAM1-mediated signaling, and the HopQ-CEACAM1 interaction enables translocation of the virulence factor CagA into host cells, permits colonization in the rat infection model and enhances the release of pro-inflammatory mediators such as interleukin-8. Based on the crystal structures of HopQ and a HopQ-CEACAM complex, the inventors have found that a beta-hairpin insertion domain in HopQ's extracellular 3+4 helix bundle domain and four specific loop regions are implicated in CEACAM binding. A peptide derived from the insertion domain competitively inhibits HopQ-mediated activation of the CagA virulence pathway, as does genetic or antibody-mediated abrogation of HopQ function. Together, the present invention identifies the HopQ-CEACAM interaction as novel therapeutic target to combat *H. pylori* associated diseases.

The present invention provides an inhibitor of the interaction between *H. pylori* HopQ and a member of the carcinoembryonic antigen-related cell adhesion molecule (CEACAM) family for use in a method of preventing or treating a disease or disorder caused by or associated with *H. pylori*.

The present invention further provides the use of an inhibitor of the interaction between *H. pylori* HopQ and a member of the CEACAM family in the preparation of a medicament for preventing or treating a disease or disorder caused by or associated with *H. pylori*.

The present invention further provides a method of preventing or treating a disease or disorder caused by or associated with *H. pylori* in a subject, said method comprising administering an inhibitor of the interaction between *H. pylori* HopQ and a member of the CEACAM family to the subject.

According to the present invention, a disease or disorder caused by or associated with *H. pylori* is preferably selected from the group consisting of *H. pylori* infection and gastroduodenal disorders caused by *H. pylori*.

The term "infection", as used herein, refers to the invasion of a subject's body tissues by disease-causing agents (e.g., *H. pylori*), their multiplication, and the reaction of the tissues to these agents and the toxins they produce.

The term "gastroduodenal disorder" (or simply "stomach disorder"), as used herein, refers to a disorder affecting the stomach and the adjoining duodenum. "Gastroduodenal disorders caused by *H. pylori*" are known to a person skilled in the art and include, for example, gastritis, chronic gastritis, gastric atrophy, gastric or duodenal ulcer, stomach cancer (also referred to as gastric cancer) and MALT lymphoma.

The term "subject", as used herein, relates to any organism such as a vertebrate, particularly any mammal, including both a human and another mammal, e.g., an animal such as a rodent, a rabbit, a cow, a sheep, a horse, a dog, a cat, a lama, a pig, or a non-human primate (e.g., a monkey). The rodent may be a mouse, rat, hamster, guinea pig, or chinchilla. In one embodiment, the subject is a human, a rat or a non-human primate. Preferably, the subject is a human. In one embodiment, a subject is a subject with or suspected of having a disease or disorder, in particular a disease or disorder as disclosed herein, also designated "patient" herein.

The term "preventing", as used herein, may refer to stopping/inhibiting the onset of a disease or disorder (e.g., by prophylactic treatment). It may also refer to a delay of the onset, reduced frequency of symptoms, or reduced severity of symptoms associated with the disease or disorder (e.g., by prophylactic treatment).

The term "treating", as used herein, relates to any treatment which improves the health status and/or prolongs (increases) the lifespan of a patient.

The term "medicament", as used herein, refers to a substance/composition used in therapy, i.e., in the prevention or treatment of a disease or disorder. According to the invention, the terms "disease" or "disorder" refer to any pathological state, in particular to the diseases or disorders as defined herein.

The carcinoembryonic antigen-related cell adhesion molecule (CEACAM) family is a well-known family of immunoglobulin-related vertebrate glycoproteins (see, for example, Tchoupa et al., 2014). Members of the CEACAM family typically comprise an N-terminal extracellular Igv-like domain, which may be followed by up to six extracellular $Ig_{C2}$-like domains, and are anchored in the cell membrane via a C-terminal transmembrane domain (TM helix) or a C-terminal GPI-anchor. The $Ig_v$-like domain is also referred to as N-terminal domain or N-domain. For example, human CEACAM1 comprises an N-domain followed by three (A1, B, A2) $Igc_2$-like domains. In one embodiment, the N-domain of human CEACAM1 comprises, essentially consists of or consists of amino acid residues 35 to 142 of human CEACAM1.

According to the present invention, the member of the CEACAM family is preferably expressed on the surface of epithelial cells, endothelial cells and/or immune cells (in particular leukocytes, such as T cells, B cells and neutrophils). In one embodiment, the member of the CEACAM family is expressed on the surface of epithelial cells (e.g., gastric epithelial cells), preferably at the apical side of epithelial cells.

According to the present invention, the member of the CEACAM family is preferably selected from the group consisting of human CEACAM family members, non-human primate CEACAM family members and rat CEACAM family members. In one embodiment, the member of the CEACAM family is a member of the human CEACAM family. In one embodiment, the member of the CEACAM family is not CEACAM 8. In one embodiment, the member of the CEACAM family is not CEACAM4, CEACAM7 and CEACAM8. In one embodiment, the member of the CEACAM family is selected from the group consisting of CEACAM1, CEACAM3, CEACAM5 and CEACAM6. In one embodiment, the member of the CEACAM family is selected from the group consisting of CEACAM1, CEACAM5 and CEACAM6. In one embodiment, the member of the CEACAM family is CEACAM1. The UniProt ID of human CEACAM1 is P13688. The UniProt ID of human CEACAM3 is P40198. The UniProt ID of human CEACAM5 is P06731. The UniProt ID of human CEACAM6 is P40199.

The terms "*H. pylori* HopQ" and "HopQ" are used interchangeably herein. HopQ is a member of a *H. pylori*-specific, paralogous family of outer membrane proteins. *H. pylori* hopQ (omp27; HP1177 in the *H. pylori* reference strain 26695) exhibits genetic diversity that represents two allelic families, type I and type IL According to the present invention, the term "*H. pylori* HopQ" encompasses both type I and type II HopQ proteins. In one embodiment, *H. pylori* HopQ is a type I HopQ protein or a type II HopQ protein. In one embodiment, the type I HopQ protein has the amino acid sequence of SEQ ID NO: 1 or SEQ ID NO: 3 or SEQ ID NO: 15 or an amino acid sequence which is at least 70%, 75%, 80%, 85%, 90%, 95%, 96%, 97%, 98% or 99% similar, preferably identical, to the amino acid sequence of SEQ ID NO: 1 or SEQ ID NO: 3 or SEQ ID NO: 15. In one embodiment, the type II HopQ protein has the amino acid sequence of SEQ ID NO: 5 or an amino acid sequence which is at least 70%, 75%, 80%, 85%, 90%, 95%, 96%, 97%, 98% or 99% similar, preferably identical, to the amino acid sequence of SEQ ID NO: 5.

"Sequence similarity" indicates the percentage of amino acids that either are identical or that represent conservative amino acid substitutions. "Sequence identity" between two amino acid sequences indicates the percentage of amino acids that are identical between the sequences. The alignment for determining sequence similarity, preferably sequence identity, can be done with art known tools, preferably using the best sequence alignment, for example, using CLC main Workbench (CLC bio) or Align, using standard settings, preferably EMBOSS::needle, Matrix: Blosum62, Gap Open 10.0, Gap Extend 0.5.

In one embodiment, the inhibitor inhibits binding of *H. pylori* HopQ to the member of the CEACAM family and/or HopQ-CEACAM-mediated signaling.

The term "HopQ-CEACAM-mediated signaling", as used herein, refers to activation of the CagA virulence pathway and/or phosphorylation of CagA and/or CagA translocation into cells (e.g., epithelial cells) and/or IL-8 induction and/or cell elongation. In one embodiment, HopQ-CEACAM-mediated signaling refers to CagA translocation into cells (e.g., epithelial cells), IL-8 induction and cell elongation. In one embodiment, HopQ-CEACAM-mediated signaling refers to CagA translocation into cells (e.g., epithelial cells).

In one embodiment, the inhibitor inhibits, e.g., competitively inhibits, binding of *H. pylori* HopQ to the member of the CEACAM family, preferably to an extracellular domain of the member of the CEACAM family.

The term "extracellular domain", as used herein, is meant to refer to those parts of a protein that are not cytosolic/cytoplasmic or embedded in the membrane, and includes parts located/exposed at the surface of the cell and/or in the periplasmic space. Such sequences/domains may be identified by using standard bioinformatic tools and/or public databases known to a person skilled in the art. In one embodiment, the extracellular domain further lacks the N-terminal secretion sequence.

In connection with a member of the CEACAM family, the term "extracellular domain" may refer to the entire extracellular part of said member, which, preferably, comprises the N-domain that, depending on the specific CEACAM family member, may be followed by one or more $Igc_2$-like domains. In one embodiment, the extracellular domain of the CEACAM family member comprises, essentially consists of or consists of the N-domain and 1, 2, 3, 4, 5 or 6 $Ig_{C2}$-like domain(s). In one embodiment, the extracellular domain of the CEACAM family member comprises, essentially consists of or consists of the N-domain. In one embodiment, the extracellular domain is the N-domain. The term "fragment" when used in connection with the extracellular domain of the CEACAM family member may refer to the N-domain and/or one or more $Ig_{C2}$-like domain(s). The term "fragment" may also refer to fragments of the N-domain and/or one or more $Ig_{C2}$-like domain(s), provided these fragments are able to interact with and/or bind to *H. pylori* HopQ (also referred to as HopQ-binding fragments).

In connection with *H. pylori* HopQ, the term "extracellular domain" may refer to the entire extracellular part of *H. pylori* HopQ, i.e., the full length protein lacking the C-terminal transmembrane domain. In one embodiment, the extracellular domain further lacks the N-terminal beta-strand and/or secretion sequence. In one embodiment, the extracellular domain corresponds to an amino acid sequence comprising, essentially consisting of or consisting of residues 37 to 463 of SEQ ID NO: 1. In one embodiment, the extracellular domain comprises, essentially consists of or consists of the insertion domain of *H. pylori* HopQ. In one embodiment, the extracellular domain is the insertion domain of *H. pylori* HopQ. In one embodiment, the extracellular domain of *H. pylori* HopQ comprises, essentially consists of, consists of or is loop A, loop B, loop C and/or loop D, preferably loop A, loop B and/or loop C, of *H. pylori* HopQ. The term "fragment" when used in connection with the extracellular domain of *H. pylori* HopQ preferably refers to fragments that are able to interact with and/or bind to the CEACAM family member (also referred to as CEACAM-binding fragments).

The term "insertion domain", as used herein, refers to the beta-hairpin insertion domain in *H. pylori* HopQ's extracellular 3+4 helix bundle domain, more particularly between helices H4 and H5, that is implicated in CEACAM binding. The insertion domain is herein also referred to as HopQ-ID. In one embodiment, the insertion domain corresponds to an amino acid sequence comprising, essentially consisting of or consisting of residues 210 to 238 of SEQ ID NO: 1.

The term "loop A", as used herein, refers to a loop located between helix H3 and strand S1 of *H. pylori* HopQ.

In one embodiment, loop A comprises, essentially consists of or consists of the amino acid sequence $CGGYX_{a5}X_{a6}X_{a7}PX_{a9}EX_{a11}X_{a12}QK$ (SEQ ID NO: 17), wherein $X_{a5}$ is an amino acid selected from the group consisting of T and Y or is deleted;

$X_{a6}$ is an amino acid selected from the group consisting of K and N or is deleted;

$X_{a7}$ is an amino acid selected from the group consisting of S, K, N and T or is deleted;

$X_{a9}$ is an amino acid selected from the group consisting of G, S, Q, R, T, I and V or is deleted;

$X_{a11}$ is an amino acid selected from the group consisting of N and G or is deleted; and $X_{a12}$ is an amino acid selected from the group consisting of N and H or is deleted.

In one embodiment, loop A comprises, essentially consists of or consists of the amino acid sequence of SEQ ID NO: 21. In one embodiment, loop A corresponds to an amino acid sequence comprising, essentially consisting of or consisting of residues 123 to 136 of SEQ ID NO: 15.

The term "loop B", as used herein, refers to a loop located between strand S2 and helix H4 of *H. pylori* HopQ.

In one embodiment, loop B comprises, essentially consists of or consists of the amino acid sequence $CGGX_{b4}X_{b5}X_{b6}X_{b7}X_{b8}GX_{b10}X_{b11}X_{b12}X_{b13}X_{b14}X_{b15}GX_{b17}X_{b18}X_{b19}LX_{b21}AX_{b23}KX_{b25}X_{b26}SLSI$ (SEQ ID NO: 18), wherein $X_{b4}$ is an amino acid selected from the group consisting of S, G, N, T and F or is deleted;

$X_{b5}$ is an amino acid selected from the group consisting of T and I or is deleted;

$X_{b6}$ is an amino acid selected from the group consisting of N, G and K or is deleted;

$X_{b7}$ is an amino acid selected from the group consisting of S and A or is deleted;

$X_{b8}$ is an amino acid selected from the group consisting of N and D or is deleted;

$X_{b10}$ is an amino acid selected from the group consisting of Q, K and R or is deleted;

$X_{b11}$ is an amino acid selected from the group consisting of T, V and S or is deleted;

$X_{b12}$ is an amino acid selected from the group consisting of H, Q and Y or is deleted;

$X_{b13}$ is an amino acid selected from the group consisting of S and N or is deleted;

$X_{b14}$ is an amino acid selected from the group consisting of S, P and N or is deleted;

$X_{b15}$ is an amino acid selected from the group consisting of N and S or is deleted;

$X_{b17}$ is an amino acid selected from the group consisting of T and V;

$X_{b18}$ is an amino acid selected from the group consisting of N and S;

$X_{b19}$ is an amino acid selected from the group consisting of T, L and M or is deleted;

$X_{b21}$ is an amino acid selected from the group consisting of K and P or is deleted;

$X_{b23}$ is an amino acid selected from the group consisting of D, G and A or is deleted;

$X_{b25}$ is an amino acid selected from the group consisting of N and G or is deleted; and $X_{b26}$ is an amino acid selected from the group consisting of V and S or is deleted.

In one embodiment, loop B comprises, essentially consists of or consists of the amino acid sequence of SEQ ID NO: 22 or SEQ ID NO: 23. In one embodiment, loop B corresponds to an amino acid sequence comprising, essentially consisting of or consisting of residues 152 to 180 of SEQ ID NO: 15.

The term "loop C", as used herein, refers to a loop located between helix H5 and helix H6 of *H. pylori* HopQ.

In one embodiment, loop C comprises, essentially consists of or consists of the amino acid sequence $CPX_{c3}LIX_{c6}X_{c7}X_{c8}X_{c9}X_{c10}X_{c11}X_{c12}X_{c13}X_{c14}X_{c15}X_{c16}X_{c17}X_{c18}NX_{c20}PSWQX_{c25}X_{c26}X_{c27}X_{c28}X_{c29}KNX_{c32}C$ (SEQ ID NO: 19), wherein $X_{c3}$ is an amino acid selected from the group consisting of M, I and V or is deleted;

$X_{c6}$ is an amino acid selected from the group consisting of A and G or is deleted;

$X_{c7}$ is an amino acid selected from the group consisting of K and R or is deleted;

$X_{c8}$ is an amino acid selected from the group consisting of S and T or is deleted;

$X_{c9}$ is an amino acid selected from the group consisting of S and T or is deleted;

$X_{c10}$ is an amino acid selected from the group consisting of S, N and G or is deleted;

$X_{c11}$ is an amino acid selected from the group consisting of G, N, E, S and D or is deleted;

$X_{c12}$ is an amino acid selected from the group consisting of S, G and N or is deleted;

$X_{c13}$ is an amino acid selected from the group consisting of S, M, G, N and T or is deleted;

$X_{c14}$ is an amino acid selected from the group consisting of G, A, T, S, N and M or is deleted;

$X_{c15}$ is an amino acid selected from the group consisting of G, N, T, A and V or is deleted;

$X_{c16}$ is an amino acid selected from the group consisting of A, N, G and S or is deleted;

$X_{c17}$ is an amino acid selected from the group consisting of T, N, A, G and S or is deleted;

$X_{c18}$ is an amino acid selected from the group consisting of T and A or is deleted;

$X_{c20}$ is an amino acid selected from the group consisting of T and A or is deleted;

$X_{c25}$ is an amino acid selected from the group consisting of T and I or is deleted;

$X_{c26}$ is an amino acid selected from the group consisting of A, S, T and N or is deleted;

$X_{c27}$ is an amino acid selected from the group consisting of G and S or is deleted;

$X_{c28}$ is an amino acid selected from the group consisting of G and N or is deleted;

$X_{c29}$ is an amino acid selected from the group consisting of G, L and S or is deleted; and $X_{c32}$ is an amino acid selected from the group consisting of S and A or is deleted.

In one embodiment, loop C comprises, essentially consists of or consists of the amino acid sequence of SEQ ID NO: 24 or SEQ ID NO: 25. In one embodiment, loop C corresponds to an amino acid sequence comprising, essentially consisting of or consisting of residues 258 to 290 of SEQ ID NO: 15.

The term "functional fragment" when used in connection with loops A, B and/or C preferably refers to fragments that are able to interact with and/or bind to the CEACAM family member (also referred to as CEACAM-binding fragments).

The term "loop D", as used herein, refers to a loop located between helix H7 and helix H8 of *H. pylori* HopQ.

In one embodiment, loop D comprises, essentially consists of or consists of the amino acid sequence $SSX_{d3}X_{d4}LKX_{d7}YIX_{d10}KCDX_{d14}SX_{d16}X_{d17}SX_{d19}X_{d20}X_{d21}X_{d22}X_{d23}NMX_{d26}X_{d27}X_{d28}X_{d29}X_{d30}KX_{d32}X_{d33}X_{d34}WGX_{d37}GCAG$ (SEQ ID NO: 20), wherein $X_{d3}$ is an amino acid selected from the group consisting of G and D or is deleted;

$X_{d4}$ is an amino acid selected from the group consisting of H and Y or is deleted;

$X_{d7}$ is an amino acid selected from the group consisting of D and N or is deleted;

$X_{d10}$ is an amino acid selected from the group consisting of G and R or is deleted;

$X_{d14}$ is an amino acid selected from the group consisting of M, A and V or is deleted;

$X_{d16}$ is an amino acid selected from the group consisting of A and G or is deleted;

$X_{d17}$ is an amino acid selected from the group consisting of I and V or is deleted;

$X_{d19}$ is an amino acid selected from the group consisting of S and G or is deleted;

$X_{d20}$ is any amino acid or is deleted;

$X_{d21}$ is any amino acid or is deleted;

$X_{d22}$ is any amino acid or is deleted;

$X_{d23}$ is an amino acid selected from the group consisting of T, A and S or is deleted;

$X_{d26}$ is an amino acid selected from the group consisting of T and A or is deleted;

$X_{d27}$ is an amino acid selected from the group consisting of M, P, A and Q or is deleted;

$X_{d28}$ is an amino acid selected from the group consisting of Q, R, K and H or is deleted;

$X_{d29}$ is an amino acid selected from the group consisting of S and N or is deleted;

$X_{d30}$ is an amino acid selected from the group consisting of Q and M or is deleted;

$X_{d32}$ is an amino acid selected from the group consisting of N and S or is deleted;

$X_{d33}$ is an amino acid selected from the group consisting of N and T or is deleted;

$X_{d34}$ is an amino acid selected from the group consisting of T, N and I or is deleted; and $X_{d37}$ is an amino acid selected from the group consisting of N and K or is deleted.

In one embodiment, loop D comprises, essentially consists of or consists of the amino acid sequence of SEQ ID NO: 26 or SEQ ID NO: 27. In one embodiment, loop D corresponds to an amino acid sequence comprising, essentially consisting of or consisting of residues 371 to 407 of SEQ ID NO: 15.

In one embodiment, the inhibitor is selected from the group consisting of (a) (poly-)peptide ligands or peptidomimetic ligands binding to *H. pylori* HopQ, preferably to an extracellular domain of *H. pylori* HopQ;

(b) (poly-)peptide ligands or peptidomimetic ligands binding to the member of the CEACAM family, preferably to an extracellular domain of the member of the CEACAM family, more preferably to the N-domain of the member of the CEACAM family;

(c) nucleic acid molecules encoding the (poly-)peptide ligands of (a) and (b);

(d) nucleic acid ligands binding to *H. pylori* HopQ, preferably to an extracellular domain of *H. pylori* HopQ;

(e) nucleic acid ligands binding to the member of the CEACAM family, preferably to an extracellular domain of the member of the CEACAM family, more preferably to the N-domain of the member of the CEACAM family;

(f) inhibitory nucleic acid molecules inhibiting the expression of the member of the CEACAM family or of *H. pylori* HopQ;

(g) small molecules binding to *H. pylori* HopQ, preferably to an extracellular domain of *H. pylori* HopQ; and (h) small molecules binding to the member of the CEACAM family, preferably to an extracellular domain of the member of the CEACAM family, more preferably to the N-domain of the member of the CEACAM family.

The term "(poly-)peptide ligand", as used herein, is meant to refer to a ligand of the member of the CEACAM family or a ligand of *H. pylori* HopQ, which is a (poly-)peptide, wherein the term "(poly-)peptide" refers to a molecule which is either a peptide or a polypeptide.

The term "peptide" generally relates to substances which include at least 2, at least 3, at least 4, at least 6, at least 8, at least 10, at least 12 or at least 14 and preferably up to 8, 10, 12, 14, 16, 18, 20, 25, 30, 50, or 100 consecutive amino acids which are connected together by peptide bonds. The terms "polypeptide" and "protein" relate to large peptides, preferably peptides having more than 100 amino acids, but the terms "peptide", "polypeptide" and "protein" are generally used interchangeably herein.

(Poly-)peptides according to the present invention are preferably isolated. The term "isolated (poly-)peptide" means that the (poly-)peptide is separated from its natural environment. An isolated (poly-)peptide may be in an essentially purified and/or pure state. The term "essentially purified" or "essentially pure" means that the (poly-)peptide is essentially free of other substances, e.g., substances with which it is present and/or associated in nature or in vivo, such as other proteins, nucleic acids, lipids and carbohydrates. In some embodiments, (poly-)peptides according to the present invention are (chemically) synthesized.

According to the present invention, the (poly-)peptide ligands are preferably selected from the group consisting of antibodies, antibody derivatives, antibody mimetics, peptide aptamers and soluble fragments of the member of the CEACAM family or of *H. pylori* HopQ.

The term "antibody" (also referred to as immunoglobulin, Ig) refers to a glycoprotein comprising at least two heavy (H) chains and two light (L) chains inter-connected by disulfide bonds. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antibody derivative", as used herein, refers to a molecule comprising at least one antibody variable domain, but not having the overall structure of an antibody such as IgA, IgD, IgE, IgG, IgM, IgY or IgW, although still being capable of binding a target molecule. Said derivatives may be, but are not limited to functional (i.e. target binding, particularly specifically target binding) antibody fragments, such as Fab, Fab2, scFv, Fv, or parts thereof, or other derivatives or combinations of the immunoglobulins such as nanobodies, diabodies, minibodies, camelid single domain antibodies, single domains or Fab fragments, domains of the heavy and light chains of the variable region (such as Fd, VL, including Vlambda and Vkappa, VH, VHH) as well as mini-domains consisting of two beta-strands of an immunoglobulin domain connected by at least two structural loops. Preferably, the antibody derivative is monovalent. More preferably, the derivative is a single chain antibody, most preferably having the structure VL-peptide linker-VH or VH-peptide linker-VL.

The term "antibody mimetic", as used herein, refers to artificial (poly-)peptides that, like antibodies, can specifically bind antigens, but that are not structurally related to antibodies. They are usually significantly smaller than antibodies with a molar mass of about 3 to 20 kDa. Non-limiting examples of antibody mimetics are affibodies, affitins, affimers, alphabodies, affitins, anticalins, avimers, DARPins, fynomers, Kunits domain peptides, monobodies, Z domain of Protein A, Gamma B crystalline, ubiquitin, cystatin, Sac7D from Sulfolobus acidocaldarius, lipocalin, A domain of a membrane receptor, ankyrin repeat motive, SH3 domain of Fyn, Kunits domain of protease inhibitors, the $10^{th}$ type III domain of fibronectin, 3- or 4-helix bundle proteins, an armadillo repeat domain, a leucine-rich repeat domain, a PDZ domain, a SUMO or SUMO-like domain, an immunoglobulin-like domain, phosphotyrosine-binding domain, pleckstrin homology domain, src homology 2 domain or synthetic peptide ligands, e.g., from a (random) peptide library. Synthetic peptide ligands have non-naturally occurring amino acid sequences that function to bind a particular target molecule.

Peptide aptamers are proteins that are designed to interfere with other protein interactions. They usually consist of a variable peptide loop attached at both ends to a protein scaffold. The variable loop length is typically composed of ten to twenty amino acids, and the scaffold may be any protein which has good solubility and compacity properties, e.g., thioredoxin-A. Also encompassed by the term "peptide aptamer", as used herein, are derivatives of peptide aptamers, such as affimer proteins.

The terms "part" or "fragment" are used interchangeably herein and refer to a continuous element. For example, a part of a structure, such as an amino acid sequence or protein, refers to a continuous element of said structure. A part or fragment of a protein sequence preferably comprises a sequence of at least 6, in particular at least 8, at least 12, at least 15, at least 20, at least 30, at least 50, at least 100, at least 150, at least 160, at least 170, at least 180, at least 190 or at least 200 consecutive amino acids of the protein sequence. According to the present invention, a part or fragment of a protein sequence does, preferably, not comprise continuous with the part or fragment further N- and/or C-terminal amino acid sequences of the protein sequence.

The term “soluble”, as used in connection with fragments of CEACAM family members or *H. pylori* HopQ, refers to (poly-)peptides that are predominantly soluble in an aqueous solution, such as water, PBS or cytosol (e.g., at pH 6-8). The term “predominantly soluble” means that a majority, e.g., >50% or >60% or >70% or >80% or >90%, of the (poly-) peptide molecules are in a soluble state in said aqueous solution. In one embodiment, such soluble fragments lack a transmembrane domain or a GPI-anchor.

In one embodiment, a soluble fragment of the CEACAM family member comprises, essentially consists of or consists of an extracellular domain of the CEACAM family member or a HopQ-binding fragment thereof. In one embodiment, the soluble fragment comprises, essentially consists of or consists of the N-domain or a HopQ-binding fragment thereof.

In one embodiment, a soluble fragment of *H. pylori* HopQ comprises, essentially consists of or consists of an extracellular domain of *H. pylori* HopQ or a CEACAM-binding fragment thereof. In one embodiment, the soluble fragment comprises, essentially consists of or consists of the insertion domain, loop A, loop B, loop C and/or loop D, preferably loop A, loop B and/or loop C, of *H. pylori* HopQ or a functional fragment of any of the foregoing.

Also encompassed by the present invention are peptidomimetic variants of the soluble fragments of the member of the CEACAM family or of *H. pylori* HopQ. Further encompassed are amino acid insertion variants, amino acid addition variants, amino acid deletion variants and/or amino acid substitution variants as described further below. Such variants are, according to the invention, functional variants which inhibit the interaction between *H. pylori* HopQ and of the member of the CEACAM family.

In one embodiment, the soluble fragment further comprises a detectable label or tag as described further below. In one embodiment, the soluble fragment further comprises one or more modifications increasing the stability and/or preventing aggregation of the soluble fragment, as described further below in connection with immunogenic fragments.

The term “peptidomimetic ligand”, as used herein, is meant to refer to a ligand of the member of the CEACAM family or a ligand of *H. pylori* HopQ, which is a peptidomimetic.

The term “peptidomimetic”, as used herein, refers to a compound which has essentially the same general structure of a corresponding (poly-)peptide with modifications that increase its stability and/or biological function. A peptidomimetic includes, for example, those compounds comprising the same amino acid sequence of a corresponding (poly-)peptide with an altered backbone between two or more of the amino acids. Alternatively or additionally, the peptidomimetic can comprise synthetic or non-naturally occurring amino acids in place of naturally-occurring amino acids. Exemplary peptidomimetics include peptoids, beta-peptides and D-peptides.

The term “peptidomimetic variant”, as used herein, is meant to refer to the peptidomimetic derivative of a given natural parent (poly-)peptide, e.g., of a soluble fragment of the member of the CEACAM family or of *H. pylori* HopQ.

The term “peptoid”, as used herein, refers to a peptidomimetic in which the sidechains of each amino acid is appended to the nitrogen atom of the amino acid as opposed to the alpha carbon. For example, peptoids can be considered as N-substituted glycines which have repeating units of the general structure of $NRCH_2CO$ and which have the same or substantially the same amino acid sequence as the corresponding polypeptide.

Beta-peptides consist of beta amino acids, which have their amino group bonded to the beta carbon rather than the alpha carbon as in the 20 standard biological amino acids. Beta-peptides are stable against proteolytic degradation in vitro and in vivo.

A D-peptide is a sequence of D-amino acids. Just as beta-peptides, D-peptides are less susceptible to be degraded in the stomach or inside cells by proteolysis.

A nucleic acid molecule may according to the invention be in the form of a molecule, which is single-stranded or double-stranded and linear or covalently closed to form a circle. In one embodiment, the nucleic acid molecule is DNA or RNA or XNA.

In the context of the present invention, the term “DNA” relates to a molecule, which comprises deoxyribonucleotide residues and preferably is entirely or substantially composed of deoxyribonucleotide residues. “Deoxyribonucleotide” relates to a nucleotide, which lacks a hydroxyl group at the 2'-position of a β-D-ribofuranosyl group. The term “DNA” comprises isolated DNA such as partially or completely purified DNA, essentially pure DNA, synthetic DNA, and recombinantly generated DNA and includes modified DNA, which differs from naturally occurring DNA by addition, deletion, substitution and/or alteration of one or more nucleotides. Such alterations can include addition of non-nucleotide material, such as to the end(s) of a DNA or internally, for example at one or more nucleotides of the DNA. Nucleotides in DNA molecules can also comprise non-standard nucleotides, such as non-naturally occurring nucleotides or chemically synthesized nucleotides. These altered DNAs can be referred to as analogs or analogs of naturally occurring DNA.

In the context of the present invention, the term “RNA” relates to a molecule, which comprises ribonucleotide residues and preferably is entirely or substantially composed of ribonucleotide residues. “Ribonucleotide” relates to a nucleotide with a hydroxyl group at the 2'-position of a β-D-ribofuranosyl group. The term “RNA” comprises isolated RNA such as partially or completely purified RNA, essentially pure RNA, synthetic RNA, and recombinantly generated RNA and includes modified RNA, which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally occurring RNA. According to the invention, “RNA” refers to single-stranded RNA or double stranded RNA. In one embodiment, the RNA is mRNA. In one embodiment, the RNA is in vitro transcribed RNA (IVT RNA) or synthetic RNA.

A xeno-nucleic acid (XNA) is a synthetic DNA/RNA analogue containing non-natural components such as alternative nucleobases, sugars, or a connecting backbone with a different chemical structure.

The term “nucleic acid ligand”, as used herein, is meant to refer to a ligand of the member of the CEACAM family or a ligand of *H. pylori* HopQ, which is a nucleic acid molecule, e.g., a nucleic acid aptamer.

Nucleic acid aptamers, i.e., RNA aptamers, DNA aptamers and XNA aptamers, are a class of small nucleic acid ligands that are composed of RNA or single-stranded DNA or XNA oligonucleotides and have high specificity and affinity for their targets. Similar to antibodies, aptamers interact with their targets by recognizing a specific three-dimensional structure.

The term "inhibitory nucleic acid molecule", as used herein, refers to a nucleic acid molecule which inhibits expression of a target molecule, e.g., a member of the CEACAM family or *H. pylori* HopQ. Exemplary inhibitory nucleic acid molecules include small interfering RNA (siRNA), small/short hairpin RNA (shRNA), microRNA (miRNA) and antisense DNA or RNA molecules, all of which are well-known to a person skilled in the art.

The term "small molecule", as used herein, refers to a low molecular weight (e.g., <900 Da or <500 Da) organic compound.

The term "binding" may in context of the present invention, e.g., in connection with the (poly-)peptide ligands, nucleic acid ligands or small molecules as defined herein, refer to specific binding. The terms "specific binding" or "specifically binding", as used herein, mean that a binding to a target, such as an epitope for which a binding agent, such as a (poly-)peptide ligand (e.g., an antibody), is specific, is stronger by comparison with the binding to another target. A "stronger binding" can be characterized for example by a lower dissociation constant ($K_D$). In one embodiment, a binding agent is specific for a predetermined target if it is capable of binding to said predetermined target while it is not capable of binding to other targets. In one embodiment, a binding agent that "specifically binds" a target has an $K_D$ value of less than $10^{-5}$ M (e.g., $10^{-6}$, $10^{-7}$, $10^{-8}$, $10^{-9}$, $10^{-10}$, $10^{-11}$, and $10^{-12}$ or less) for that target. The $K_D$ value of a given binding agent is influenced both by the on and off-rate of the binding agent and varies with the temperature. It is preferred in the context of the present invention that the $K_D$ value is below above indicated values at room temperature. The binding conditions are preferably physiological conditions. The skilled person is aware of various assays to determine the $K_D$ value. A preferred assay system is a competition assay.

In one embodiment, the (poly-)peptide ligands or peptidomimetic ligands or nucleic acid ligands or small molecules binding to *H. pylori* HopQ bind to an epitope of *H. pylori* HopQ comprising at least 1, 2, 3, 4, 5, 6, 7 or 8 amino acid residues comprised in the insertion domain, loop A, loop B, loop C and/or loop D, preferably loop A, loop B and/or loop C, of *H. pylori* HopQ.

In one embodiment, the inhibitor is comprised in a pharmaceutical composition. Accordingly, the present invention also provides a pharmaceutical composition comprising an inhibitor of the interaction between *H. pylori* HopQ and a member of the CEACAM family as defined herein.

The present invention further provides an in vitro method for identifying a drug candidate for preventing or treating a disease or disorder caused by or associated with *H. pylori*, the method comprising (a) contacting (i) a CEACAM protein or a functional fragment thereof with (ii) a *H. pylori* HopQ protein or a functional fragment thereof and (iii) a test compound, and (b) determining whether the test compound inhibits the interaction between the CEACAM protein or the functional fragment thereof and the *H. pylori* HopQ protein or the functional fragment thereof, wherein a test compound inhibiting the interaction between the CEACAM protein or the functional fragment thereof and the *H. pylori* HopQ protein or the functional fragment thereof is identified as a drug candidate for preventing or treating a disease or disorder caused by or associated with *H. pylori*.

In one embodiment, step (b) comprises determining whether the test compound inhibits binding of the *H. pylori* HopQ protein or the functional fragment thereof to the CEACAM protein or the functional fragment thereof, wherein, preferably, the functional fragment of the *H. pylori* HopQ protein comprises an extracellular domain or a fragment thereof, and/or the functional fragment of the CEACAM protein comprises an extracellular domain or a fragment thereof, preferably the N-domain, and/or determining whether the test compound inhibits HopQ-CEACAM-mediated signaling.

In one embodiment, the test compound is selected from the group consisting of (poly-)peptides, peptidomimetics, nucleic acid molecules and small molecules.

The present invention further provides the use of a CEACAM protein or a functional fragment thereof being able to interact with *H. pylori* HopQ for studying *H. pylori* infection or identifying a drug candidate for preventing or treating a disease or disorder caused by or associated with *H. pylori*.

The term "functional fragment", as used herein in connection with a CEACAM protein, may, for example, refer to an extracellular domain of the CEACAM protein or a fragment thereof.

The present invention further provides the use of a cell heterologously expressing a CEACAM protein or a functional fragment thereof being able to interact with *H. pylori* HopQ for studying *H. pylori* infection or identifying a drug candidate for preventing or treating a disease or disorder caused by or associated with *H. pylori*.

Such cell (also referred to as host cell) may either be a prokaryotic cell (e.g., a bacterial cell) or a eukaryotic cell (e.g., a fungal, plant or animal cell). In one embodiment, the cell is a mammalian cell, e.g., a CHO cell or HEK293 cell. Preferably, the cell is an isolated cell.

The present invention further provides the use of a non-human transgenic animal heterologously expressing a CEACAM protein or a functional fragment thereof being able to interact with *H. pylori* HopQ for studying *H. pylori* infection or identifying a drug candidate for preventing or treating a disease or disorder caused by or associated with *H. pylori*.

The term "non-human transgenic animal", as used herein, relates, in particular, to non-human mammals, e.g., a rodent, a rabbit, a cow, a sheep, a horse, a dog, a cat, a lama, a pig, or a non-human primate (e.g., a monkey). The rodent may be a mouse, rat, hamster, guinea pig, or chinchilla. In one embodiment, the non-human transgenic animal is a rat.

The present invention further provides an inhibitor of the interaction between *H. pylori* HopQ and a member of the carcinoembryonic antigen-related cell adhesion molecule (CEACAM) family, wherein the inhibitor is selected from the group consisting of (a) (poly-)peptide ligands or peptidomimetic ligands binding to an extracellular domain of *H. pylori* HopQ;

(b) (poly-)peptide ligands or peptidomimetic ligands binding to the N-domain of the member of the CEACAM family;

(c) nucleic acid molecules encoding the (poly-)peptide ligands of (a) and (b);

(d) nucleic acid ligands binding to an extracellular domain of *H. pylori* HopQ;

(e) nucleic acid ligands binding to the N-domain of the member of the CEACAM family;

(f) inhibitory nucleic acid molecules inhibiting the expression of the member of the CEACAM family or of *H. pylori* HopQ;

(g) small molecules binding to an extracellular domain of *H. pylori* HopQ; and (h) small molecules binding to the N-domain of the member of the CEACAM family.

In one embodiment, the extracellular domain of *H. pylori* HopQ is the insertion domain of *H. pylori* HopQ.

In one embodiment, the extracellular domain of *H. pylori* HopQ is loop A, loop B, loop C or loop D of *H. pylori* HopQ.

In one embodiment, the (poly-)peptide ligands or peptidomimetic ligands are selected from soluble fragments of the member of the CEACAM family or of *H. pylori* HopQ and peptidomimetic variants thereof, respectively.

In one embodiment, the soluble fragments of *H. pylori* HopQ comprise the insertion domain of *H. pylori* HopQ or a functional fragment thereof.

In one embodiment, the soluble fragments of *H. pylori* HopQ comprise loop A, loop B, loop C or loop D of *H. pylori* HopQ or a functional fragment of any of the foregoing.

The present invention also provides an immunogenic composition comprising (a) at least one, e.g., one, two, three, four or five or more, isolated (poly-)peptide comprising (i) the amino acid sequence of *H. pylori* HopQ; or (ii) an immunogenic variant thereof; or (iii) an immunogenic fragment of (i) or (ii); or (b) at least one, e.g., one, two, three, four or five or more, nucleic acid molecule encoding an isolated (poly-)peptide according to item (a).

The term "immunogenic", as used herein, is meant to refer to the ability to provoke an immune response, i.e., to induce a humoral and/or cell-mediated immune response, in a subject. A "humoral immune response" is mediated by macromolecules found in extracellular body fluids, such as secreted antibodies, complement proteins and certain antimicrobial peptides. A "cell-mediated immune response" involves the activation of phagocytes, antigen-specific T-lymphocytes and the release of various cytokines in response to an antigen. In one embodiment, the immune response is mediated by antibodies (=antibody response). The terms "immunogenic fragment" and "immunogenic variant", as used herein, preferably refer to fragments and variants, which are able to elicit an immune response that is specific to the (poly-)peptide the fragments and variants are derived from.

In one embodiment, the amino acid sequence of *H. pylori* HopQ is the amino acid sequence of SEQ ID NO: 1 or SEQ ID NO: 3 or SEQ ID NO: 5 or SEQ ID NO: 15 or an amino acid sequence which is at least 70%, 75%, 80%, 85%, 90%, 95%, 96%, 97%, 98% or 99% similar, preferably identical, to the amino acid sequence of SEQ ID NO: 1 or SEQ ID NO: 3 or SEQ ID NO: 5 or SEQ ID NO: 15.

In one embodiment, the immunogenic fragment comprises, essentially consists of or consists of an extracellular domain of *H. pylori* HopQ. In one embodiment, the immunogenic fragment comprises the insertion domain, loop A, loop B, loop C and/or loop D of *H. pylori* HopQ. In one embodiment, the immunogenic fragment lacks the N-terminal beta-strand and/or the N-terminal secretion sequence (=signal peptide) and/or the C-terminal transmembrane (TM) domain. In one embodiment, the immunogenic fragment lacks the N-terminal beta-strand and the N-terminal secretion sequence and the C-terminal TM domain. In one embodiment, the immunogenic fragment comprises, essentially consists of or consists of residues 37 to 463 of SEQ ID NO: 1.

In one embodiment, the extracellular domain of *H. pylori* HopQ is the insertion domain of *H. pylori* HopQ or a functional fragment thereof.

In one embodiment, the extracellular domain of *H. pylori* HopQ is loop A, loop B, loop C or loop D of *H. pylori* HopQ or a functional fragment of any of the foregoing.

The term "immunogenic variant" according to the invention refers, in particular, to immunogenic mutants, splice variants, conformation variants, isoforms, allelic variants, species variants and homologues, in particular those, which occur naturally. An allelic variant relates to an alteration in the normal sequence of a gene, the significance of which is often unclear. Complete gene sequencing often identifies numerous allelic variants for a given gene. A homologue is a nucleic acid or amino acid sequence with a different species (or strain) of origin from that of a given nucleic acid or amino acid sequence. The term "variant" shall encompass any posttranslationally modified variants and conformation variants.

For the purposes of the present invention, "immunogenic variants" of an amino acid sequence comprise immunogenic amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise N- and/or C-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein, for example at the N- and/or C-terminus.

Amino acid substitution variants are characterized by at least one residue in the sequence being removed and another residue being inserted in its place. In one embodiment, the amino acid substitution variant comprises the substitution of up to 10, 9, 8, 7, 6, 5, 4, 3 or 2 amino acids. Preference is given to modifications being in positions in the amino acid sequence which are not conserved between homologous proteins or peptides and/or to replacing amino acids with other ones having similar properties. Preferably, amino acid substitutions in protein variants are conservative amino acid substitutions. A conservative amino acid substitution involves substitution of an amino acid with another one of the same family of amino acids, i.e., amino acids which are related in their side chains (e.g., in terms of the electrical charge and/or size). Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine)

amino acids. Phenylalanine, tryptophan, and tyrosine are sometimes classified jointly as aromatic amino acids. However, it is also possible to replace amino acids with other ones having different properties, e.g., substituting one or more (surface-exposed) hydrophobic amino acids with one or more hydrophilic amino acids in order to reduce or inhibit aggregation of the isolated (poly-)peptides, wherein, preferably, other properties of these (poly-)peptides, e.g., their immunogenicity or binding properties, are not compromised by such amino acid substitutions.

According to the present invention, the degree of similarity, preferably identity, between a given reference amino acid sequence and an amino acid sequence which is a variant of said given amino acid sequence will preferably be at least about 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree/percentage of similarity or identity is given for the entire length of the reference amino acid sequence.

In one embodiment, the immunogenic variant is an equivalent protein from another *H. pylori* strain. In one embodiment, the equivalent protein is a homologue, preferably an orthologue. An "orthologue" is a homologous gene/protein that is related through speciation from a single ancestral gene/protein, not through gene duplication.

In one embodiment, the immunogenic variant comprises an amino acid sequence which is at least 60%, at least 70%, at least 80%, at least 90%, at least 95% or at least 97% (e.g., 97% or 98% or 99%) identical to an amino acid sequence selected from the group consisting of SEQ ID NO: 1, residues 37 to 463 of SEQ ID NO: 1, SEQ ID NO: 3, SEQ ID NO: 15 and SEQ ID NO: 5.

In one embodiment, the isolated (poly-)peptide is a recombinant (poly-)peptide.

The term "recombinant (poly-)peptide", as used herein, is meant to refer to a (poly-)peptide resulting from the expression of recombinant nucleic acid molecules (e.g., DNA) within living cells, e.g. by means of particular expression vectors. Recombinant nucleic acid molecules are nucleic acid molecules formed by laboratory methods of genetic recombination (e.g., molecular cloning).

In one embodiment, the isolated (poly-)peptide is produced in a host cell, preferably a prokaryotic host cell, such as *E. coli*.

In one embodiment, the isolated (poly-)peptide described herein further comprises a detectable label or tag. The term "detectable label or tag", as used herein, refers to detectable labels or tags allowing the detection and/or isolation and/or immobilization of the isolated (poly-)peptides described herein, and is meant to include any labels/tags known in the art for these purposes. Particularly preferred are affinity tags, such as chitin binding protein (CBP), maltose binding protein (MBP), glutathione-S-transferase (GST), poly(His) (e.g., 6× His or His6), Strep-tag®, Strep-tag II® and Twin-Strep-tag®; solubilization tags, such as thioredoxin (TRX), poly(NANP) and SUMO; chromatography tags, such as a FLAG-tag; epitope tags, such as V5-tag, myc-tag and HA-tag; fluorescent labels or tags (i.e., fluorochromes/-phores), such as fluorescent proteins (e.g., GFP, YFP, RFP etc.) and fluorescent dyes (e.g., FITC, TRITC, coumarin and cyanine); luminescent labels or tags, such as luciferase; and (other) enzymatic labels (e.g., peroxidase, alkaline phosphatase, beta-galactosidase, urease or glucose oxidase). Also included are combinations of any of the foregoing labels or tags.

The amino acid sequence of a (poly)peptidic label or tag may be introduced at any position within the amino acid sequence of the isolated (poly-)peptides described herein. For example, it may be added to their N- and/or C-terminus and/or to an amino acid side chain, e.g., by EDC-NHS coupling to lysines. The same applies to non-peptidic labels or tags.

In one embodiment, the isolated (poly-)peptide is a fusion protein.

The term "fusion protein" refers to proteins created by joining two or more distinct (poly-)peptides or proteins, preferably head-to-tail (i.e., N-terminus to C-terminus or vice versa), resulting in a single protein with functional properties derived from each of the original proteins.

The present invention also provides a fusion protein as defined herein.

The isolated (poly-)peptide according to the present invention may further comprise one or more modifications increasing the stability and/or preventing aggregation of the isolated (poly-)peptide. The term "stability" of the isolated (poly-)peptide relates, in particular, to its "half-life", e.g., in vivo. "Half-life" relates to the period of time which is needed to eliminate half of the activity, amount, or number of molecules. Prevention of aggregation will also increase the storage stability of the isolated (poly-)peptide.

The isolated (poly-)peptide may, for example, be fused or conjugated to a half-life extension module. Such modules are known to a person skilled in the art and include, for example, albumin, an albumin-binding domain, an Fc region/domain of an immunoglobulins, an immunoglobulin-binding domain, an FcRn-binding motif, and a polymer. Particularly preferred polymers include polyethylene glycol (PEG), hydroxyethyl starch (HES), hyaluronic acid, polysialic acid and PEG-mimetic peptide sequences. Modifications preventing aggregation of the isolated (poly-)peptides are also known to the skilled person and include, for example, the substitution of one or more hydrophobic amino acids, preferably surface-exposed hydrophobic amino acids, with one or more hydrophilic amino acids. In one embodiment, the isolated (poly-)peptide or the immunogenic variant thereof or the immunogenic fragment of any of the foregoing, comprises the substitution of up to 10, 9, 8, 7, 6, 5, 4, 3 or 2, preferably 5, 4, 3 or 2, hydrophobic amino acids, preferably surface-exposed hydrophobic amino acids, with hydrophilic amino acids. Preferably, other properties of the isolated (poly-)peptide, e.g., its immunogenicity, are not compromised by such substitution.

The isolated (poly-)peptide according to the present invention may also be fused or conjugated to a carrier material, such as Keyhole Limpet Hemocyanin (KLH), BSA, ovalbumin etc., in order to present the respective antigen to the immune system of the subject in a way that allows or promotes the eliciting of an immune response and, in particular, high titer antibodies.

The term "fused to", as used herein, refers, in particular, to genetic fusion, e.g., by recombinant DNA technology.

The term “conjugated to”, as used herein, refers, in particular, to chemical and/or enzymatic conjugation resulting in a stable covalent link.

The isolated (poly-)peptide according to the present invention may further comprise an amino acid sequence allowing the targeted delivery of the isolated (poly-)peptide to a given cell, tissue or organ, preferably an amino acid sequence that targets the isolated (poly-)peptide to a particular cell type, e.g., dendritic cells. Suitable amino acid sequences are described, e.g., in Sioud et al., 2013 and Apostolopoulos et al., 2013, and include, for example a peptide with the amino acid sequence NWYLPWLGTNDW (SEQ ID NO: 7).

In one embodiment, the nucleic acid molecule is DNA or RNA.

Also encompassed by the present invention are nucleic acid molecules, which hybridize under stringent hybridization conditions to a nucleic acid molecule according to above item (b).

“Stringent hybridization conditions”, as defined herein, involve hybridizing at 68° C. in 5×SSC/5×Denhardt’s solution/1.0% SDS, and washing in 0.2×SSC/0.1% SDS at room temperature, or involve an art-recognized equivalent thereof (e.g., conditions in which a hybridization is carried out at 60° C. in 2.5×SSC buffer, followed by several washing steps at 37° C. in a low buffer concentration, and remains stable). The parameters of salt concentration and temperature can be varied to achieve the optimal level of identity between the oligonucleotides and the target nucleic acid. Guidance regarding such conditions is available in the art, for example, by Molecular Cloning: A Laboratory Manual, 3rd Edition, J. Sambrook et al. eds., Cold Spring Harbor Laboratory Press, Cold Spring Harbor 2000, and Ausubel et al. (eds.), 1995, Current Protocols in Molecular Biology, (John Wiley and Sons, N.Y.) at Unit 2.10.

In one embodiment, the nucleic acid molecule is codon-optimized, e.g., for expression in bacteria other than *H. pylori*, such as *E. coli*, or for expression in eukaryotic cells, such as mammalian cells (e.g., CHO cells, BHK cells, COS cells and HEK293 cells) or insect cells (e.g., SF9 cells, SF21 cells and High Five™ cells).

In one embodiment, the nucleic acid molecule is contained/comprised in a vector.

The term “vector”, as used herein, includes any vector known to the skilled person, including plasmid vectors, cosmid vectors, phage vectors, such as lambda phage, viral vectors, such as adenoviral, AAV or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In one embodiment, the immunogenic composition further comprises at least one additional antigen from *H. pylori.*

The term “additional antigen from *H. pylori*”, as used herein, preferably refers to an antigen which is different from the agents, i.e. the isolated (poly-)peptides and nucleic acid molecules, in accordance with above items (a) and (b).

In a preferred embodiment, the additional antigen is selected from the group consisting of outer membrane proteins and virulence factor proteins of *H. pylori*, immunogenic fragments thereof and nucleic acid molecules encoding these proteins or fragments.

The term “outer membrane protein” refers to proteins that are associated with the outer membrane of *H. pylori*, which includes integral membrane proteins as well as lipoproteins that are anchored to the membrane by means of N-terminally attached lipids. Their structure and function is further described, e.g., in Koebnik et al., 2000. Particularly preferred outer membrane proteins of *H. pylori* for use in accordance with the present invention are selected from the group consisting of BabA, HpaA, Omp18, Omp22 and SabA.

The term “virulence factor protein”, as used herein, refers to proteins, e.g., functional proteins, such as enzymes, that contribute to the pathogenicity of *H. pylori* (see, for example, Kalali et al., 2014). A particularly preferred virulence factor protein in accordance with the present invention is gamma-glutamyltranspeptidase (gGT) of *H. pylori* (also referred to as HPGGT or HPG). Suitable HPG proteins are, for example, those described in WO 2008/046650 A1 and include an enzymatically inactivated form of HPG (S451/452A), optionally lacking the N-terminal secretion sequence.

Additional antigens that may be part of the immunogenic composition in accordance with the present invention are also those described in US 2007/0042448 A1 or WO 2004/094467 A2.

In one embodiment, the immunogenic composition further comprises at least one adjuvant.

The term “adjuvant” refers to a substance which enhances the immune response to an antigen, e.g., to an agent in accordance with above items (a) and (b) or an additional antigen from *H. pylori* as defined herein, for example by providing a general stimulation of the immune system. Suitable adjuvants are known to a person skilled in the art and include toxin-based adjuvants, TLR ligand-based adjuvants, nucleic acid/vector-based adjuvants, protein-based adjuvants, polymer-based adjuvants, mucosal adjuvants, ISCOM matrices and combinations of any of the foregoing. Particular adjuvants include, but are not limited to, polycationic polymers/peptides, immunostimulatory deoxynucleotides (ODNs), synthetic KLK peptides, neuroactive compounds (e.g., human growth hormone), alumn, Freund’s complete or incomplete adjuvants, cholera toxin (CT), CTA T-DD, heat-labile enterotoxin (LT), mutants of CT or LT, poly-IC, dendritic cell (DC) binding peptides and C3d fusion protein. In one embodiment, the TLR ligand-based adjuvant is a TLRS ligand, e.g., from the group of bacterial flagellins, such as those described in WO 2010/050903 A1, Mori et al., 2012 and Song et al., 2015. In one embodiment, the adjuvant is selected from the group consisting of cholera toxin (CT), CTA T-DD and heat-labile enterotoxin (LT).

In one embodiment, the immunogenic composition is a vaccine or is comprised in a vaccine.

The term “vaccine” refers to a preparation that confers or improves immunity to a particular disease. A vaccine in accordance with the present invention confers or improves immunity to a disease or disorder caused by or associated with *H. pylori*, in particular the specific diseases mentioned herein.

In one embodiment, the immunogenic composition of the present invention elicits an immune response comprising the secretion of antibodies, wherein, preferably, the antibodies inhibit the interaction between *H. pylori* HopQ and a member of the carcinoembryonic antigen-related cell adhesion molecule (CEACAM) family as defined herein. In one embodiment, the antibodies inhibit binding of *H. pylori* HopQ to the member of the CEACAM family and/or HopQ-CEACAM-mediated signaling. In one embodiment, the antibodies bind to an extracellular domain of *H. pylori* HopQ or a fragment thereof, e.g., the insertion domain, loop A, loop B, loop C and/or loop D of *H. pylori* HopQ. In one embodiment, the antibodies bind to an epitope of *H. pylori* HopQ comprising at least 1, 2, 3, 4, 5, 6, 7 or 8 amino acid residues comprised in the insertion domain, loop A, loop B, loop C and/or loop D, preferably loop A, loop B and/or loop C, of *H. pylori* HopQ.

According to the invention, an immunogenic/pharmaceutical composition contains an effective amount of the active agents, e.g., the (poly-)peptides or peptidomimetics or nucleic acid molecules or small molecules described herein, to generate the desired reaction or the desired effect.

An immunogenic/pharmaceutical composition in accordance with the present invention is preferably sterile. Immunogenic/pharmaceutical compositions can be provided in a uniform dosage form and may be prepared in a manner known per se. An immunogenic/pharmaceutical composition in accordance with the present invention may, e.g., be in the form of a solution or suspension.

The immunogenic/pharmaceutical composition may further comprise one or more carriers and/or excipients, all of which are preferably pharmaceutically acceptable. The term "pharmaceutically acceptable", as used herein, refers to the non-toxicity of a material, which, preferably, does not interact with the action of the active agent of the immunogenic/pharmaceutical composition. In particular, "pharmaceutically acceptable" means approved by a regulatory agency of the Federal or a state government or listed in the U.S. Pharmacopoeia, European Pharmacopoeia or other generally recognized pharmacopeia for use in animals, and more particularly in humans.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a subject. Possible carrier substances (e.g., diluents) are, for example, sterile water, Ringer's solution, Lactated Ringer's solution, physiological saline, bacteriostatic saline (e.g., saline containing 0.9% benzyl alcohol), phosphate-buffered saline (PBS), Hank's solution, fixed oils, polyalkylene glycols, hydrogenated naphthalenes and biocompatible lactide polymers, lactide/glycolide copolymers or polyoxyethylene/polyoxy-propylene copolymers. In one embodiment, the carrier is PBS. The resulting solutions or suspensions are preferably isotonic to the blood of the recipient. Suitable carriers and their formulations are described in greater detail in Remington's Pharmaceutical Sciences, 17$^{th}$ ed., 1985, Mack Publishing Co.

The term "excipient", as used herein, is intended to include all substances which may be present in a pharmaceutical composition and which are not active ingredients, such as salts, binders (e.g., lactose, dextrose, sucrose, trehalose, sorbitol, mannitol), lubricants, thickeners, surface active agents, preservatives, emulsifiers, buffer substances, stabilizing agents, flavouring agents or colorants.

Salts, which are not pharmaceutically acceptable, may be used for preparing pharmaceutically acceptable salts and are included in the invention. Pharmaceutically acceptable salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts. Salts may be added to adjust the ionic strength or tonicity.

Suitable preservatives for use in a pharmaceutical composition include antioxidants, citric acid, sodium citrate, benzalkonium chloride, chlorobutanol, cysteine, methionine, parabens and thimerosal.

Suitable buffer substances for use in a pharmaceutical composition include acetic acid in a salt, citric acid in a salt, boric acid in a salt and phosphoric acid in a salt. Other suitable buffer substances include arginine-hydrochloride and arginine-phosphate.

Suitable stabilizing agents include glycerol, ascorbate and histidine.

The immunogenic compositions according to the present invention may also be formulated as described in U.S. Pat. No. 6,838,089 B1 and U.S. Pat. No. 6,372,260 B1.

The immunogenic/pharmaceutical composition in accordance with the present invention may also be formulated as a stable lyophilized product that is reconstituted with an appropriate diluent, which, optionally, comprises one or more excipients as described above.

The present invention also provides an immunogenic composition as defined herein for use as a medicament.

The present invention also provides an immunogenic composition as defined herein for use in a method of preventing or treating a disease or disorder caused by or associated with *H. pylori*.

The present invention further provides the use of an immunogenic composition as defined herein in the preparation of a medicament for preventing or treating a disease or disorder caused by or associated with *H. pylori*.

The present invention also provides a method of preventing or treating a disease or disorder caused by or associated with *H. pylori* in a subject, said method comprising administering the immunogenic composition as defined herein to the subject.

The present invention further provides a CEACAM protein or a functional fragment thereof being able to interact with *H. pylori* HopQ for use in a method of preventing or treating a disease or disorder caused by or associated with *H. pylori*, wherein the CEACAM protein or functional fragment thereof is attached to a solid support, preferably a non-cellular solid support.

The present invention further provides the use of a CEACAM protein or a functional fragment thereof being able to interact with *H. pylori* HopQ in the preparation of a medicament for preventing or treating a disease or disorder caused by or associated with *H. pylori*, wherein the CEACAM protein or functional fragment thereof is attached to a solid support, preferably a non-cellular solid support.

The present invention also provides a method of preventing or treating a disease or disorder caused by or associated with *H. pylori* in a subject, said method comprising administering a CEACAM protein or a functional fragment thereof being able to interact with *H. pylori* HopQ to the subject, wherein the CEACAM protein or functional fragment thereof is attached to a solid support, preferably a non-cellular solid support.

The term "solid support", as used herein, refers to any solid support able to bind to a CEACAM protein or a functional fragment thereof as defined herein. In one embodiment, the solid support is a non-cellular solid support. Such non-cellular solid supports may comprise support materials such as polymers, in particular bioadhesive cationic polymers (e.g., chitosan, polygalactosamine, polylysine, diethylaminoethyldextran (DEAE), DEAE-imine). The support may have any possible structural configuration as long as the molecule bound thereto is able to bind to its respective binding partner (e.g., *Helicobacter* bacteria). Suitable configurations include spherical configurations, such as microspheres (see, for example, WO 2013/164652 A2). In one embodiment, the solid support is a microsphere.

The present invention further provides an inhibitor of the interaction between *Helicobacter bilis* (*H. bilis*) and a member of the carcinoembryonic antigen-related cell adhesion molecule (CEACAM) family for use in a method of preventing or treating a disease or disorder caused by or associated with *H. bilis.*

The present invention further provides the use of an inhibitor of the interaction between *H. bilis* and a member of the carcinoembryonic antigen-related cell adhesion molecule (CEACAM) family in the preparation of a medicament for preventing or treating a disease or disorder caused by or associated with *H. bilis.*

The present invention further provides a method of preventing or treating a disease or disorder caused by or associated with *H. bilis* in a subject, said method comprising administering an inhibitor of the interaction between *H. bilis* and a member of the carcinoembryonic antigen-related cell adhesion molecule (CEACAM) family to the subject.

According to the present invention, a disease or disorder caused by or associated with *H. bilis* is preferably selected from the group consisting of *H. bilis* infection, cholecystitis, gallstone(s), gallbladder cancer and bile duct cancer.

In one embodiment, the inhibitor inhibits, e.g., competitively inhibits, binding of *H. bilis* to the member of the CEACAM family, preferably to an extracellular domain of the member of the CEACAM family, more preferably to the N-domain of the member of the CEACAM family.

In one embodiment, the member of the CEACAM family is expressed on the surface of epithelial cells, endothelial cells and/or immune cells (in particular leukocytes, such as T cells, B cells and neutrophils). In one embodiment, the member of the CEACAM family is expressed on the surface of epithelial cells (e.g., bile duct epithelial cells), preferably at the apical side of epithelial cells.

In one embodiment, the member of the CEACAM family is selected from the group consisting of human CEACAM family members, non-human primate CEACAM family members and rat CEACAM family members. In one embodiment, the member of the CEACAM family is selected from the group consisting of CEACAM1, CEACAM5 and CEACAM6.

In one embodiment, the inhibitor is selected from the group consisting of (a) (poly-)peptide ligands or peptidomimetic ligands binding to the member of the CEACAM family, preferably to an extracellular domain of the member of the CEACAM family, more preferably to the N-domain of the member of the CEACAM family;

(b) nucleic acid molecules encoding the (poly-)peptide ligands of (a);

(c) nucleic acid ligands binding to the member of the CEACAM family, preferably to an extracellular domain of the member of the CEACAM family, more preferably to the N-domain of the member of the CEACAM family;

(d) inhibitory nucleic acid molecules inhibiting the expression of the member of the CEACAM family; and (e) small molecules binding to the member of the CEACAM family, preferably to an extracellular domain of the member of the CEACAM family, more preferably to the N-domain of the member of the CEACAM family.

In one embodiment, the inhibitor is comprised in a pharmaceutical composition.

The present invention further provides an in vitro method for identifying a drug candidate for preventing or treating a disease or disorder caused by or associated with *H. bilis*, the method comprising (a) contacting (i) a CEACAM protein or a functional fragment thereof with (ii) *H. bilis* and (iii) a test compound, and (b) determining whether the test compound inhibits the interaction between the CEACAM protein or the functional fragment thereof and *H. bilis,* wherein a test compound inhibiting the interaction between the CEACAM protein or the functional fragment thereof and *H. bilis* is identified as a drug candidate for preventing or treating a disease or disorder caused by or associated with *H. bilis.*

In one embodiment, step (b) comprises determining whether the test compound inhibits binding of *H. bilis* to the CEACAM protein or the functional fragment thereof, wherein, preferably, the functional fragment of the CEACAM protein comprises an extracellular domain or a fragment thereof, preferably the N-domain.

In one embodiment, the CEACAM protein is selected from the group consisting of human CEACAM proteins, non-human primate CEACAM proteins and rat CEACAM proteins. In one embodiment, the CEACAM protein is selected from the group consisting of CEACAM1, CEACAM5 and CEACAM6.

In one embodiment, the test compound is selected from the group consisting of (poly-)peptides, peptidomimetics, nucleic acid molecules and small molecules.

In another aspect, the present invention relates to the use of a CEACAM protein or a functional fragment thereof being able to interact with *H. bilis* for studying *H. bilis* infection or identifying a drug candidate for preventing or treating a disease or disorder caused by or associated with *H. bilis.*

In a further aspect, the present invention relates to the use of a cell heterologously expressing a CEACAM protein or a functional fragment thereof being able to interact with *H. bilis* for studying *H. bilis* infection or identifying a drug candidate for preventing or treating a disease or disorder caused by or associated with *H. bilis.*

In yet another aspect, the present invention relates to the use of a non-human transgenic animal heterologously expressing a CEACAM protein or a functional fragment thereof being able to interact with *H. bilis* for studying *H. bilis* infection or identifying a drug candidate for preventing or treating a disease or disorder caused by or associated with *H. bilis.*

In one embodiment of the above uses, the CEACAM protein is selected from the group consisting of human CEACAM proteins, non-human primate CEACAM proteins and rat CEACAM proteins. In one embodiment, the CEACAM protein is selected from the group consisting of CEACAM1, CEACAM5 and CEACAM6.

The present invention further provides a CEACAM protein or a functional fragment thereof being able to interact with *H. bilis* for use in a method of preventing or treating a disease or disorder caused by or associated with *H. bilis*, wherein the CEACAM protein or functional fragment thereof is attached to a solid support, preferably a non-cellular solid support.

The present invention further provides the use of a CEACAM protein or a functional fragment thereof being able to interact with *H. bilis* in the preparation of a medicament for preventing or treating a disease or disorder caused by or associated with *H. bilis*, wherein the CEACAM protein or functional fragment thereof is attached to a solid support, preferably a non-cellular solid support, The present invention also provides a method of preventing or treating a disease or disorder caused by or associated with *H. bilis* in a subject, said method comprising administering a CEACAM protein or a functional fragment thereof being able to interact with *H. bilis* to the subject, wherein the CEACAM protein or functional fragment thereof is attached to a solid support, preferably a non-cellular solid support.

In one embodiment of the above uses, the CEACAM protein is selected from the group consisting of human CEACAM proteins, non-human primate CEACAM proteins and rat CEACAM proteins. In one embodiment, the CEACAM protein is selected from the group consisting of CEACAM1, CEACAM5 and CEACAM6.

The agents and compositions described herein may be administered via any conventional route, such as by enteral administration or by parenteral administration including by injection or infusion. In one embodiment, administration is parenterally, e.g., intradermally, subcutaneously or intramuscularly. In one embodiment, mucosal administration is used, e.g., orally or sublingually.

The agents and compositions described herein are administered in effective amounts. An "effective amount" refers to the amount, which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. An effective amount of an agent or composition described herein will depend on the condition to be treated, the severeness of the disease, the individual parameters of the subject, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a subject is insufficient with an initial dose, higher doses (or effectively higher doses achieved by a different, more localized route of administration) may be used.

The present invention further provides a kit comprising (i) an inhibitor or (ii) an immunogenic composition or (iii) a CEACAM protein or functional fragment thereof as defined herein.

As used herein, the term "kit of parts (in short: kit)" refers to an article of manufacture comprising one or more containers and, optionally, a data carrier. Said one or more containers may be filled with one or more of the means or reagents disclosed herein. Additional containers may be included in the kit that contain, e.g., diluents, buffers and further reagents. Said data carrier may be a non-electronical data carrier, e.g., a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g., an internet database, a centralized, or a decentralized database. Said data carrier may comprise instructions for the use of the kit in accordance with the present invention.

The present invention is further illustrated by the following examples, which are not to be construed as limiting the scope of the invention.

EXAMPLES

Example 1

*H. pylori* Binds to CEACAMs Expressed in Human Stomach

Figure 2:
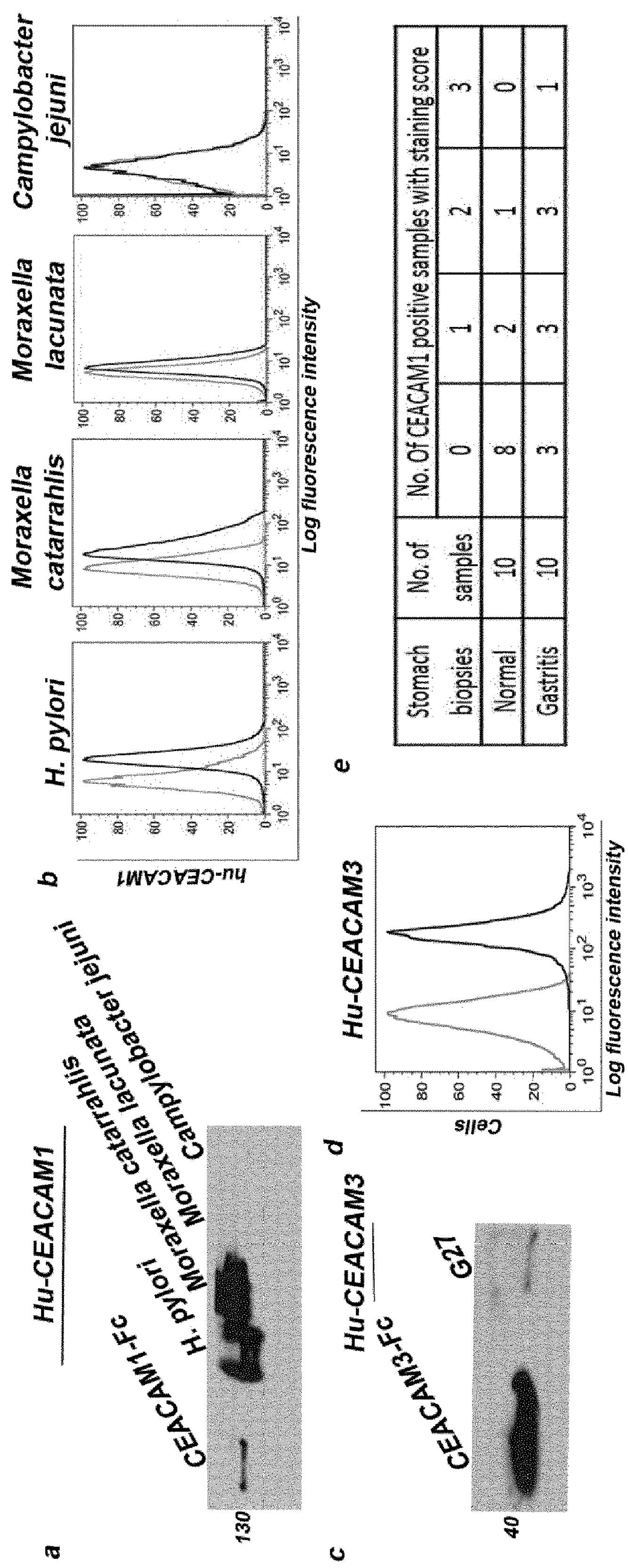
FIG. 2 shows that Hu-CEACAM1 employment by human pathogens is highly selective. Binding quantification of different *H. pylori* strains and other bacteria to the CEACAM family members. (a, c and f) *H. pylori* strains, *Moraxella catarrhalis, Moraxella lacunata* and *Campylobacter jejuni* were incubated with hu-CEACAM1, 3, 5, 6 and 8-Fc. After washing, bacteria were lysed and proteins were subjected to SDS-gel/western blot and detected with corresponding antibodies, or (b, d and g) were stained with anti-hu-IgG-FITC and the fluorescence intensity of bacteria was analyzed by flow cytometry (3 technical replicates). One-way ANOVA, n. s.: not significant. Error bars indicate s.e.m. (e) Scoring of the CEACAM expression in stomach biopsies of naïve healthy individuals and *H. pylori* positive gastritis. (h) The amino acid sequences of N-terminal domains of the hu-CEACAM1 (P13688; SEQ ID NO: 28), CEACAM5 (P06731; SEQ ID NO: 29), CEACAM6 (P40199; SEQ ID NO: 30) and CEACAM8 (P31997; SEQ ID NO: 31) were compared. (i) SDS-PAGE showing Coomassie stain of purified hu-CEACAM1, 1ΔN, 6 and 8-FC expression.
Figure 2:
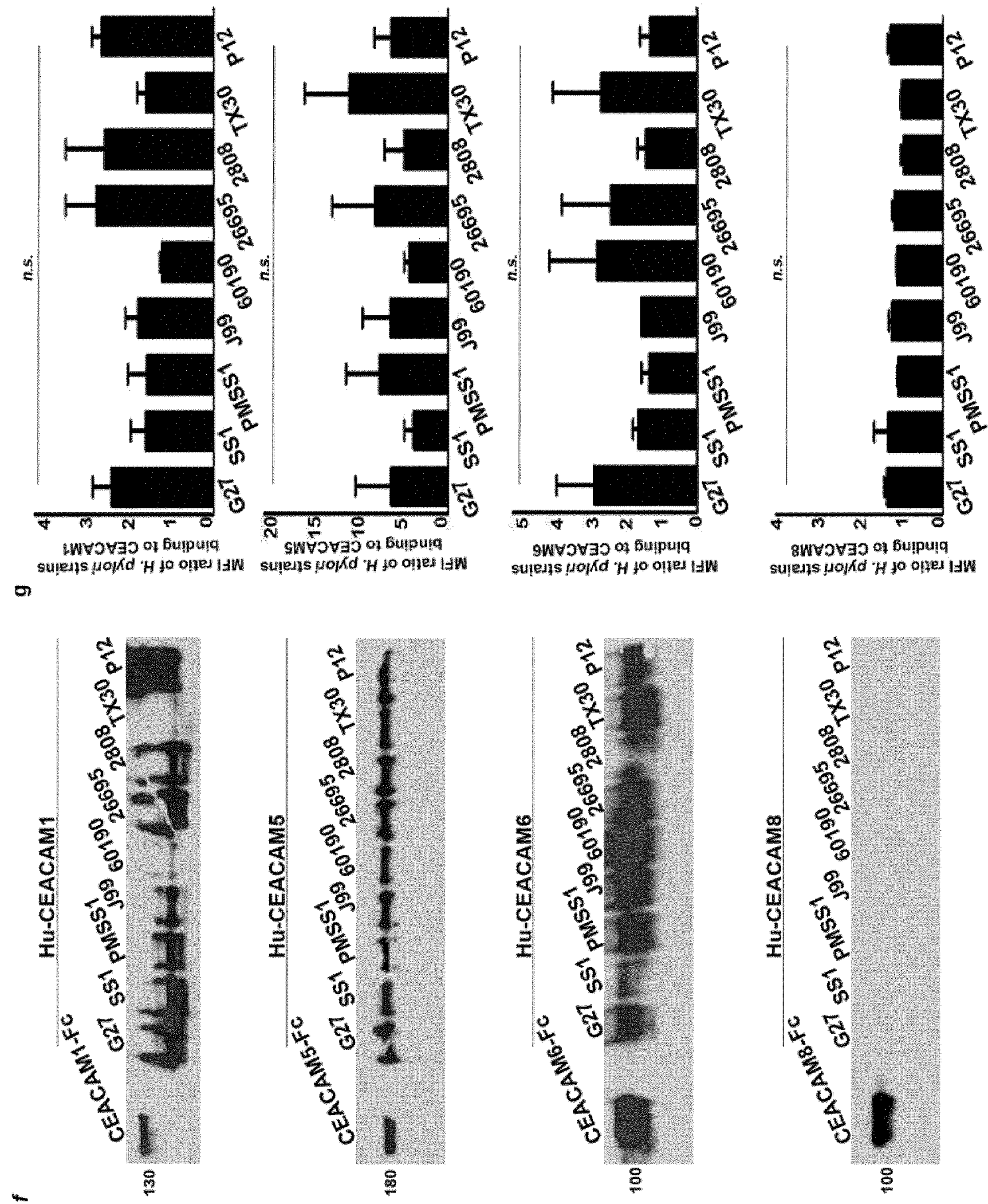
Figure 2:
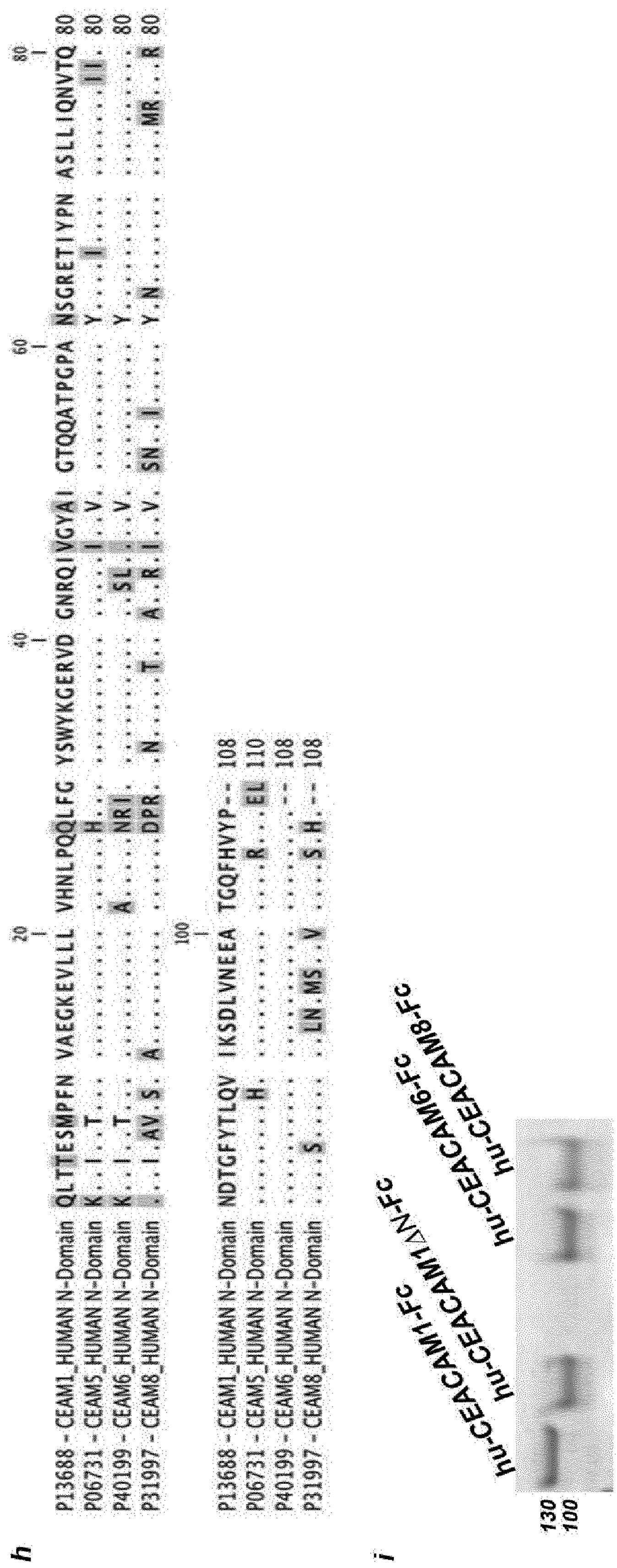

Using pull-down and flow cytometric approaches a robust interaction of the *H. pylori* strain G27 with recombinant human CEACAM1-Fc (FIG. 1*a*) was found, comparable to that of *Moraxella catarrhalis* (FIGS. 2*a* and *b*). As negative control, *Moraxella lacunata* did not bind to human CEACAM1, nor did *Campylobacter jejuni*, a pathogen closely related to *H. pylori* (FIGS. 2*a* and *b*). When testing for CEACAM specificity, a clear interaction of *H. pylori* with CEACAM5 and 6, but not with CEACAM8 was observed (FIG. 1*b*), and comparison of the respective N-domains indicated several residues conserved in CEACAM1, 5, and 6 but not in CEACAM8 (FIG. 2*h*). *H. pylori* interacted also with CEACAM3 (FIGS. 2*c* and *d*). Importantly, all *H. pylori* strains tested so far bound to these CEACAMs (FIGS. 2*f* and *g*) including well-characterized reference strains (26695, J99) and the mouse-adapted strain SS1. However, binding strength differed among strains, with some preferentially binding to CEACAM1, and others to CEACAM5 and/or CEACAM6 (FIGS. 2*f* and *g*). Strikingly, CEACAM1 binders were mostly from the group of highly virulent strains, possessing the cag pathogenicity island (cagPAI) encoding a type IV secretion system (T4SS) for delivery of CagA, while TX30 as a classical cagPAI-negative strain showed preferred binding to CEACAM5 and 6 (FIGS. 2*f* and *g*). The inventors then analyzed the expression profiles of CEACAM1, CEACAM5 and CEACAM6 in normal and inflamed human stomach tissues and gastric cancer. CEACAM1 and CEACAM5 were expressed at the apical side of epithelial cells, and their expression, as well as that of CEACAM6, was up-regulated upon gastritis and in gastric tumors (FIG. 1*c* and FIG. 2*e*). During infection, *H. pylori*-induced responses may thus lead to increased expression of its CEACAM-receptors.

Figure 10:
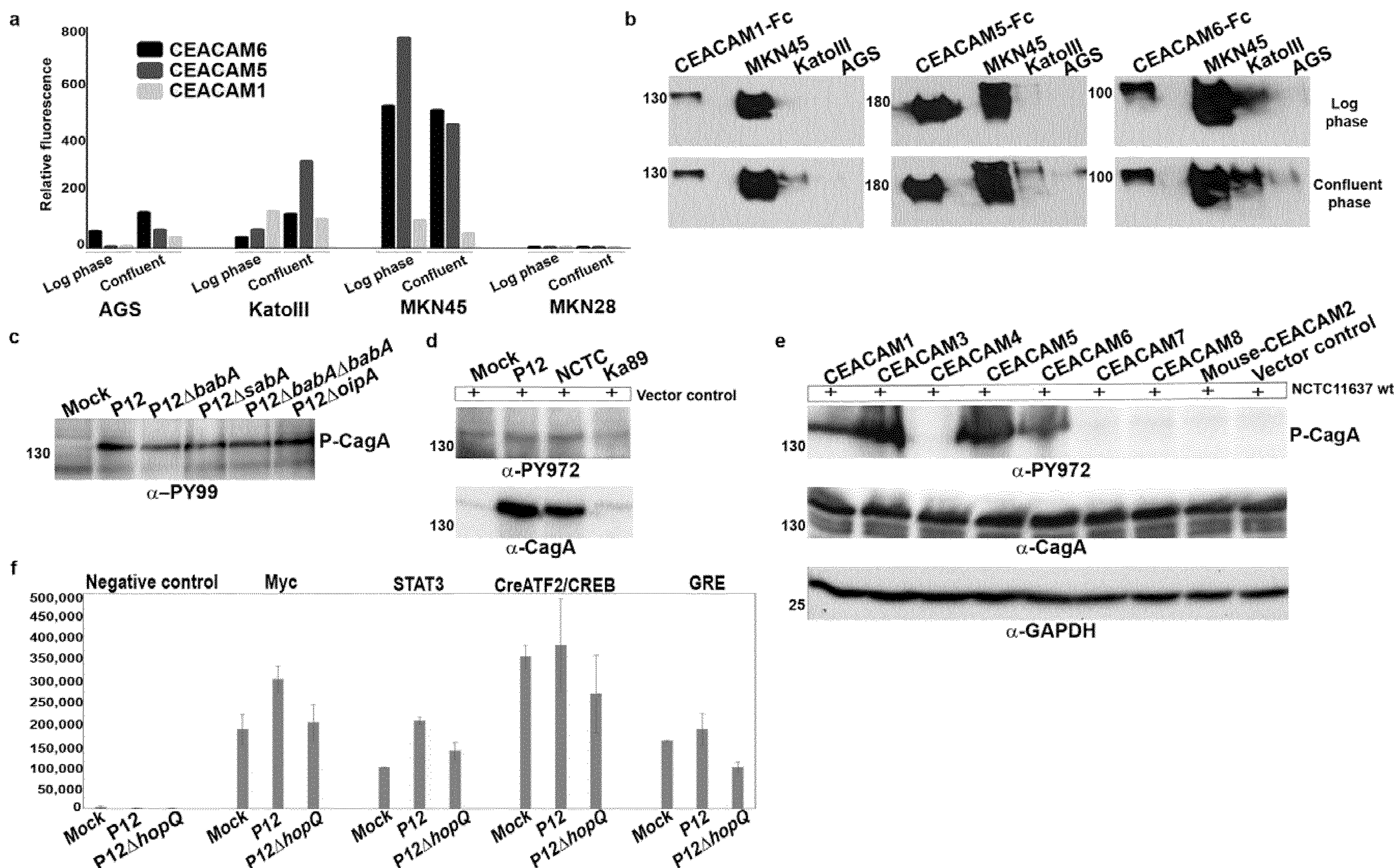
FIG. 10 shows characterization of the CEACAM expression pattern and CagA phosphorylation in gastric cell lines. The gastric cell lines in different cell growth stages were stained with mAb for hu-CEACAM1, CEACAM5 and CEACAM6 and either (a) stained by FITC-conjugated secondary antibody and subsequently, CEACAM cell surface expression was monitored by flow cytometry or (b) cell lysates were subjected to SDS-gel/western blot and detected with corresponding antibodies. (c) AGS cells were infected with wt *H. pylori* strain P12 and various isogenic mutants of important adhesins (BabA, SabA and OipA or the double mutant BabA/SabA). Cells were infected for 6 hours using MOI 50. The blot was probed with the α-PY-99. (d) HEK293 cells were transfected with vector control, followed by MOI 50 infection for 6 hours with indicated cagPAI-positive *H. pylori* strains P12, NCTC11637 and the cagPAI-negative strain Ka89. (e) HEK293 cells were transfected with indicated CEACAM expression vectors for 48 hours, followed by MOI 50 infection for 6 hours with wt *H. pylori* strain NCTC11637. Anti-CagA detection served as control for equal bacteria loading. Anti-GAPDH detection served as cell lysate loading control. (f) CHO-hu-CEACAM1-4L were transfected with indicated luciferase reporter constructs for the transcription factors Myc, STAT3, CreATF2/CREB, GRE and as negative control pTAL-Luciferase. Then transfected cells were infected with *H. pylori* wt, isogenic hopQ deletion mutant or left untreated followed by measurement of luciferase activities as Relative Light Units (RLU) as indicated (n=3). (g) Pre-incubation of AGS cells with a $HopQ^{AD}$, but not the HopQ-ID deletion mutant ($HopQ^{AD}\Delta$ID) inhibits P12-induced phosphorylation of CagA at submicromolar concentrations, as well as the cell elongation. Similarly, pre-incubation with the HopQ-ID peptide (aa 190-218; see FIG. 9*j*) blocks P12-induced phosphorylation of CagA, albeit at ~10 to 20 fold higher concentrations compared to the full $HopQ^{AD}$.
Figure 10:
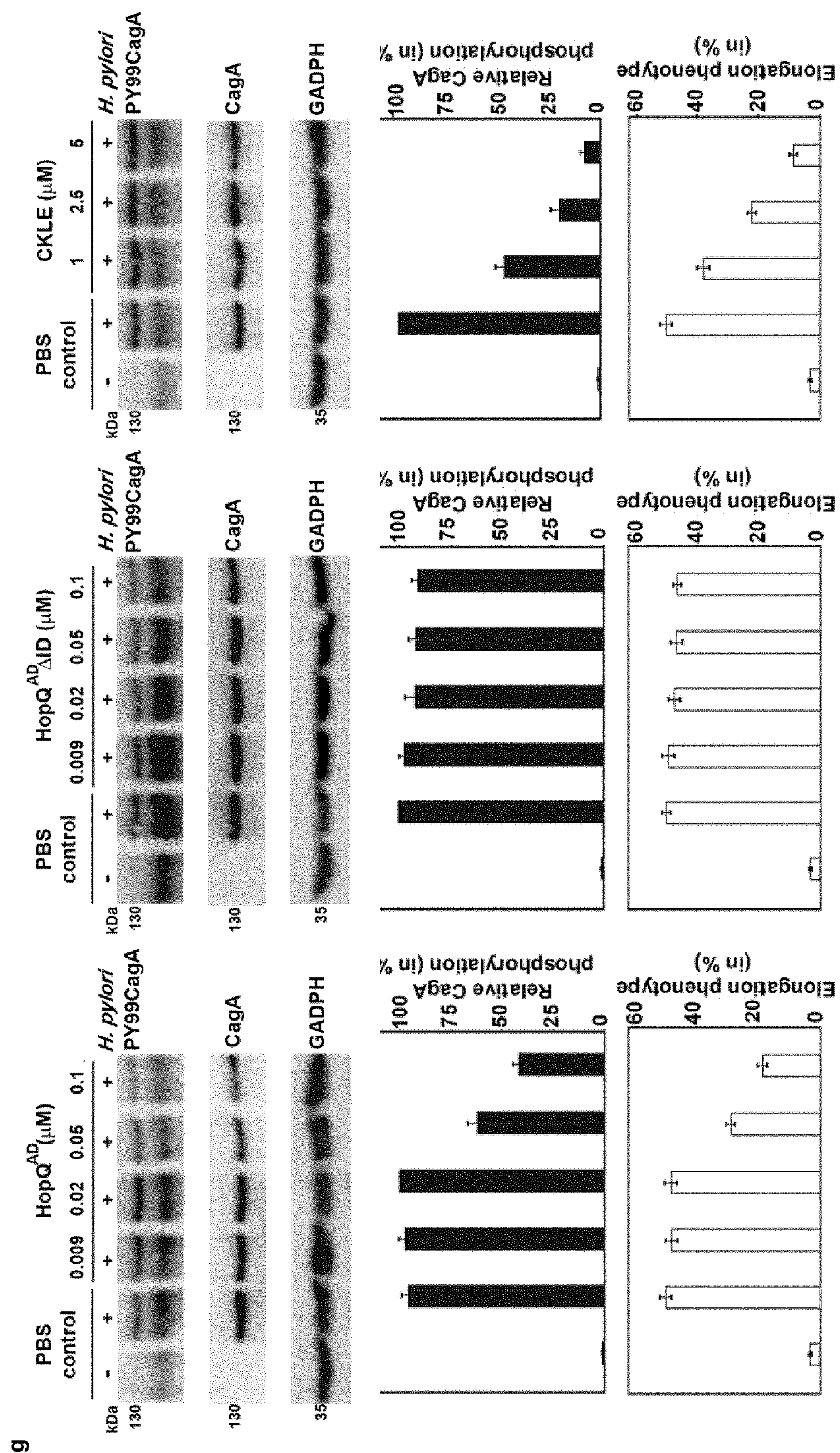

The inventors found that *H. pylori* bound to the N-domain of CEACAM1 (FIG. 1*d*), since recombinant CEACAM1ΔN did not interact with the bacteria, and further observed binding of *H. pylori* to all CEACAMs containing the N-domain, as well as to the N-domain alone (FIG. 1*e*). However, binding to the N-domain alone was weaker than to the N-A1-B CEACAM1 variant, which bound less than the N-A1-B-A2 variant (FIG. 1*e*), indicating that these domains stabilize the CEACAM1-*H. pylori* interaction, while binding was only partially dependent on glycosylation (FIG. 10. This CEACAM-binding property provides *H. pylori* robust epithelial adherence independent of the Lewis blood group antigens used by the BabA and SabA adhesins. While over-expression of CEACAMs in gastrointestinal tumors is well described, their upregulation during *H. pylori*-induced inflammation in the stomach has not been reported so far, suggesting the pathogen has the ability to shape its own adhesive niche. A plausible route to CEACAM modulation is through the transcription factors NF-κB and AP1, both of which are induced during *H. pylori* infection and are known to regulate CEACAM expression. The up-regulation of these CEACAM-receptors may compensate for the described loss of BabA expression during colonization, enabling a persistent colonization.

Example 2

Species Specificity of *Helicobacter*—CEACAM Interaction

Figure 3:
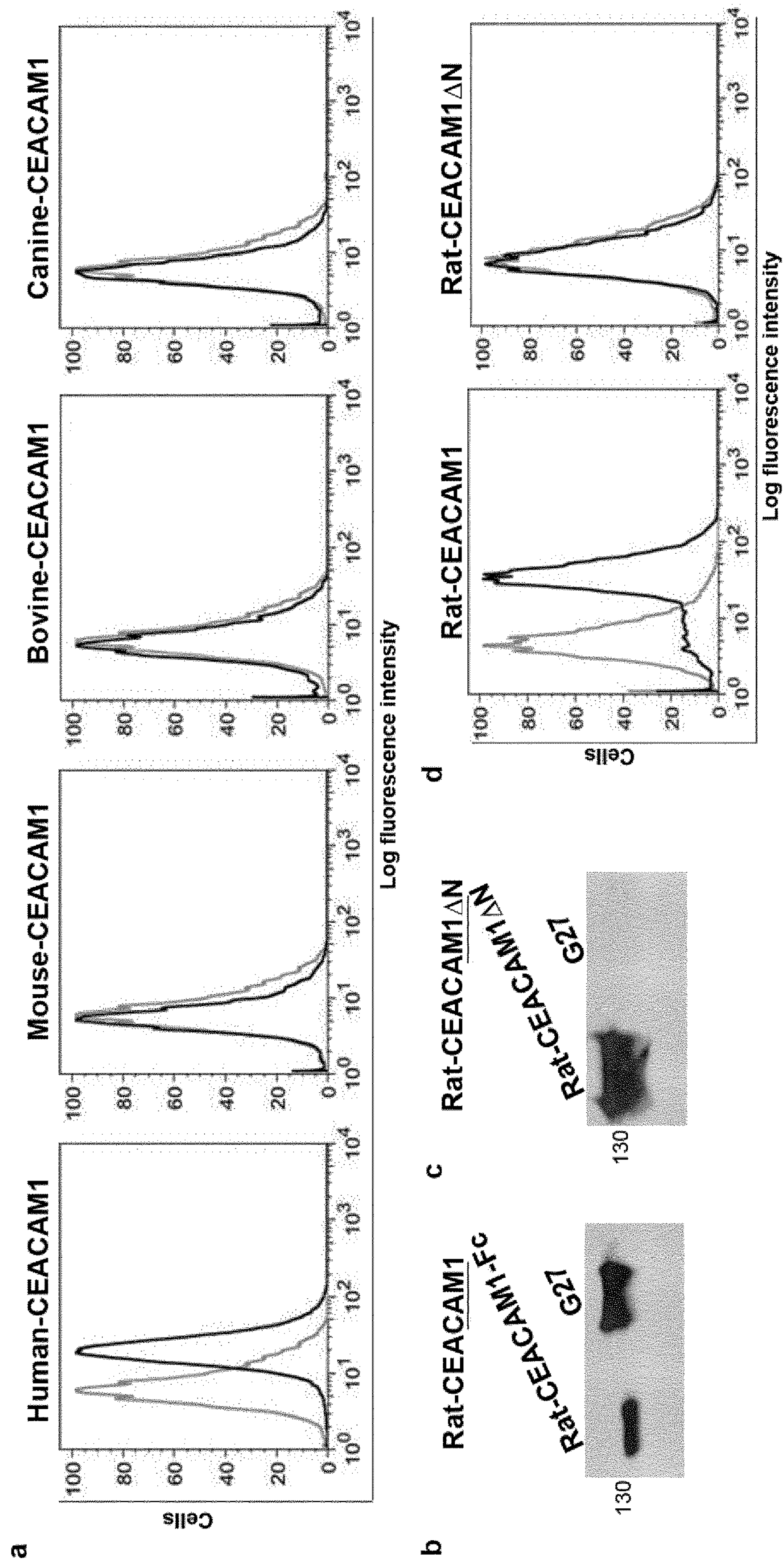
FIG. 3 shows *H. pylori* binding to CEACAM1 orthologues. (a) Soluble GFP-tagged CEACAMs from different species were incubated with *H. pylori* and fluorescence was determined by flow cytometry (3 technical replicates). Bacterial pull-down using (b) rat-CEACAM1-Fc (c) and rat-CEACAM1ΔN-Fc was detected by western blot, or (d) stained with α-Hu-IgG-FITC and analyzed by flow cytometry. (e) Representative confocal images of *H. pylori* binding to human, rat and mouse CEACAM1-expressing CHO cells. Untransfected CHO served as control. Scale bars: left-hand panels, 25 μm, wright-hand panels, 10 μm. (f) Pull down of whole cell lysates of untransfected, human-, mouse- and rat CEACAM1-transfected CHO cells incubated with *H. pylori*. After washing, cells were lysed and proteins were subjected to SDS-gel/western blot and detected with corresponding α-CEACAM1 antibodies.
Figure 3:
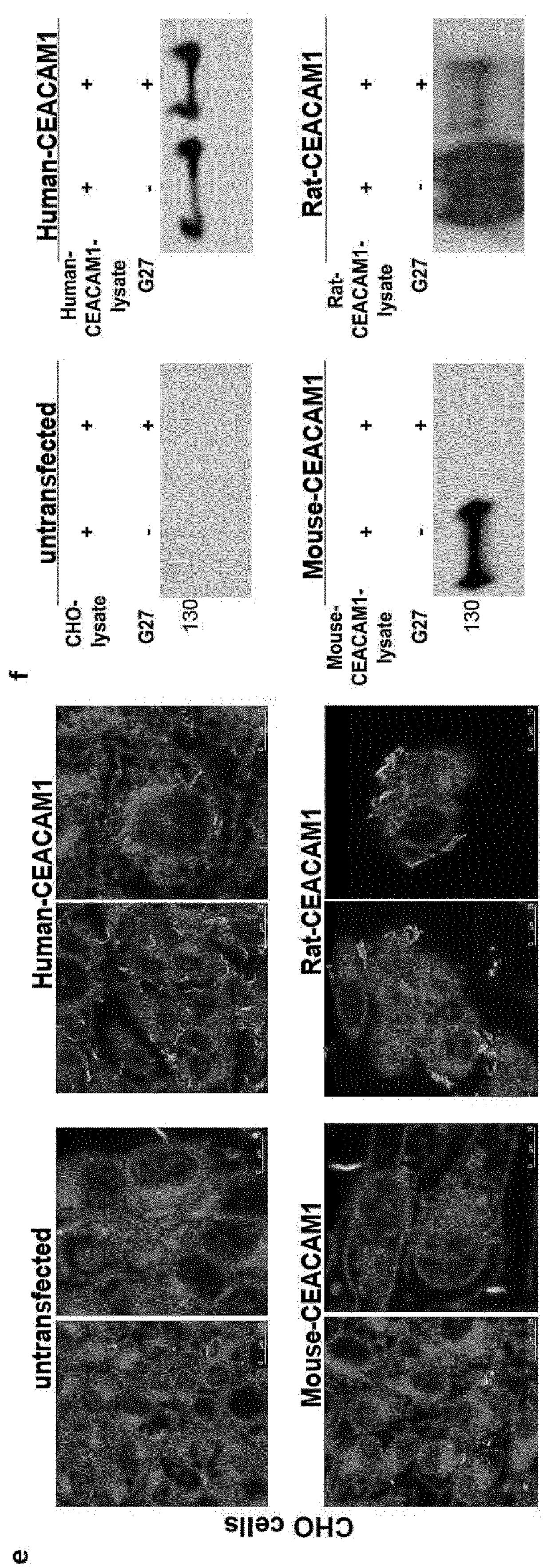
Figure 4:
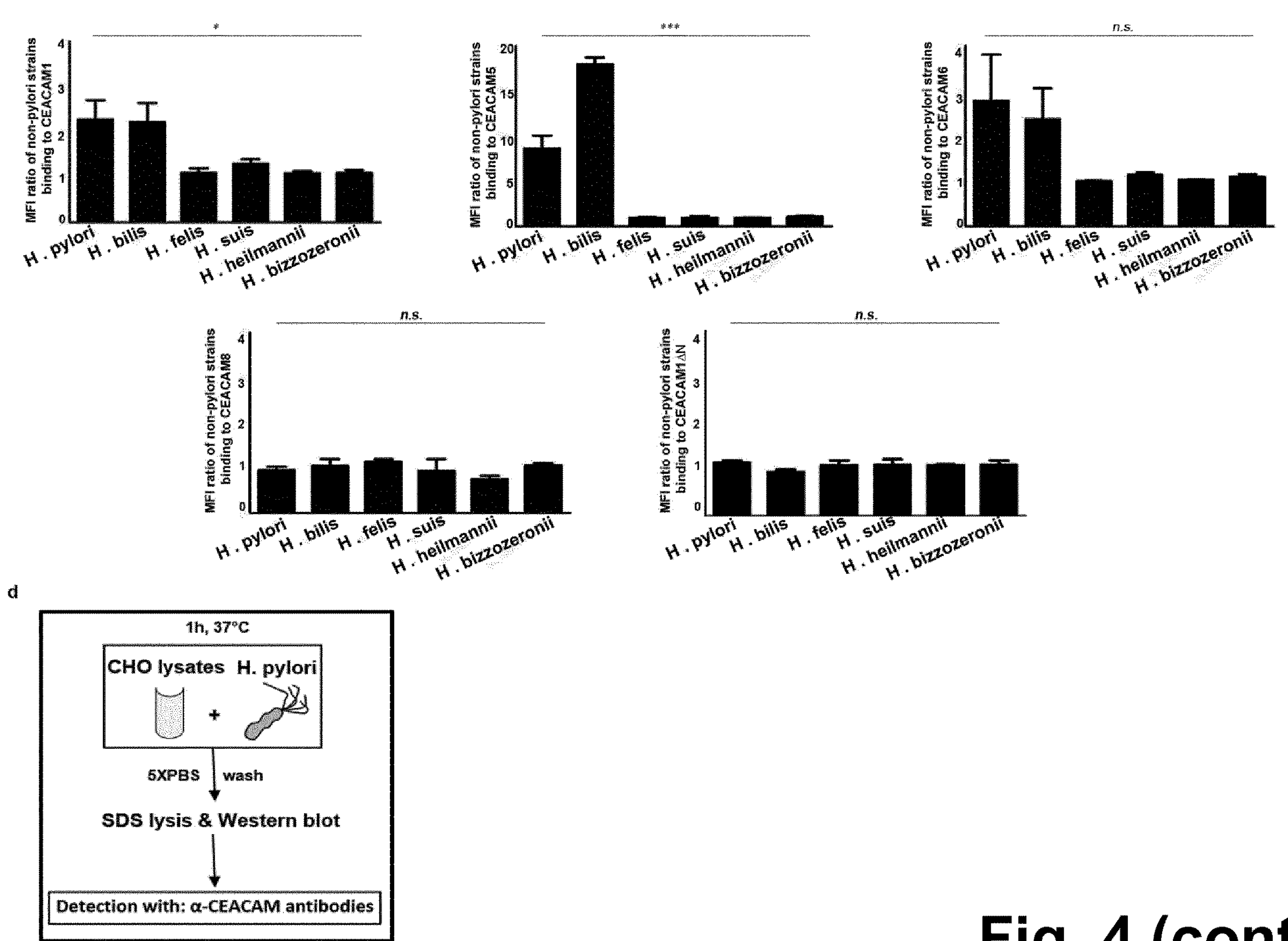
FIG. 4 relates to CEACAM1 orthologues and non *pylori* helicobacters. (a) The amino acid sequences of N-terminal domains of the human CEACAM1 (P13688; SEQ ID NO: 28), murine CEACAM1 (P31809; SEQ ID NO: 33) and rat CEACAM1 (P16573; SEQ ID NO: 32) were compared. Amino acids identical in the human and rat, but different to mouse-CEACAM1 sequences, are indicated by arrows. (b) Live non-*pylori* strains were incubated with hu-CEACAM1-Fc, CEACAM5-Fc, CEACAM6-Fc, CEACAM8-Fc and CEACAM1ΔN-Fc. After rigorous washing, bacteria were lysed and proteins were separated on SDS-gel and detected with corresponding antibodies. (c) After bacterial pull-down and anti-hu-IgG-FITC staining, the ratio of fluorescence intensity of bacteria was analyzed by flow cytometry (3 technical replicates). One-way ANOVA, *: P=0.03, ***: P=0.0001, n. s.: not significant. (d) Scheme of bacterial pull down for analysis of *H. pylori*-CEACAM interaction.

*H. pylori* has been described so far only to infect human and non-human primates. Although CEACAMs are found in most mammalian species, and have a high degree of conservation, the inventors found *H. pylori* to bind selectively to human, but not to mouse, bovine or canine CEACAM1 orthologues (FIG. 3*a*). However, surprisingly a strong interaction of *H. pylori* strains with rat-CEACAM1 was found (FIGS. 3*b* and *d*). Also here, this interaction was mediated through the N-domain of rat-CEACAM1 (FIGS. 3*c* and *d*). To substantiate these findings, the inventors transfected human, mouse or rat-CEACAM1 into CHO cells, which normally do not permit *H. pylori* adherence. Using confocal laser scanning microscopy, they observed de novo adhesion of *H. pylori* to CHO cells expressing human and rat, but not mouse CEACAM1 (FIG. 3*e*), which could be confirmed by pull down and western blotting of lysates from transfected cells (FIG. 3*f* and FIG. 4*d*). This finding makes *H. pylori* the first pathogen for which its CEACAM binding is not restricted to one species. Comparing the protein sequences of the CEACAM1-N domains, several amino acids conserved in human and rat differ in mouse (i.e. asn10, glu26, asn42, tyr48, pro59, thr66, asn77, val79, val89, ile90, glu103, tyr108) (FIG. 4*a*). In addition, their findings of a lack of binding to mouse CEACAM1 may explain the differences seen in pathology between infected mice and humans.

The genus *Helicobacter* comprises several other spp., i.e. *H. felis, suis*, and *bizzozeronii* as well as the human pathogenic *H. bilis* and *heilmannii*. When assessing the interaction of these *Helicobacters* with human CEACAMs, only *H. bilis* bound to hu-CEACAM1, 5 and 6 (FIGS. 4*b* and *c*). As *H. pylori, H. bilis* interacted with the N-domain of hu-CEACAM1 (FIGS. 4*b* and *c*). This interaction may explain how *H. bilis* manages to colonize human bile ducts, where high levels of constitutively expressed CEACAM1 are present.

Example 3

HopQ is the *Helicobacter* Adhesin Interacting with CEACAMs

Figure 5:
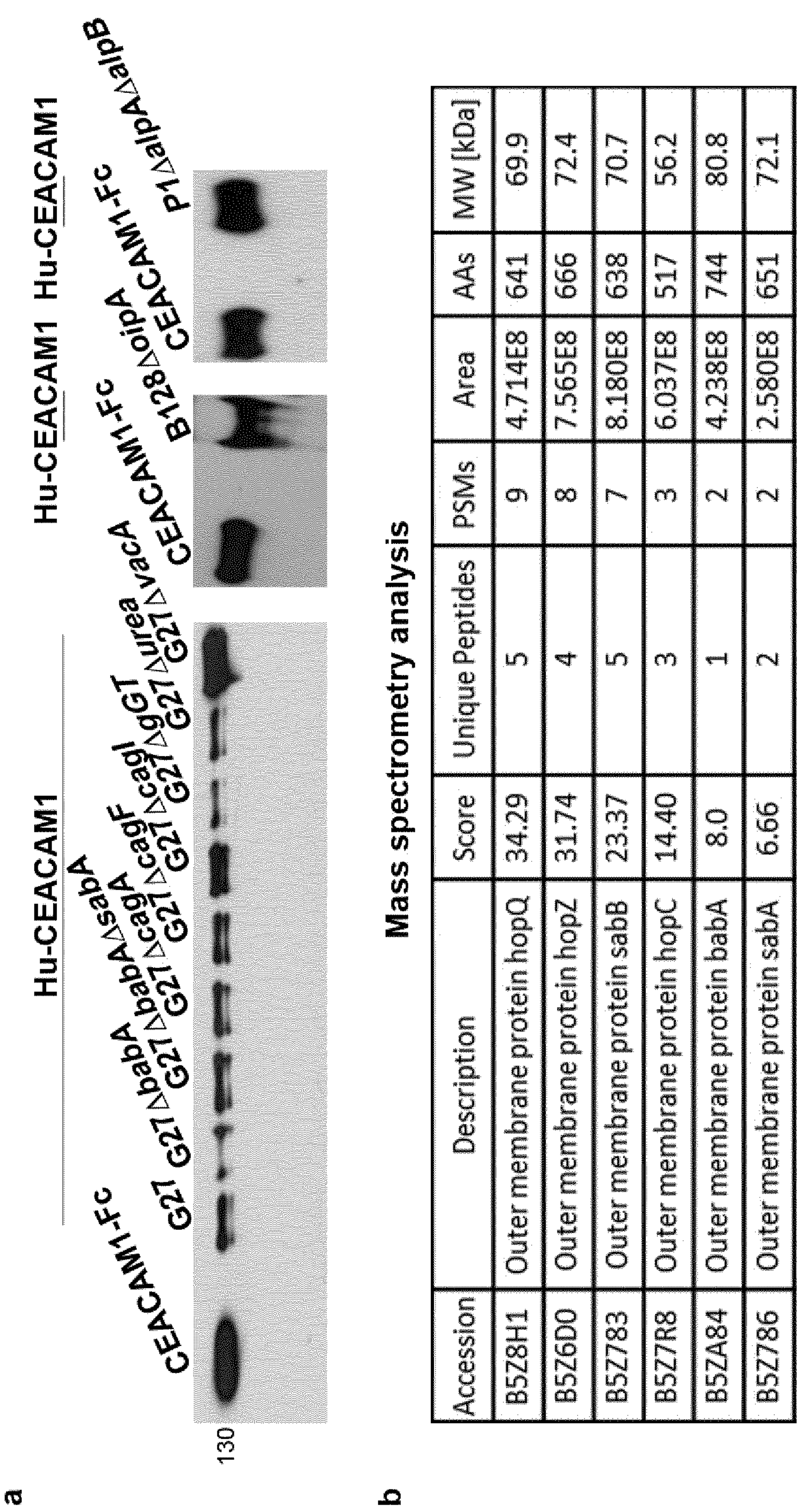
FIG. 5 shows that *H. pylori* binds to CEACAM1 via HopQ. (a) Pull down of various *H. pylori* knockout strains incubated with hu-CEACAM1-Fc. (b) Whole lysate of *H. pylori* strain G27 was incubated with hu-CEACAM1-Fc and precipitated with protein G sepharose. For mass spec analysis proteins were denatured, trypsin digested, the peptides analyzed via MS/MS and subsequently searched against the *H. pylori* G27 proteome. A selection of outer membrane proteins identified is shown. HopQ and HopZ, showing high Sequest scores, were further analyzed. (c) Pull down and western blot and FACS analysis of *H. pylori* strains P12, P12ΔhopQ and P12ΔhopZ binding to hu-CEACAM1-, CEACAM5- and CEACAM6-Fc.
Figure 5:
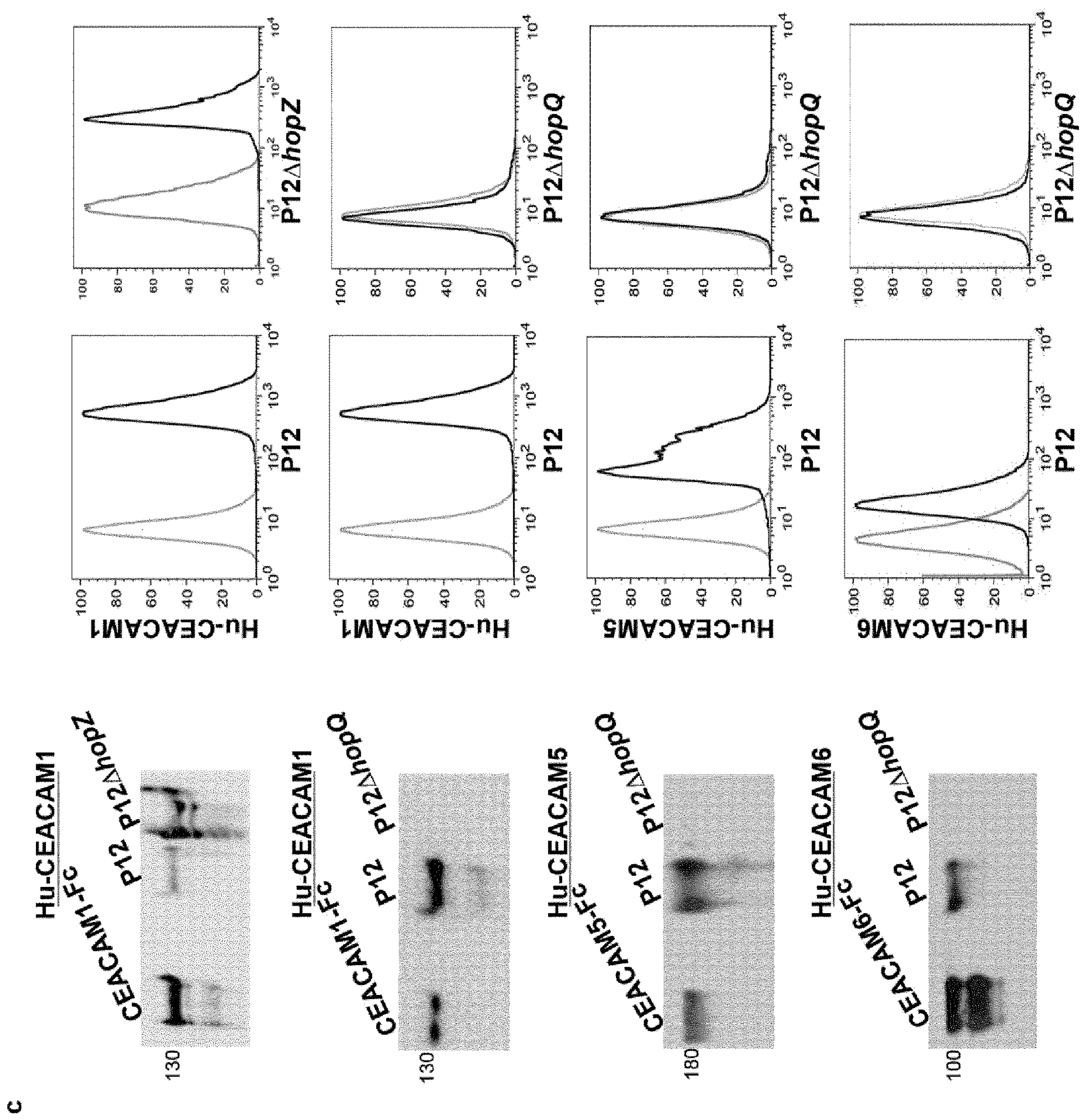

In order to identify the CEACAM-binding partner in *Helicobacter*, the inventors initially screened a number of *Helicobacter* mutants devoid of defined virulence factors that have been shown to be implicated in various modes of host cell interaction (BabA, SabA, AlpA/B, VacA, gGT, urease and the CagPAI). All of these mutants still bound to hu-CEACAM1 (FIG. 5*a*). Therefore, they established an immunoprecipitation approach (FIG. 6*a*) using *H. pylori* lysate and recombinant hu-CEACAM1-Fc coupled to protein G. Mass spectrometric analysis of the co-precipitate identified two highly conserved *H. pylori* outer membrane proteins as candidate CEACAM1 adhesins: HopQ and HopZ (FIG. 5*b*). Unlike a hopZ mutant, a hopQ deletion mutant was devoid of CEACAM1 binding (FIG. 5*c*). Importantly, the hopQ mutant was also unable to bind to CEACAM5 and 6 (FIG. 5*c*).

Figure 6:
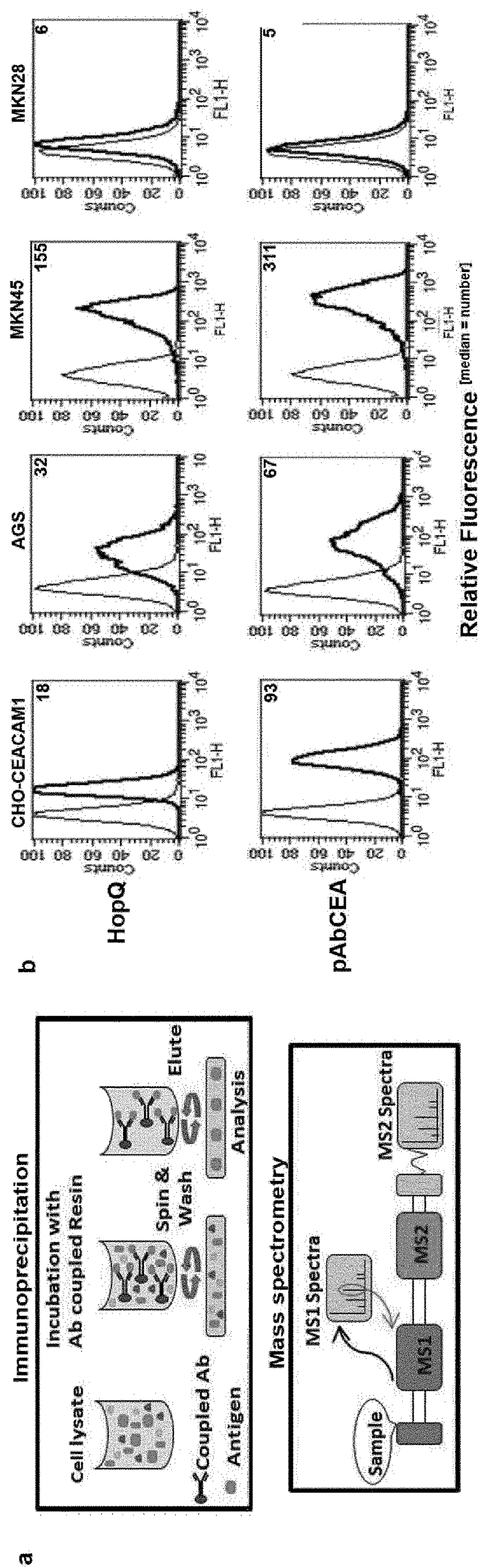
FIG. 6 relates to the identification of HopQ as hu-CEACAM interaction partner of *H. pylori*. (a) Whole lysate of *H. pylori* strain G27 was incubated with hu-CEACAM1-Fc and precipitated with protein G sepharose. For mass spectrometry analysis proteins were denatured, trypsin digested, the peptides analyzed via MS/MS and subsequently searched against the *H. pylori* G27 proteome. (b) CHO-CEACAM1, AGS, MKN45 and MKN28 were incubated with myc-His-tagged HopQ and subsequently with anti c-myc mAb followed by FITC conjugated goat anti-mouse F(ab')2. In parallel, the presence of CEACAMs was controlled by staining with rabbit-anti-CEA pAb (Dianova). Background fluorescence was measured by incubating the cells with control IgG antibody instead of HopQ protein or primary antibody (thin line). The samples were analyzed by flow cytometry. (c) Indicated CHO transfectants were incubated with HopQ and anti-CEA pAb as described above. Subsequently, samples were analyzed by flow cytometry (n=3). (d) The hopQ genes were collected from *H. pylori* isolates of all continents (NCBI database http://www.ncbi.nlm.nih.gov/). The MEGA6 program was applied to infer DNA relatedness using the Neighbor-Joining method. The Maximum Composite Likelihood method was utilized to compute evolutionary distances. The hopQ genes grouped into two major allelic variants (type I and II). The type I alleles are more diverse and were further divided into the two subgroupings type Ia and Ib, as indicated.
Figure 6:
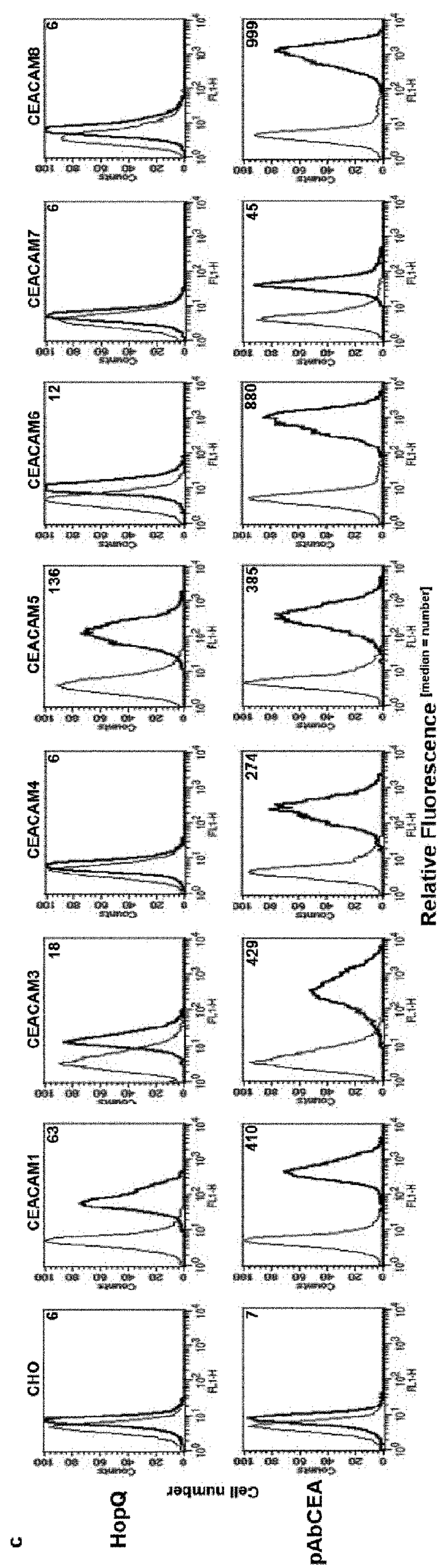
Figure 6:
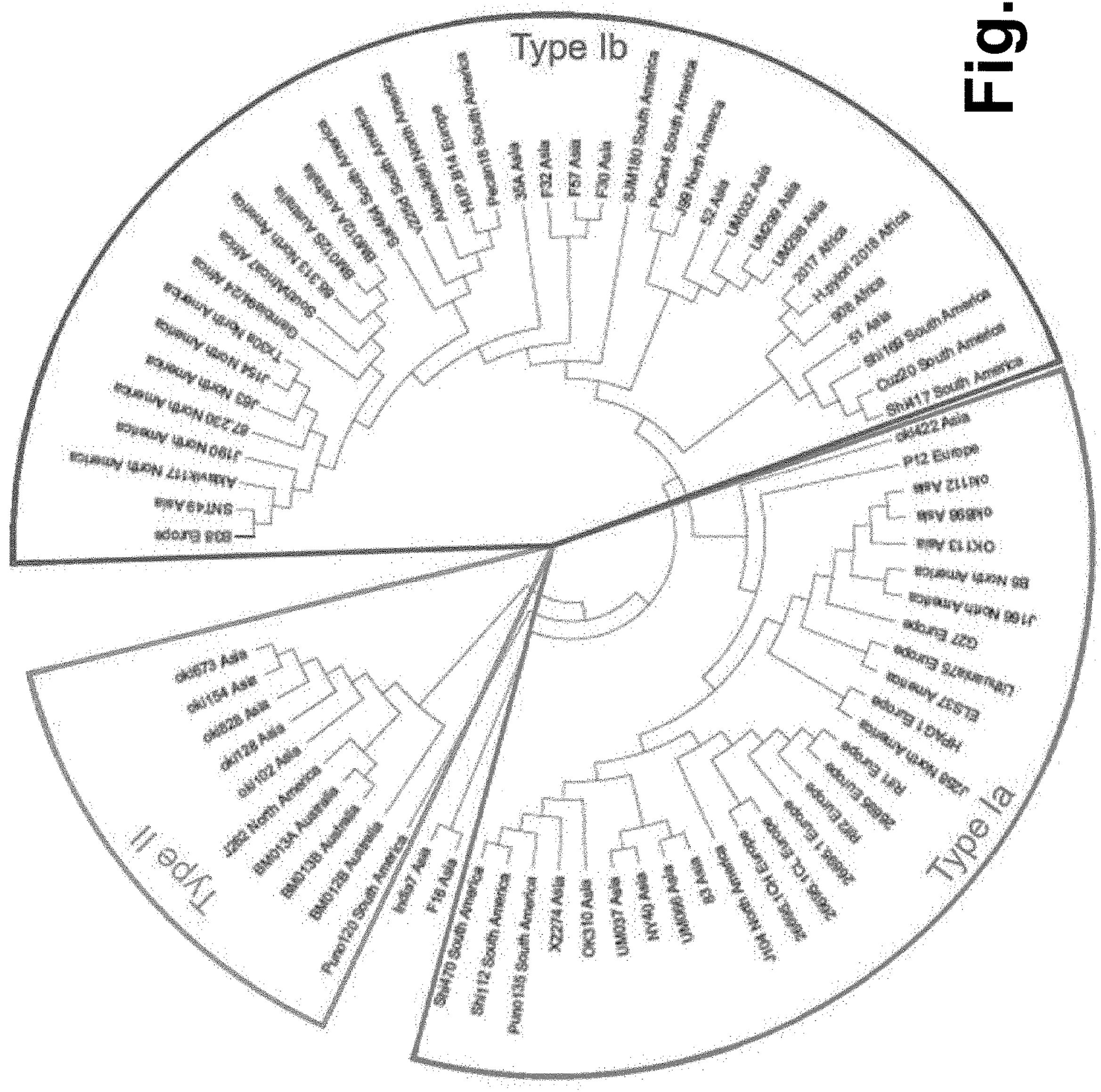

Next, the inventors tested the binding of recombinant HopQ to different gastric cancer cell lines and found that HopQ interacted with AGS and MKN45 both endogenously expressing CEACAMs (FIG. 6*b*). HopQ did not bind to the CEACAM negative cell line MKN28. Utilizing their CHO transfectants, the inventors found that the recombinant HopQ interacted preferentially with CEACAM1 and 5, and to lesser extent to CEACAM3 and 6. No binding was observed to CHO cells expressing either CEACAM4, 7, or 8 (FIG. 6*c*).

HopQ is a member of a *H. pylori*-specific family of outer membrane proteins, and shows no significant homology to other CEACAM-binding adhesins from other Gram-negative bacteria, i.e. Opa proteins or UspA1 from *Neisseria meningitidis* and *Neisseria gonorrhoeae* or *Moraxella catarrhalis*, respectively, and is therefore a novel bacterial factor hijacking CEACAMs. Like Opa and UspA1, HopQ targets the N-terminal domain in CEACAMs, an interaction the inventors found to require folded protein and to be dependent on CEACAM sequence, resulting in specificity for human CEACAM1, 3, 5 and 6. *H. pylori* hopQ (omp27; HP1177 in the *H. pylori* reference strain 26695) exhibits genetic diversity that represents two allelic families (Cao & Cover, 2002), type-I and type-II (FIG. 6*d*), of which the type-I allele is found more frequently in cag(+)/type s1-vacA strains. Both alleles share 75 to 80% nucleotide sequences and exhibit a homology of 70% at the amino acid level (Cao & Cover, 2002). The inventors observed allelic differences in HopQ's binding strength towards CEACAMs, whereby hopQ type-I alleles seem to bind stronger to CEACAM1, while type-II alleles, as found in strain TX30, favor CEACAM5 and 6. Importantly, hopQ genotype shows a geographic variation, with the hopQ type-I alleles more prevalent in Asian compared to Western strains; and was also found to correlate with strain virulence, with type-I alleles associated with higher inflammation and gastric atrophy.

Example 4

Structure and Binding Properties of the HopQ Adhesin Domain

Figure 7:
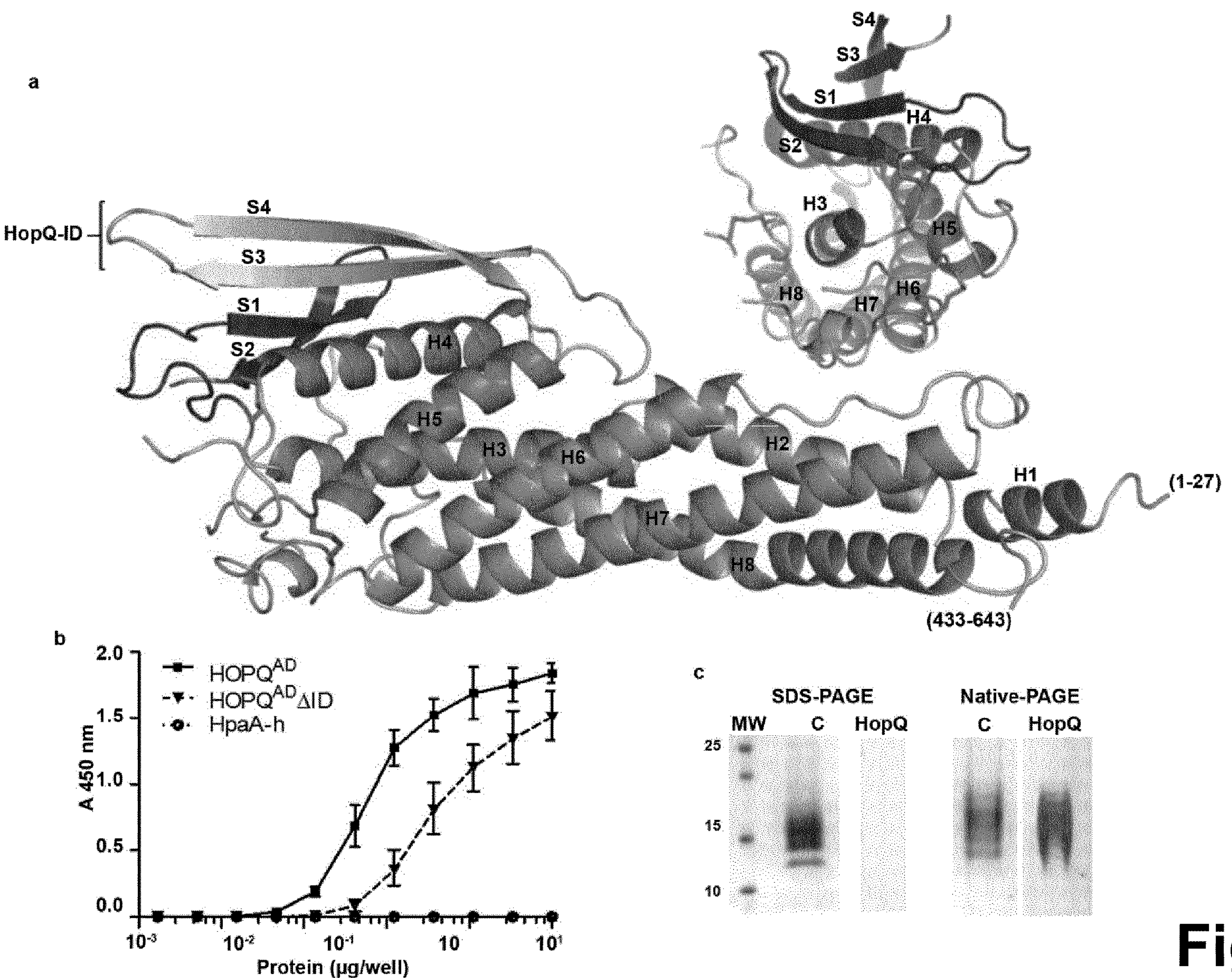
FIG. 7 shows the X-ray structure and binding properties of the HopQ adhesin domain. (a) Ribbon representation of the $HopQ^{AD}$ showing the 3+4-helix bundle topology seen also in the BabA and SabA adhesins (FIG. 8*d*). Three Cys pairs (Cys102-Cys131, Cys237-Cys269 and Cys361-Cys384) conserved in most Hop family members pinch off extended loops at the distal end of the HopQ adhesin domain, to form a common protein surface area with increased sequence diversity. Similar to the 4-stranded insertion domain of BabA (BabA-ID.

HopQ belongs to a paralogous family of *H. pylori* outer membrane proteins (Hop's), to which also the blood group antigen binding adhesins BabA and SabA belong. To gain insight into its structure-function relationship the inventors determined the X-ray structure of a HopQ fragment corresponding to its predicted extracellular domain (residues 17-443 of the mature protein, i.e., after removal of the signal peptide; $HopQ^{AD}$; FIG. 7*a* and Table 1). $HopQ^{AD}$ showed strong, dose dependent binding to the N-terminal domain of human CEACAM1 (C1ND; residues 35-142) in ELISA (FIG. 7*b*). Binding profiles measured by isothermal titration calorimetry (ITC) of $HopQ^{AD}$ titration with C1ND revealed a 1:1 stoichiometry with a dissociation constant Kd of 296±40 nM (FIG. 8*a*).

Figure 8:
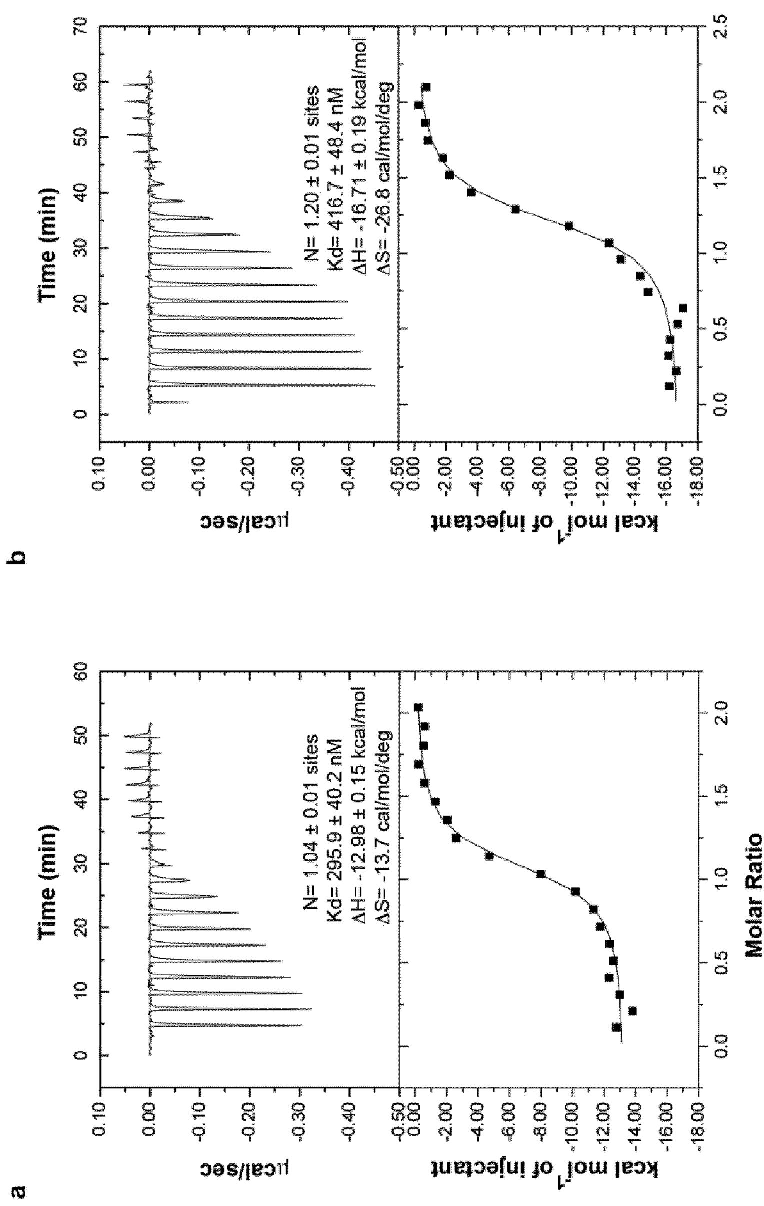
FIG. 8 shows isothermal titration calorimetry (ITC) of $HopQ^{AD}$-binding to the human CEACAM1 N-domain. ITC injection heats (upper) and normalized binding isotherm (lower) of 25 μM C1ND (a) or *E. coli* expressed C1ND (Ec-C1ND) (b) titrated with 250 μM $HopQ^{AD}$ show an equivalent equimolar interaction in presence or absence of N-glycosylation, respectively. Binding affinities and thermodynamic profiles are shown inset. (c) 2mFo-DFc electron density map contoured at 1.0 σ around the H5 helix of $HopQ^{AD}$. (d) Superimposition of the structures of $BabA_{1-527}$ (PDB accession code 4ZH0), $HopQ^{AD}$ and $SabA_{1-460}$ (PDB accession code 4O5J). Both the BabA and SabA structures show a kink in their N-terminal end to position them perpendicular to the core domain, however this change in orientation is missing in the HopQ structure. The α-helical core domain is conserved across all structures, whereas the 2-stranded insertion domain (ID) in HopQ is elongated by two additional β-strands in BabA. Previously, it was shown the ID of BabA to be responsible for adherence to blood group receptors. Strands and helices are named according to HopQ topology. (e) SDS-PAGE and schematic representation of the $HopQ^{AD}$ and $HopQ^{AD}\Delta$ID fragments used in this study. (f) Mean ELISA titers (n=4; ±s.d.) of $HopQ^{AD}$ or mutant $HopQ^{AD}$ lacking the HopQ-ID ($HopQ^{AD}\Delta$ID) binding to increasing concentrations of CEACAM5 or 8.
Figure 8:
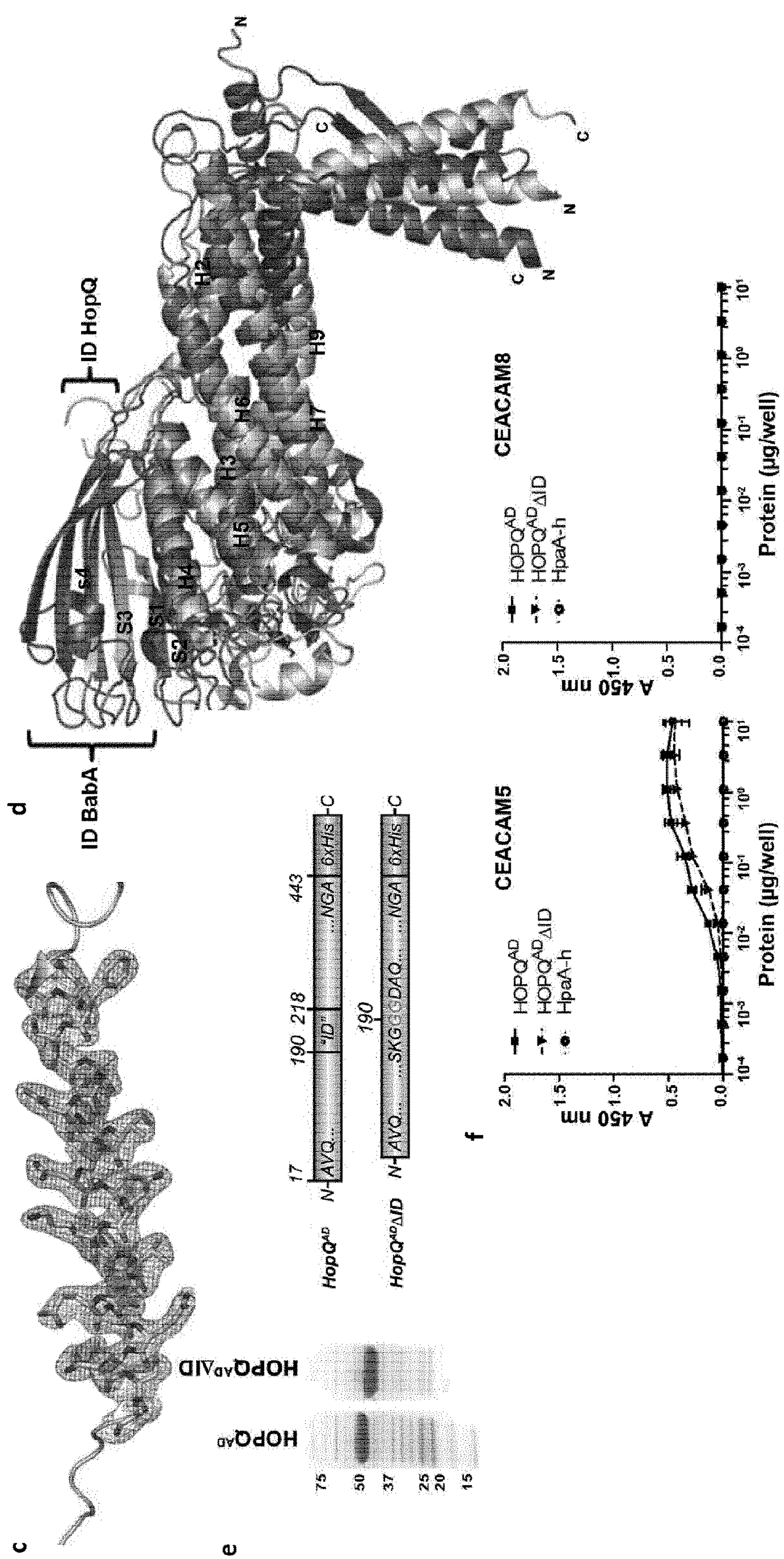

The $HopQ^{AD}$ X-ray structure shows that, like BabA and SabA, the HopQ ectodomain adopts a 3+4-helix bundle topology, though lacks the extended coiled-coil "stem" domain that connects the ectodomain to the transmembrane region (FIG. 8*d*). In BabA, the carbohydrate binding site resides fully in a 4-stranded beta-domain that is inserted between helices H4 and H5 (FIG. 8*d*). In HopQ, a 2-stranded beta-hairpin is found in this position (residues 180-218). Removal of the beta-hairpin resulted in a stable protein that showed a ~10 fold reduction of CEACAM1 binding affinity, indicating that although the HopQ insertion domain is implicated in binding, it does not comprise the full binding site as found in BabA (FIG. 7*b*). The BabA and SabA adhesins are lectins that bind Lewis b and sialylated Lewis x and a glycans, respectively. To verify if the HopQ-CEACAM interaction is similarly glycan-driven, the inventors evaluated HopQ binding to C1ND under native or denatured conditions. Far western analysis revealed that HopQ specifically bound folded, but not denatured CEACAM1-N (FIG. 7*c*). In contrast, bacterial pull-down experiments showed only a minor reduction in binding upon CEACAM1-Fc deglycosylation (FIG. 10, corroborating that protein-protein interactions form the major contributor to HopQ-CEACAM binding.

TABLE 1

Data collecton and refinement statistics for the $HopQ^{AD}$ structure.

| | $HopQ^{AD}$ |
|---|---|
| Data collection | |
| Space group | P 1 $2_1$ 1 |
| Cell dimensions | |
| a, b, c (Å) | 57.7, 57.7, 285.7 |
| α, β, γ (°) | 90.0, 90.1, 90.0 |
| Resolution (Å) | 49.38-2.6 (2.74-2.6)* |
| $R_{merge}$ | 14.7 (121.0)* |
| I/σI | 7.3 (0.9)* |
| CC½ | 99.3 (57.6)*‡ |
| Completeness (%) | 99.7 (98.2)* |
| Redundancy | 4.7 (4.5)* |
| Refinement | |
| Resolution (Å) | 285.6-2.6 |
| No. reflections | 55541 |
| $R_{work}/R_{free}$ | 20.9/23.6 |
| No. atoms | |
| Protein | 10946 |
| Water | 35 |
| B-factors | |
| Protein | 42.8 |
| Water | 60.7 |
| R.m.s deviations | |
| Bond lengths (Å) | 0.014 |
| Bond angles (°) | 1.71 |

*Highest resolution shell is shown in parenthesis.

‡Resolution limits were determined by applying a cut-off based on the mean intensity correlation coefficient of half-datasets (CC½) approximately of 0.5.

Example 5

HopQ—CEACAM1 Interaction Triggers Cell Responses

Figure 9:
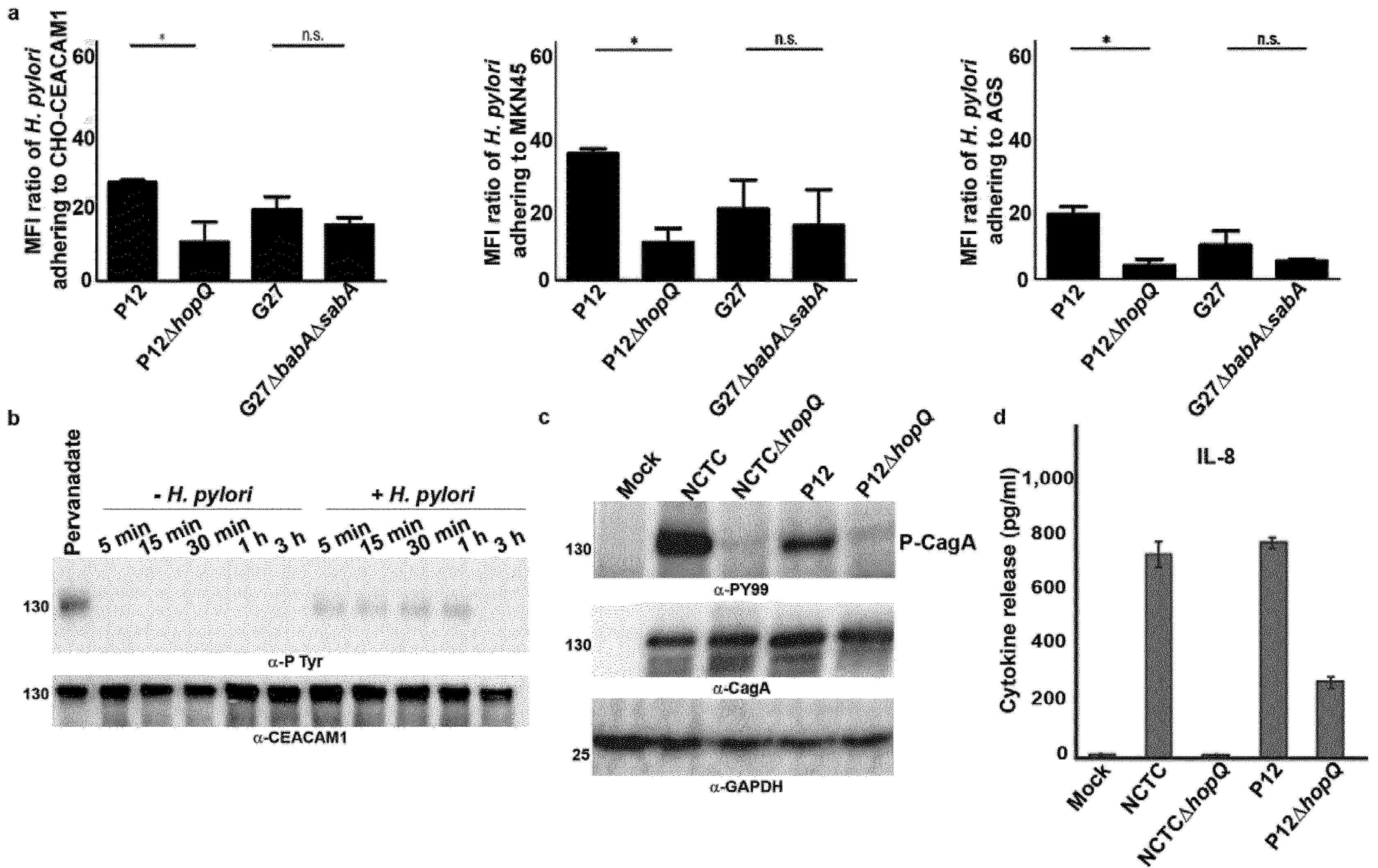
FIG. 9 shows that deletion of hopQ in *H. pylori* leads to reduced bacterial cell adhesion and abrogates CagA delivery, IL-8 release and cell elongation. (a) Flow cytometry analysis of CHO-hu-CEACAM1-L, MKN45 and AGS cells incubated with MOI 10 of CFSE-DA labeled bacterial strains P12, G27, P12ΔhopQ, and G27ΔbabAΔsabA (3 technical replicates). Mean±s.e.m are shown. Two-tailed t-test, *P≤0.03. (b) CHO-CEACAM1-L cells were incubated with and without *H. pylori*. Subsequently the Tyr-phosphorylation of CEACAM1 was analyzed by IP and western blot. Pervanadate treatment served as positive control, detection of CEACAM1 as loading control (bottom). (c) AGS cells were infected with P12, NCTC11637 and corresponding isogenic hopQ-mutants. The blot was probed with α-phosphotyrosine and α-CagA. (d) Generation of IL-8 by AGS determined by ELISA. (e) HA-tagged HEK293-hu-CEACAM1 transfectants infected with indicated *H. pylori* wt and knockout strains or NCTC11637ΔhopQ re-expressing wt hopQ gene. (f) Representative phase contrast micrographs of differently infected AGS. (g) AGS cells infected for 6 h with the P12, P12ΔhopQ or P12ΔhopQ/hopQ re-expressing wt hopQ gene (3 technical replicates). (h) AGS cells were pre-treated with 2, 5, 10 or 20 μg of α-CEACAM Ab per $4\times10^5$ cells (lanes 3-6). After 30 min incubation, MOI 20 of wild-type *H. pylori* was added to the cells. (i) Wild-type *H. pylori* was pre-treated with 2, 5, 10 or 20 μg of α-HopQ per $8\times10^6$ bacteria (lanes 3-6) and then added to the AGS cells. After 6 h of infection, the cells were photographed and harvested, followed by immunoblotting with α-PY99 and α-CagA. The bottom panels show the quantification of elongated AGS cells in each experiment in five different 0.25-$mm^2$ fields (3 technical replicates). Error bars show mean±s.d. (j) Pre-incubation of cells with a HopQ-derived peptide corresponding to the HopQ-ID (aa 190-218) inhibits HopQ-dependent phosphorylation of CagA and cell elongation at low micromolar concentration.
Figure 9:
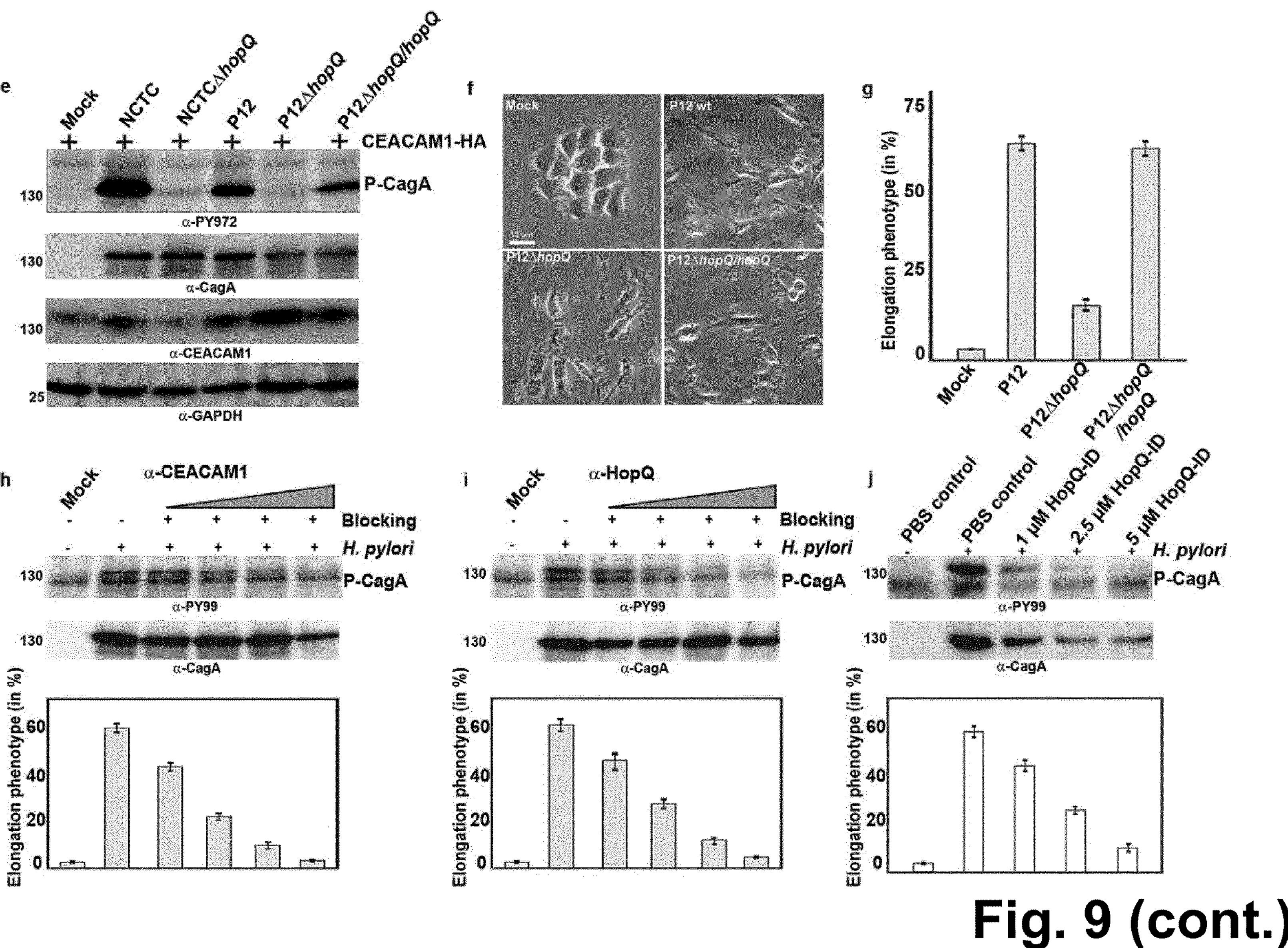

To further investigate how HopQ may influence adhesion and cellular responses, the inventors sought to establish cellular pathogenesis models in which the HopQ-CEACAM-mediated adhesion could be analyzed. Therefore, the inventors characterized various gastric cell lines typically employed for *H. pylori* in vitro experiments regarding their expression of CEACAMs, and observed that MKN45, KatoIII and AGS did express CEACAM1, CEACAM5 and CEACAM6, whereas MKN28 showed no presence of CEACAMs (FIGS. 10*a* and *b*). CHO cells were stably transfected with CEACAM1-L (containing the ITIM motif). Upon infection with *H. pylori* wild-type strain P12 and its isogenic hopQ deletion mutant, the inventors observed a significantly reduced adherence to CHO-CEACAM1-L, MKN45 and AGS cells, while strains deficient in the adhesins BabA and SabA showed only slightly reduced adhesion (FIG. 9*a*). In CHO-CEACAM1-L cells, the inventors observed tyrosine-phosphorylation of the CEACAM1 ITIM domain upon exposure to *H. pylori*, which was apparent within 5 minutes, and was maintained for up to 1 hour (FIG. 9*b*). Phosphorylation of the CEACAM1 ITIM domain is a well-known initial event triggering SHP1/2 recruitment inducing downstream signaling cascades. Contact-dependent signaling through CEACAMs is a common means of modulating immune responses related to infection, inflammation and cancer, and these immune-dampening cascades likely reflect the multiple independent emergence of non-homologous CEACAM-interacting proteins in diverse mucosal Gram-negative pathogens including *Neisseria, Haemophilus, Escherichia, Salmonella, Moraxella* sp. For *H. pylori*, interaction with human CEACAM1 through HopQ may represent a critical parameter for immunomodulatory signaling during colonization and chronic infection of man.

Additionally, hopQ mutant *H. pylori* strains showed an almost complete loss of T4SS-dependent CagA translocation (FIG. 9*c*) and strongly reduced IL-8 induction (FIG. 9*d*), while loss of other known adhesins had no effect on CagA delivery (FIGS. 10*c* and *d*).

To corroborate these data in an independent model and compensate for potential clonal effects in stably transfected cells, the inventors transiently transfected HEK293 cells with human CEACAM (1-L, 3, 4, 5, 6, 7, 8) expression plasmids. Infection of these cells confirmed the defect in CagA translocation observed in CHO-CEACAM1-L cells, which was restored upon complementation of the hopQ mutant strain (P12ΔhopQ/hopQ) (FIG. 9*e* and FIG. 10*e*). Also, cellular elongation, the so called "hummingbird phenotype", was significantly reduced upon deletion of hopQ (FIGS. 9*f* and *g*). Further, the inventors observed that *H. pylori* modulates important host transcription factors such as Myc, STAT3, CreATF2/CREB, GRE and NF-κB in a hopQ-dependent fashion (FIG. 10*f*). These results reveal that HopQ-CEACAM binding leads to direct and indirect alterations in host cell signaling cascades, and start to shed light on these HopQ-associated virulence landscapes. Given the importance of these signaling events for gastric carcinogenesis, the inventors explored if the CEACAM-HopQ interaction could be targeted in order to prevent CagA translocation and downstream effects. Indeed, using an α-CEACAM1 antibody, α-HopQ antiserum or a HopQ-derived peptide corresponding to the Hop-ID (aa 190-218) reduced CagA translocation in a dose dependent manner (FIG. 9*h-j*), but not corresponding controls (FIG. 10*g*). These data demonstrate that the HopQ-CEACAM1 interaction is necessary for successful translocation of the oncoprotein CagA into epithelial cells as well as modulation of inflammatory signaling, and that interference with this interaction can prevent CagA translocation, giving an indication of the translational potential of HopQ targeting *H. pylori* vaccination or immunotherapy.

Example 6

Figure 11:
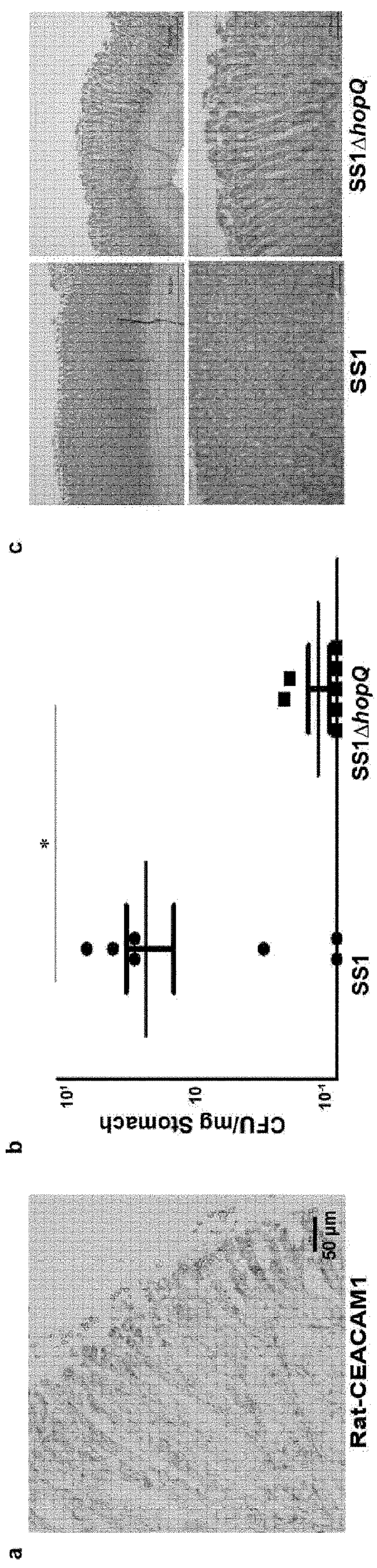
FIG. 11 shows that *H. pylori* colonization of rat stomach depends on HopQ. (a) IHC staining of rat stomach for rat-CEACAM1. (b) Male Sprague dawley rats (Data is from one experiment with 8 rats per group) were orally infected two times with SS1 and SS1ΔhopQ strains. Mean±s.e.m are shown. Two-tailed t-test, * P=0.02. (c) Hematoxylin/eosin staining of infected rat stomachs.
Figure 12:
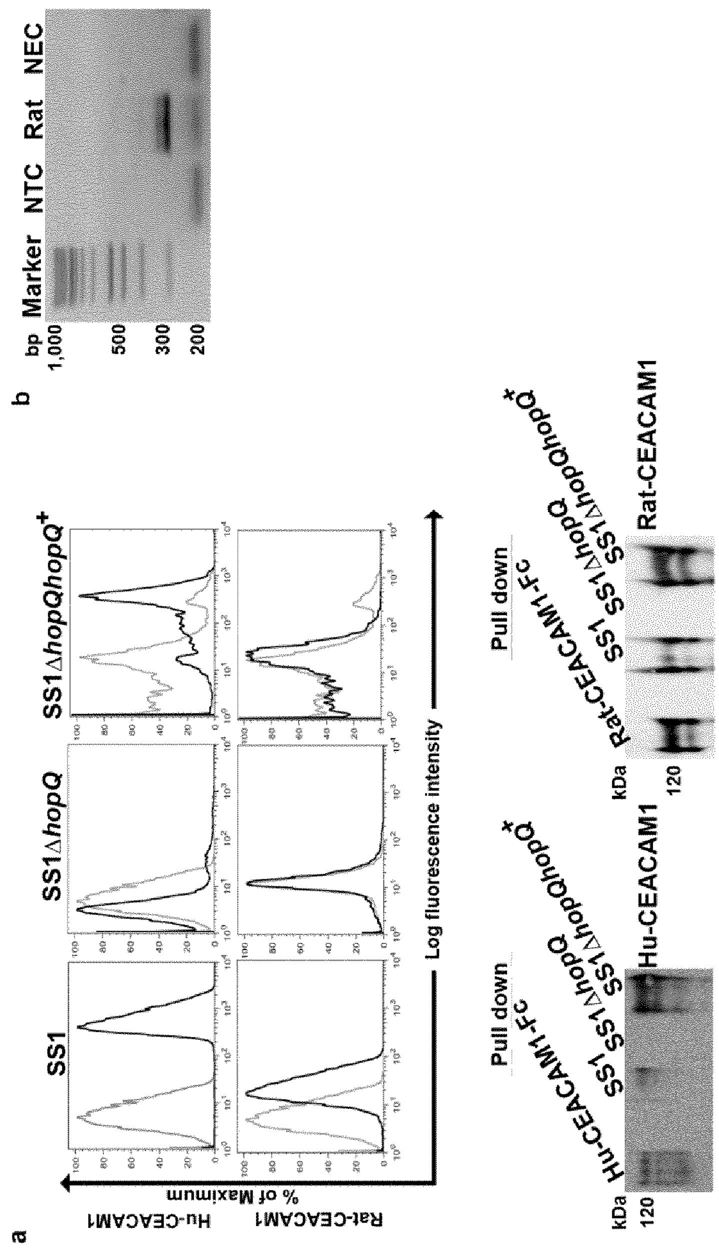
FIG. 12 shows that only the SS1 strain of *H. pylori* can colonize rat stomachs. (a) Pull down experiments with *H. pylori* wt strain SS1, SS1ΔhopQ, SS1ΔhopQ re-expressing wt hopQ gene and hu-CEACAM1-Fc and rat-CEACAM1-Fc analyzed by flow cytometry and western blot. (b) Expression of rat-CEACAM1 in RNA isolated of rat stomach biopsy. NTC: no template control, NEC: no enzyme control.

Deletion of HopQ Abrogates Colonization in a Rat Model of *H. pylori* Infection As the inventors found binding of HopQ to human and rat, but not to mouse CEACAM, they determined the role of HopQ in vivo, using a rat model of *H. pylori* infection. Having observed that CEACAM1 was expressed in normal rat stomach (FIG. 11a and FIG. 12b), the inventors infected rats with different *H. pylori* strains known to infect rodents. While all strains bound to rat CEACAM1 in vitro, only SS1 was able to efficiently colonize rats (FIG. 12a). The hopQ deficient SS1 strain was not able to colonize rats at detectable levels, and could not induce an inflammatory response in comparison to the wild type SS1 strain (FIGS. 11b and c). Therefore, in this model, HopQ seems also to serve as an important factor to mediate *H. pylori* colonization.

Example 7

Structure of a $HopQ^{AD}$ and C1ND Complex

Figure 13:
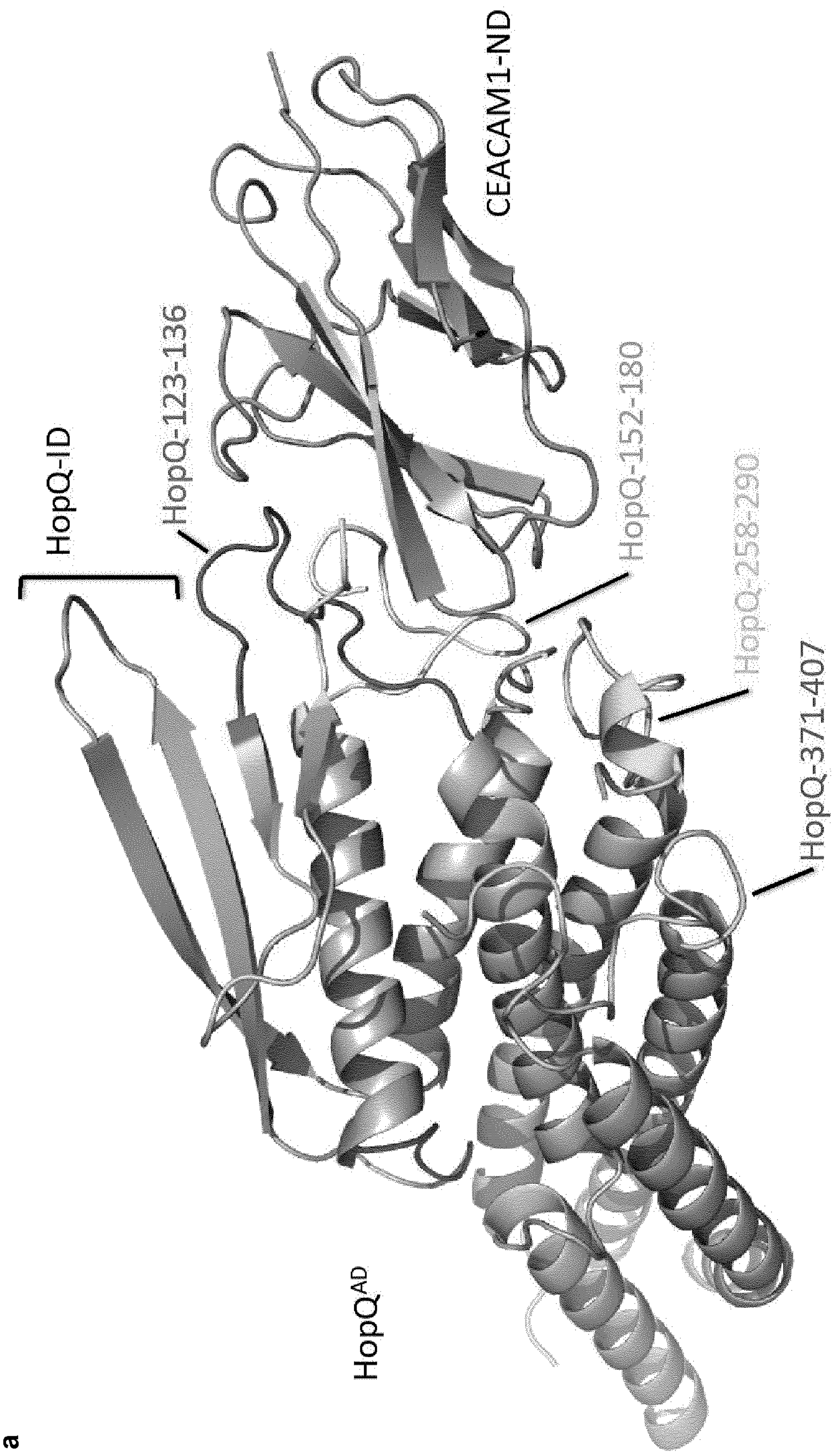
FIG. 13(*a*) shows the X-ray structure of the HopQ adhesin domain ($HopQ^{AD}$) bound to the N-terminal domain of human CEACAM1 (huCEACAM1-ND). The HopQ loops forming the contact interface with the CEACAM1-ND comprise residues 123-136 (loop A), residues 152-180 (loop B) and residues 258-290 (loop C) of SEQ ID NO: 15 (HopQ of strain P12). The HopQ insertion domain (see, for example, residues 210 to 238 of SEQ ID NO: 1) and loop 371-407 (loop D) of SEQ ID NO: 15 are adjacent to the direct binding interface. Antibodies raised against peptides laying inside or adjacent to the CEACAM-binding interface will have a neutralizing action, inhibiting the HopQ-CEACAM association by steric hindrance. (b) Representative sequences as found in *H. pylori* strain P12 as well as consensus sequences for the four loops. The consensus sequences are based on a multiple sequence alignment of 87 representative HopQ alleles from different clinical *H. pylori* isolates, wherein the height of the bars above the individual amino acids indicate the degree of identity among HopQ alleles. Sequence conservation logos show the possible amino acid sequence variation in the respective loops, wherein the height of the amino acid single letter symbol is representative of its probability.
Figure 13:
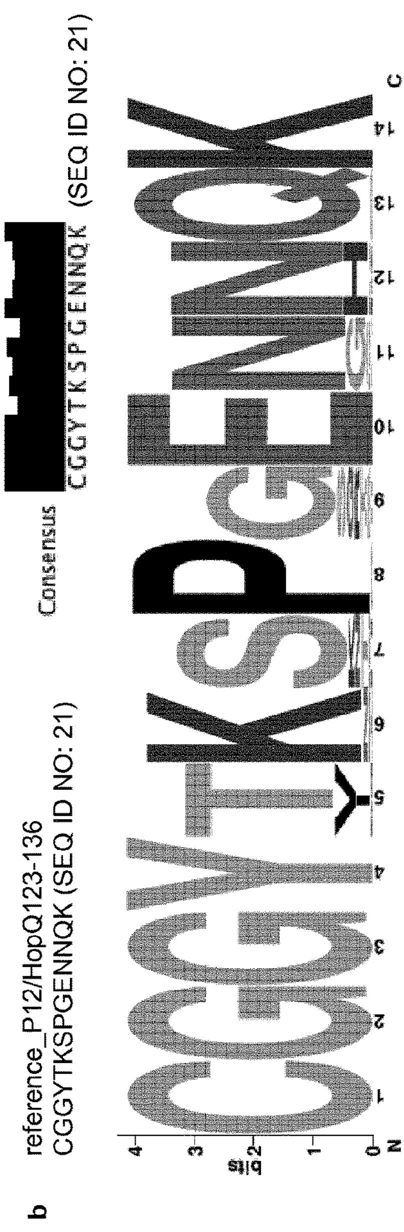
Figure 13:
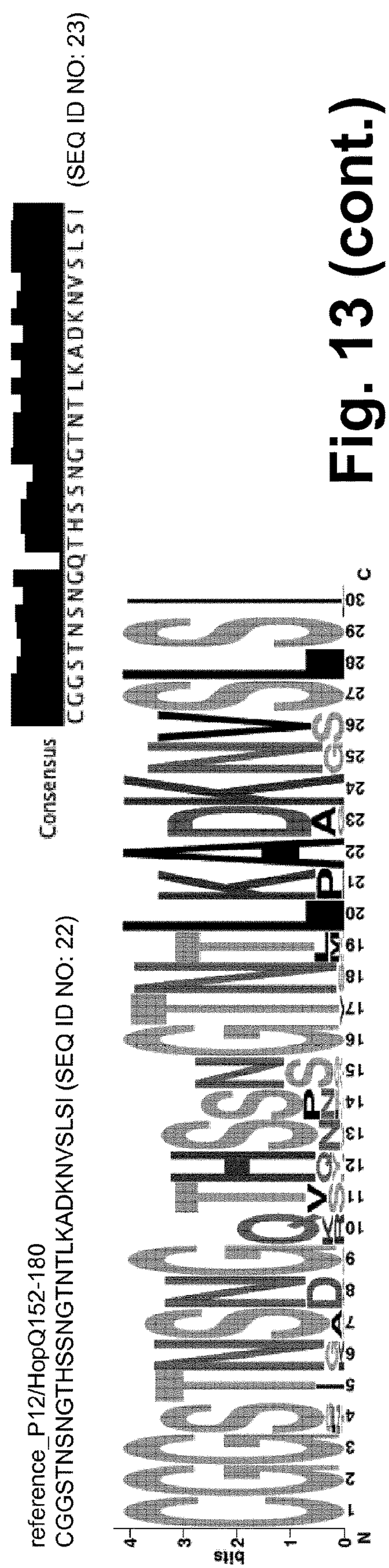
Figure 13:
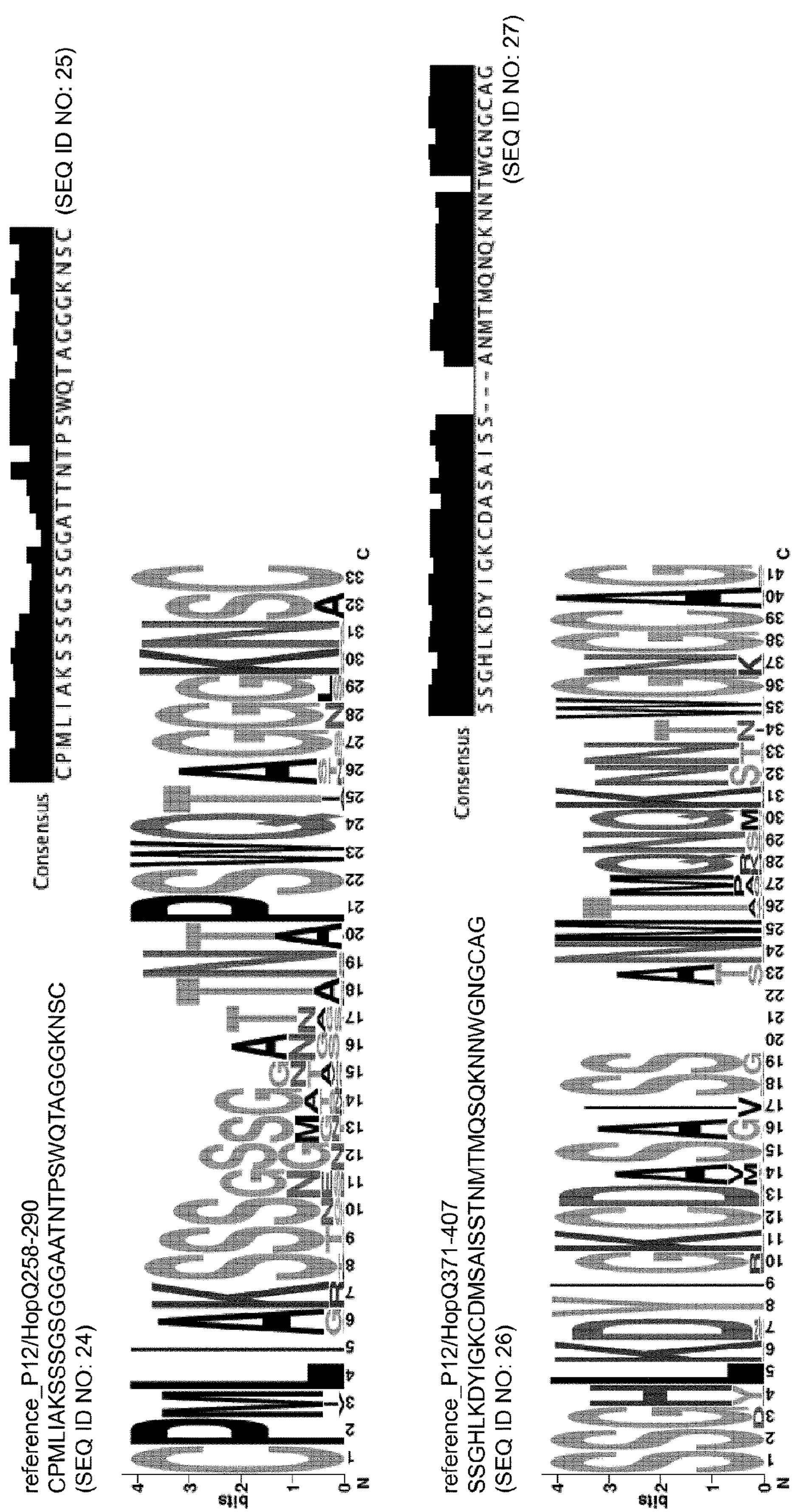

The structure of a complex between the HopQ adhesin domain and non-glycosylated N-terminal domain of human CEACAM1 recombinantly produced and purified from *E. coli* was determined (FIG. 13a and Table 2). The structure shows that the contact surface of HopQ that binds the CEACAM N-terminal domain is formed by three extended loops: HopQ_123-136 (loop A), HopQ_152-180 (loop B) and HopQ_258-290 (loop C). The binding conformation of loop HopQ_123-136 is stabilized by main chain hydrogen bonding with the β-hairpin formed by the HopQ-ID. Accordingly, deletion of the HopQ-ID was found to result in a drastic reduction in HopQ-CEACAM binding. A fourth extended loop on the HopQ adhesin domain, HopQ_371-407 (loop D), lies adjacent to the HopQ-CEACAM binding interface. Although no direct contact is made between HopQ_371-407 and the CEACAM N-domain, antibodies or antibody derivatives that bind HopQ_371-407 will disrupt the HopQ-CEACAM interaction by steric hindrance.

TABLE 2

Data collection and refinement statistics for the $HopQ^{AD}$-hC1ND structure.

| | $HopQ^{AD}$-hC1ND |
|---|---|
| Data collection | |
| Space group | C2 |
| Cell dimensions | |
| a, b, c (Å) | 118.0, 174.0, 118.1 |
| α, β, γ (°) | 90.0, 118.4, 90.0 |
| Resolution (Å) | 50.00-3.55 (3.64-3.55)* |
| $R_{merge}$ | 11.8 (88.0)* |
| I/σI | 8.0 (1.6)* |
| CC½ | 99.5 (59.7)* |
| Completeness (%) | 99.3 (99.5)* |
| Redundancy | 3.8 (3.8)* |
| Refinement | |
| Resolution (Å) | 48.81-3.55 |
| No. reflections | 25252 |
| $R_{work}/R_{free}$ | 28.1/33.8 |
| No. atoms | |
| Protein | 9621 |
| Water | 0 |
| B-factors | |
| Protein | 81.5 |
| Water | NA |
| R.m.s deviations | |
| Bond lengths (Å) | 0.008 |
| Bond angles (°) | 1.12 |

*Highest resolution shell is shown in parenthesis.

‡ Resolution limits were determined by applying a cut-off based on the mean intensity correlation coefficient of half-datasets (CC½) approximately of 0.5.

Materials and Methods

Bacteria and Bacterial Growth Conditions

The *H. pylori* strains G27, PMSS1, SS1, J99 (ATCC, 700824), 2808, 26695 (ATCC, 70039), TX30, 60190, P12, NCTC11637 (ATCC, 43504), Ka89 and *H. bilis* (ATCC43879) were grown on Wilkins-Chalgren blood agar plates under microaerobic conditions (10% CO2, 5% O2, 8.5% N2, and 37° C.). *H. suis* and *H. heilmannii* were grown on *Brucella* agar and *H. felis* (ATCC 49179) and *H. bizzozeronii* on brain-heart infusion (BHI) agar supplemented with 10% horse blood. *Moraxella catarrhalis* (ATCC, 25238), *Moraxella lacunata* (ATCC 17967) and *Campylobacter* jejunei (ATCC, 33560) were cultured on brain-heart infusion (BHI) agar supplemented with 5% heated horse blood overnight at 37° C. in a $CO_2$ incubator. The generation of an isogenic ΔhopQ mutant was done by replacement of the entire gene by a chloramphenicol resistance cassette as described (Belogolova et al., 2013).

Production of CEACAM Proteins

The cDNA, which encodes the extracellular domains of human CEACAM1-Fc (consisting of N-A1-B1-A2 domains), human CEACAM1dN-Fc (consisting of A1-B1-A2), rat CEACAM1-Fc (consisting of N-A1-B1-A2), rat CEACAM1dN-Fc (consisting of A1-B1-A2), human CEACAM3-Fc (consisting of N), human CEACAM6-Fc (consisting of N-A-B), human CEACAM8-Fc (consisting of N-A-B), respectively, were fused to a human heavy chain Fc-domain and cloned into the pcDNA3.1(+) expression vector (Invitrogen, San Diego, Calif.), sequenced and stably transfected into HEK293 (ATCC CRL-1573) cells as described (Singer et al., 2014). The Fc chimeric CEACAM-Fc proteins were accumulated in serum-free Pro293s-CDM medium (Lonza) and were recovered by Protein A/G-Sepharose affinity Chromatography (Pierce). Proteins were analyzed by SDS-PAGE and stained by Coomassie blue demonstrating an equal amount and integrity of the produced fusion proteins (FIG. 2i). Recombinant-human CEACAM5-Fc was ordered from Sino Biological Inc. For production of the recombinant human CEACAM1 N-Domain (C1ND), the annotated domain (UniProt ID: P13688) was first backtranslated using the GeneOptimizer® (LifeTechnologies) and the leader sequence of the Igk-chain as well as a C-terminal Strep-Tag II was added. The gene was synthesized and seamlessly cloned into pCDNA3.4-TOPO (LifeTechnologies). Protein was produced in a 2 L culture of Expi293 cells according to the Expi293 expression system instructions (LifeTechnologies). The resulting supernatant was concentrated and diafiltered against ten volumes of 1× SAC buffer (100 mM Tris, 140 mM NaCl, 1 mM EDTA, pH 8.0) by crossflow-filtration, using a Hydrosart 5 kDa molecular-weight cutoff membrane (Sartorius). The retentate was loaded onto a StrepTrap HP column (GE Healthcare) and eluted with 1× SAC supplemented with 2.5 mM D-Desthiobiotin (IBA). The protein was stored at +4° C.

For the bacterial expression of the C1ND (Ec-C1ND), the amino acid sequence was codon-optimized for expression in *E. coli*, synthesized by GeneArt de novo gene synthesis (Life Technologies), and cloned with a C-terminal His6 tag in the pDEST™ 14 vector using Gateway technology (Invitrogen). *E. coli* C43(DE3) cells were transformed with the resulting construct and grown in LB supplemented with 100 µg/mL ampicillin at 37° C. while shaking. At $OD_{600}$=1, Ec-C1ND expression was induced with 1 mM IPTG overnight at 30° C. Cells were collected by centrifugation at 6.238 g for 15 minutes at 4° C. and resuspended in 50 mM Tris-HCl pH 7.4, 500 mM NaCl (4 mL/g wet cells) supplemented with 5 µM leupeptin and 1 mM AEBSF, 100 µg/mL lysozyme, and 20 µg/mL DNase I. Subsequently, cells were lysed by a single passage in a Constant System Cell Cracker at 20 kPsi at 4° C. and debris was removed by centrifugation at 48.400 g for 40 minutes. The cytoplasmic extract was filtrated through a 0.45 μm pore filter and loaded on a 5 mL pre-packed Ni-NTA column (GE Healthcare) equilibrated with buffer A (50 mM Tris-HCl pH 7.4, 500 mM NaCl and 20 mM imidazole). The column was then washed with 40 bed volumes of buffer A and bound proteins were eluted with a linear gradient of 0-75% buffer B (50 mM Tris-HCl pH 7.4, 500 mM NaCl and 500 mM imidazole). Fractions containing Ec-C1ND, as determined by SDS-PAGE, were pooled and concentrated in a 10 kDa MW cutoff spin concentrator to a final volume of 5 ml. To remove minor protein contaminants, the concentrated sample was injected onto the Hi-Prep™ 26/60 Sephacryl S-100 HR column (GE Healthcare) pre-equilibrated with a buffer containing 50 mM Tris-HCl pH 8.0, 150 mM NaCl. Fractions containing the Ec-C1ND complex were pooled and concentrated using a 10 kDa MW cutoff spin concentrator.

$HopQ^{AD}$ and $HopQ^{AD}$ΔID Cloning, Production and Purification

In order to obtain a soluble HopQ fragment, the HopQ gene from the *H. pylori* G27 strain (accession No. CP001173 Region: 1228696 . . . 1230621; SEQ ID NO: 1) was used and a HopQ fragment ranging from residues 37-463 was produced (residues 17-443 of the mature protein), thus removing the N-terminal 13-strand and signal peptide, as well as the C-terminal β-domain expected to represent the TM domain. In $HopQ^{AD}$ΔID, the amino acids 190-218 of the mature protein were replaced by two glycines (FIG. 8*e*). DNA coding sequences corresponding to the HopQ type I fragments was PCR-amplified from *H. pylori* G27 genomic DNA using primers (forward: GTTTAACTTTAAGAAGGAGATATACAAATGGCGGTTCAAAAAGTGAAAAACGC (SEQ ID NO: 8); reverse: TCAAGCTTATTAATGATGATGATGATGGTGGGCGCCGTTATTCGTGGTTG (SEQ ID NO: 9)), containing a 30 bp overlap to the flanking target vector sequences of pPRkana-1, a derivative of pPR-IBA 1 (IBA GmbH) with the ampicillin resistance cassette replaced by the kanamycin resistance cassette, under a T7 promotor. In parallel, the vector was PCR-amplified using primers (forward: CACCATCATCATCATCATTAATAAGCTTGATCCGGCTGCTAAC (SEQ ID NO: 10); reverse: GTTTAACTTTAAGAAGGAGATATACAAATG (SEQ ID NO: 11)), using the same overlapping sequences in reversed orientation. The forward primer additionally carried the sequence for a 6× His-tag. The amplicons were seamlessly cloned using Gibson Assembly (New England Biolabs GmbH). Based on codon optimized $HopQ^{AD}$ plasmid, the $HopQ^{AD}$ΔID constructs were cloned. The plasmids were amplified by 5' phosphorylated primers (forward: GGTGACGCTCAGAACCTGCTGAC (SEQ ID NO: 12); reverse: ACCACCTTTAGAGTTCAGCGGAG (SEQ ID NO: 13)) replacing the ID region by two glycines, DpnI (NEB) digested and blunt-end ligated by T4 ligase (NEB).

*Escherichia coli* BL21 (DE3) cells (NEB GmbH) were transformed with the pPRkana-1 constructs, grown at 37° C. with 275 rpm on auto-inducing terrific broth (TRB) according to {Studier:2005ku}, supplemented with 2 mM $MgSO_4$, 100 mg/L Kanamycin-Sulfate (Carl Roth GmbH+Co. KG), 0.2 g/L PPG2000 (Sigma Aldrich) and 0.2% w/v Lactose-monohydrate (Sigma Aldrich), until an OD of 1-2 was reached. Afterwards, the temperature was lowered to 25° C. and auto-induced overnight, reaching a final OD of 10-15 the following morning. Cells were harvested by centrifugation at 6000 g for 15 min at 4° C. using a SLA-3000 rotor in a Sorvall RC-6 Plus centrifuge (Thermo Fischer). Prior to cell disruption, cells were resuspended in 10 ml cold NiNTA buffer A (500 mM NaCl, 100 mM Tris, 25 mM Imidazole, pH 7.4) per gram of biological wet weight (BWW), supplemented with 0.1 mM AEBSF-HCl, 150 U/g BWW DNase I and 5 mM $MgCl_2$ and dispersed with an Ultra-Turrax T25 digital (IKA GmbH+Co. KG). Cell disruption was performed by high-pressure homogenization with a PANDA2000 (GEA Niro Soavi) at 800-1200 bar in 3 passages at 4° C. The cell lysate was clarified by centrifugation at 25000 g for 30 min at 4° C. in a SLA-1500 rotor and remaining particles removed by filtration through a 0.2 μM filter. HopQ fragments were purified by consecutive nickel affinity and size exclusion chromatography. Briefly, the clarified cell lysate was loaded onto a 5 ml pre-packed Ni-NTA HisTrap FF crude column (GE Healthcare) pre-equilibrated with buffer A, washed with ten column volumes (CV) of buffer A and the bound protein eluted with a 15 CV linear gradient to 75% NiNTA buffer B (500 mM NaCl, 100 mM Tris, 500 mM Imidazole, pH 7.4). Eluted peak fractions were collected, pooled and concentrated to a final concentration of 8-10 mg $ml^{-1}$ using a 10 kDa molecular-weight cutoff spin concentrator. Subsequently, 5 ml of the concentrated protein were loaded onto a HiLoad 16/600 Superdex 75 pg column (GE Healthcare) pre-equilibrated with Buffer C (5 mM Tris, 140 mM NaCl, pH 7.3) and eluted at 1 ml $min^{-1}$. Finally, only protein corresponding to the monomer-peak was pooled and stored at +4° C. prior to crystallization. For analyzing the multimerization state of $HopQ^{AD}$, SEC was performed on a Superdex 200 10/300 GL (GE Healthcare) with 24 ml bed volume. The column was pre-equilibrated with Buffer C and subsequently, 25 μg protein injected and separated with a flow rate of 0.5 ml/min.

The HopQ insertion domain (HopQ-ID) representing peptide was HA-tagged, synthesized (EKLEAHVTTSKYQQDNQTKTTTSVIDTTNYPYDVPDYA (SEQ ID NO: 14, HA-tag underlined))

and HPLC purified (Peptide Specialty Laboratories, Heidelberg, Germany). For cellular assays, the lyophilized peptide was dissolved in sterile PBS to a concentration of 1 mM and dialysed with a 0.1-0.5 kDa molecular-weight cutoff membrane against PBS to remove remaining TFA. The peptide solution was stored at −20° C. until further use.

TABLE 3

HopQ sequences.

| Protein | *H. pylori* Strain | UniProt ID | UniProt Reference Cluster 90% sequence identity (July 2016) | SEQ ID NO (Protein/DNA) | Comment(s) |
|---|---|---|---|---|---|
| HopQ Type I | G27 | — | — | 1/2 | Accession No. CP001173, Region: 1228696 . . . 1230621 |
| HopQ Type I | 26695 | O25791 | 173 | 3/4 | Also referred to as Omp27 and HP1177 |
| HopQ Type I | P12 | H6A3H4 | 173 | 15/16 | — |
| HopQ Type II | Tx30a | Q8GDI6 | 77 | 5/6 | — |
| trxA (reference) | J99 | P66929 | 231 | — | — |

Detection of the HopQ-CEACAM Interaction by ELISA

For detection of the interaction between CEACAM and HopQ$^{AD}$, recombinant C1ND (1 μg/ml) in PBS was coated over night at 4° C. onto a 96-well immunoplate (Nunc MaxiSorb). Wells were blocked with SmartBlock (Candor) for 2 h at RT. Subsequently, HopQ fragments were added in a fivefold series dilution ranging from 10 μg/ml to 0.05 ng/ml for 2 h at room temperature. Next, an α-6×His-HRP conjugate (clone 3D5, LifeTechnologies) was diluted 1:5000 and incubated for 1 h at room temperature. For detection, 1-Step™ Ultra TMB-ELISA Substrate Solution (LifeTechnologies) was used and the enzymatic reaction was stopped with 2N $H_2SO_4$. Washing (3-5×) in between incubation steps was carried out with PBS/0.05% Tween20.

Isothermal Titration Calorimetry

ITC measurements were performed on a MicroCal iTC200 calorimeter (Malvern). Either HopQ$^{AD}$ type I (50 μM) or C1ND (25 μM) was loaded into the cell of the calorimeter and respectively CEACAM (50 μM or 500 μM) or HopQ$^{AD}$ type I (250 μM) was loaded in the syringe. All measurements were done at 25° C., with a stirring speed of 600 rpm and performed in 20 mM HEPES buffer (pH 7.4), 150 mM NaCl, 5% (v/v) glycerol and 0.05% (v/v) Tween-20. Binding data were analyzed using the MicroCal LLC ITC200 software.

SDS-PAGE and Native-PAGE for Western Blot

CEACAM was separated with both SDS-PAGE and native-PAGE (resp. on 15% and 7.5% polyacrylamide gels) in ice-cold 25 mM Tris, 250 mM glycine buffer. Subsequently, samples were transferred to PVDF-membranes by wet blotting at 25 V during 60 minutes in ice-cold transfer buffer (25 mM Tris, 250 mM glycine and 20% methanol). Membranes were blocked during one hour in 10% milk powder (MP), 1×PBS and 0.005% Tween-20. Both membranes were washed and incubated together in 5% MP, 1×PBS, 0.005% Tween-20 in presence of 2 μM HopQ$^{AD}$ type I for one hour to allow complex formation between HopQ$^{AD}$ I and CEACAM. After a washing step the C-terminal His-tag of HopQ (CEACAM is strep tagged) was detected by adding consecutively mouse α-His (AbD Serotec) and goat α-mouse antibody (Sigma-Aldrich) during respectively one hour and 30 minutes in 5% MP, 1×PBS, 0.005% Tween-20. After a washing step, the blot was developed by adding BCIP/NBT substrate (5-bromo-4-chloro-3-indolyl-phosphate/nitro blue tetrazolium) (Roche) in developing buffer (10 mM Tris-HCl pH 9.5, 100 mM NaCl, 50 mM MgCl2).

Bacterial Pull-Down

Bacteria were grown overnight on WCdent agar plates. Bacteria were scraped from plates, suspended in PBS, and colony forming units (cfu) were estimated by optical density 600 readings according to a standard curve. Bacteria were washed twice with PBS and $2\times10^8$ cells/ml were incubated with soluble CEACAM-Fc or CEACAM-GFP proteins or CHO cell lysates for 1 h at 37° C. with head-over-head rotation. After incubation, bacteria were washed 5 times with PBS and either boiled in SDS sample buffer (62.5 mM Tris-HCl [pH 6.8], 2% w/v SDS, 10% glycerol, 50 mM DTT, and 0.01% w/v bromophenol blue) prior to SDS-PAGE and western blotting or taken up in FACS buffer (PBS/0.5% BSA) for flow cytometry analysis.

Immunoprecipitation and Mass Spectrometry

Bacteria ($2\times10^8$) in cold PBS containing protease and phosphatase inhibitors (Roche) were lysed by ultra-sonication on ice (10×, 20 s). Cell debris was removed from the lysates by centrifugation at 15,000 rpm for 30 min at 4° C., followed by pre-clearing with prewashed protein G-agarose (Roche Diagnostics). CEACAM1-Fc was added to the lysate (10 μg) and incubated for 1 h at 4° C. Prewashed protein G-agarose (60 μL) were added to the antibody and lysate mixture and incubated 2 h at 4° C. Beads were washed with PBS for five times to remove unspecifically bound proteins. Two-thirds of the beads were separated and used for mass spectrometry sample preparation. The supernatant was removed and the beads were resuspended twice in 50 μl 7M urea/2M thiourea solved in 20 mM Hepes (pH 7.5) for denaturation of the proteins. Beads were pelleted by centrifugation and supernatants pooled and transferred to a new Eppendorf tube. Subsequently, proteins were reduced in 1 mM DTT for 45 min and alkylated at a final concentration of 5.5 mM iod acetamide for 30 min in the dark. The alkylation step was quenched by raising the DTT concentration to 5 mM for 30 min. All incubation steps were carried out at RT under vigorous shaking (Eppendorf shaker, 450 rpm). For digestion of the proteins 1 μl LysC (0.5 μg/μl) was added and the sample incubated for 4 h at RT. To reduce the urea concentration the sample was diluted 1:4 with 50 mM triethylammonium bicarbonate and then incubated with 1.5 μl trypsin (0.5 μg/μl) at 37° C. over night. Trypsin was finally inactivated by acidification with formic acid. The supernatant was transferred to a new Eppendorf tube and pooled with the following wash fraction of the beads with 0.1% formic acid. The sample was adjusted to pH 3 with formic acid (100% v/v) and subjected to peptide desalting with a SepPak C18 column (50 mg, Waters). Briefly, the column was subsequently washed with 1 ml 100% acetonitrile and 500 μl 80% acetonitrile, 0.5% formic acid. The column was equilibrated with 1 ml 0.1% TFA, the sample was loaded and the column washed again with 1 ml 0.1% TFA. After an additional wash step with 500 μl 0.5% formic acid peptides were eluted twice with 250 μl 80% acetonitrile, 0.5% formic acid. The organic phase was then removed by vacuum centrifugation and peptides stored at −80° C. Directly before measurement peptides were resolved in 20 μl 0.1% formic acid, sonificated for 5 min (water bath) and the sample afterwards filtered with a prewashed and equilibrated filter (0.45 μm low protein binding filter, VWR International, LLC). Measurements were performed on an LC-MS system consisting of an Ultimate 3000 nano HPLC directly linked to an Orbitrap XL instrument (Thermo Scientific). Samples were loaded onto a trap column (2 μm, 100 A, 2 cm length) and separated on a 15 cm C18 column (2 μm, 100 A, Thermo Scientific) during a 150 min gradient ranging from 5 to 30% acetonitrile, 0.1% formic acid. Survey spectra were acquired in the orbitrap with a resolution of 60,000 at m/z 400. For protein identification up to five of the most intense ions of the full scan were sequentially isolated and fragmented by collision induced dissociation. The received data was analyzed with the Proteome Discoverer Software version 1.4 (Thermo Scientific) and searched against the *H. pylori* (strain G27) database (1501 proteins) in the SEQUEST algorithm. Protein N-terminal acetylation and oxidation of methionins were added as variable modifications, carbamidomethylation on cysteines as static modifications. Enzyme specificity was set to trypsin and mass tolerances of the precursor and fragment ions were set to 10 ppm and 0.8 Da, respectively. Only peptides that fulfilled $X_{corr}$ values of 1.5, 2.0, 2.25 and 2.5 for charge states +1, +2, +3 and +4 respectively were considered for data analysis.

Cells, Cell-Bacteria Co-Culture and Elongation Phenotype Quantitation Assay

Gastric cancer cell lines MKN45, KatoIII (ATCC, HTB-103), MKN28 and AGS (ATCC, CRL-1739) were obtained from ATCC and DSMZ, authenticated by utilizing Short Tandem Repeat (STR) profiling, cultured either sparse or to tight confluence in DMEM (GIBCO, Invitrogen, Carlsbad Calif., USA) containing 2 mM L-glutamine (GIBCO, Invitrogen, Calif., USA) supplemented with 10% FBS (GIBCO, Invitrogen, Calif., USA) and 1% Penicillin/Streptomycin (GIBCO, Invitrogen, Calif., USA). All cell lines were maintained in an incubator at 37° C. with 5% CO2 and 100% humidity, and are routinely mycoplasma-tested twice per year by DAPI stain and PCR. Plate-grown bacteria were suspended in DMEM and washed by centrifugation at 150 g for 5 min in a microcentrifuge. After resuspension in DMEM, the optical density at 600 nm was determined and bacteria were added to the overnight serum-deprived cells at different ratios of bacteria/cell (MOI) at 37° C. to start the infection. After the indicated time, cells were washed twice with PBS and then lysed with 1% NP-40 in protease & phosphatase inhibitor PBS. HEK293 cells were chosen for CEACAM transfection studies because the cells were found to be negative for huCEACAM expression, and are easily transfectable. HEK cells were grown in 6-well plates containing RPMI 1640 medium (Invitrogen) supplemented with 25 mM HEPES buffer and 10% heat-inactivated FBS (Biochrom, Berlin, Germany) for 2 days to approximately 70% confluence. Cells were serum-deprived overnight and infected with *H. pylori* at MOI 50 for the indicated time points in each figure. After infection, the cells were harvested in ice-cold PBS containing 1 mmol/L Na3VO4 (Sigma-Aldrich). Elongated AGS cells in each experiment were quantified in 5 different 0.25-mm2 fields using an Olympus IX50 phase contrast microscope.

Transfection

A CHO cell line (ATCC) permanently expressing hu-CEACAM1-4L, mouse-CEACAM1-L and rat-CEACAM1-L were generated by stably transfecting cells with 4 μg pcDNA3.1-huCEACAM1-4L, pcDNA3.1-hu-CEAC AM1-4S, pcDNA3.1-msCEACAM1-L, pcDNA3.1-ratCEACAM1-L plasmid (Singer), respectively, utilizing the lipofectamine 2000 procedure according to the manufacturer's protocol (Invitrogen). Stable transfected cells were selected in culture medium containing 1 mg/ml of Geniticinsulfat (G418, Biochrom, Berlin, Germany). The surface expression of CEACAM1 in individual clones growing in log phase was determined by flow cytometry (FACScalibur, BD). HEK293 cells were transfected with 4 μg of the HA-tagged CEACAM constructs or luciferase reporter constructs (Clontech, Germany) for 48 h with TurboFect reagent (Fermentas, Germany) according to the manufacturer's instructions.

Western Blot

An equal volume of cell lysate was loaded on 8% SDS-PAGE gels and after electrophoresis, separated proteins were transferred to nitrocellulose membrane (Whatman/GE Healthcare, Freiburg, Germany). Membranes were blocked in 5% non-fat milk for 1 h at room temperature and incubated overnight with primary antibodies mAb 18/20 binding to CEACAM1, 3, 5, B3-17 and C5-1X (mono-specific for hu-CEACAM1, Singer), 4/3/17 (binding to CEACAM1, 5, Genovac), and 5C8C4 (mono-specific for hu-CEACAM5, Singer), 1H7-4B (mono-specific for hu-CEACAM6, Singer), 6/40c (mono-specific for hu-CEACAM8, Singer), Be9.2 (α-rat-CEACAM1), mAb 11-1H (α-rat-CEACAM1ΔN, Singer), phosphotyrosine antibody PY-99 (Santa Cruz, LaJolla, Calif., USA), α-CagA phosphotyrosine antibody PY-972, mouse monoclonal α-CagA antibody (Austral Biologicals, San Ramon, Calif., USA), mouse monoclonal α-CEACAM1 (clone D14HD11 Genovac/Aldevron, Freiburg, Germany) or goat α-GAPDH (Santa Cruz). After washing, membranes were incubated with the secondary antibody [HRP-conjugated α-mouse IgG (Promega)] and proteins were detected by ECL Western Blotting Detection reagents. The quantification was done by LabImage 1D software (INTAS).

Flow Cytometry

The Fc-tagged CEACAMs (2.5 μg/ml) were incubated with *H. pylori* (OD:1) and subsequently with FITC-conjugated goat α-human IgG (Sigma). After washing with FACS buffer, the samples were analyzed by gating on the bacteria (based on forward and sideward scatter) and measuring bacteria-associated fluorescence. In each case, 10,000 events per sample were obtained. Analysis was performed with the FACS CyAn (Beckman Coulter) and the data were evaluated with FlowJo software (Treestar). For the analysis of CEACAM-mediated HopQ binding, indicated cell types ($5\times10^5$ in 50 μl) were incubated with 20 μg/ml of *H. pylori* strain P12 derived, myc and 6x His-tagged recombinant HopQ diluted in 3% FCS/PBS for 1 h on ice. After three times washing with 3% FCS/PBS samples were labeled with 20 μg/ml of mouse α-c-myc mAb (clone 9E10, AbD Serotec) and subsequently with FITC conjugated goat α-mouse F(ab')2 (Dianova, Germany). In parallel, the presence of CEACAMs was controlled by staining cells utilizing the rabbit anti CEA pAb (A0115, Dianova) followed by FITC conjugated goat α-rabbit F(ab')2 (Dianova, Germany).

Background fluorescence was determined using isotype-matched Ig mAb. The stained cell samples were examined in a FACScalibur flow cytometer (BD Biosciences, San Diego, Calif.) and the data were analyzed utilizing the CellQuest software. Dead cells, identified by PI staining, were excluded from the measurement.

Immunohistochemistry

Following approval of the local ethics committee, paraffin-embedded human normal stomach, gastritis and cancer samples were randomly chosen from the tissue bank of the Institut für Pathologic, Klinikum Bayreuth, Germany. Histological samples were excluded if tissue quality was poor. After antigen retrieval with 10 mmol/L sodium citrate buffer pH 6 in pressure cooker, the sections were incubated with α-hu-CEACAM1, 5, 6 and α-rat-CEACAM1 antibodies (clone B3-17, 5C8C4, 1H7-4B and Be9.2, respectively). Sections were developed with SignalStain DAB (Cell Signaling) following manufacturer's instructions. Sections were counterstained with hematoxylin (Morphisto). The automated image acquisition was performed with Olympus Virtual Slide System VS120 (Olympus, Hamburg, Germany).

Adherence Assay

The adherence assay was performed according to Hytonen et al., 2006. Briefly, human gastric epithelial cells (MKN45 and AGS) and CEACAM1-transfected CHO cells were grown in antibiotic free DMEM (Gibco, Gaithersburg, Md.) supplemented with 5% FCS and 1-glutamine (2 mmol, Sigma, St. Louis, USA) on tissue culture 96 well plates (Bioscience) in 5% CO2 atmosphere for 2 days. To visualize *H. pylori* cells in adhesion assays, OD: 1 of bacteria were fluorescence labeled with CFDA-SE (Molecular Probes) and washed with PBS. CFDA-SE was added at concentration of 10 μmol/L for 30 min at 37° C. under constant rotation in the dark. Excess dye was removed by 3 times PBS washing. Bacteria were resuspended in PBS until further use. Labelled bacteria were co-incubated (MOI 10) with the cells at 37° C. with gentle agitation for 1 h. After washing with PBS (1 ml, ×3) to remove non-adherent bacteria, cells were fixed in paraformaldehyde (2%, 10 min). Bacterial binding was determined by measuring the percentage of cells that bound fluorescent-labeled bacteria using flow cytometry analysis.

IL-8 Cytokine ELISA

AGS cell line was infected with *H. pylori* as described above and PBS-incubated control cells served as negative control. The culture supernatants were collected and stored at −20° C. until assayed. IL-8 concentration in the supernatant was determined by standard ELISA with commercially available assay kits (Becton Dickinson, Germany) according to described procedures.

HopQ-Dependency of CagA Virulence Pathways

If not indicated otherwise, the AGS cell line (ATCC CRL-1730) was infected with the various *H. pylori* strains for 6 hours at a multiplicity of infection (MOI) of 50. The cells were then harvested in ice-cold PBS in the presence of 1 mmol/L Na3VO4 (Sigma-Aldrich). In each experiment the number of elongated AGS cells was quantified in 10 different 0.25-mm2 fields using a phase contrast microscope (Olympus IX50). CagA translocation was determined using the indicated antibodies detecting Tyr-phosphorylated CagA. All experiments were performed in triplicates. For inhibition experiments, cells were incubated with the indicated antibodies or peptides prior to infection.

Confocal Microscopy

CHO cells were grown on chamber slides (Thermo Scientific), fixed in paraformaldehyde (4%, 10 min) and blocked with PBS/5% bovine serum albumin. CFDA-SE labelled bacteria (10 μmol/L for 30 min at 37° C. under constant rotation in the dark) at MOI 5 were incubated with cells for 1 h at 37° C. under constant rotation. After 5× PBS washing, cell membranes were stained with Deep Red (Life Technology) and cell nuclei with DAPI (Life Technology). Confocal images of cells were taken using a Leica SP5 confocal microscope.

Crystallization and Structure Determination of $HopQ^{AD}$ and of a Complex of $HopQ^{AD}$ and C1ND $HopQ^{AD}$ was concentrated to 40 mg/mL and crystallized by sitting drop vapor diffusion at 20° C. using 0.12 M alcohols (0.02 M 1,6-Hexanediol; 0.02 M 1-Butanol; 0.02 M 1,2-Propanediol; 0.02 M 2-Propanol; 0.02 M 1,4-Butanediol; 0.02 M 1,3-Propanediol), 0.1 M Tris (base)/BICINE pH 8.5, 20% v/v PEG 500* MME; 10% w/v PEG 20000 as a crystallization buffer. Crystals were loop-mounted and flash-cooled in liquid nitrogen. Data were collected at 100 K at beamline Proximal (SOLEIL, Gif-sur-Yvette, France) and were indexed, processed and scaled using the XDS package. All crystals were in the $P2_1$ space group with approximate unit cell dimensions of a=57.7 Å, b=57.7 Å, c=285.7 Å and beta=90.1° and four copies of $HopQ^{AD}$ per assymetric unit. Phases were obtained by molecular replacement using the BabA structure, and the model was refined by iterative cycles of manual rebuilding and maximum likelihood refinement using Refmac5. Table 1 summarizes the crystal parameters, data processing and structure refinement statistics. To form a complex between $HopQ^{AD}$ and the N-domain of human CEACAM1 (C1ND), purified recombinant C1ND was added in a 1.2-fold molar excess relative to purified $HopQ^{AD}$, and the mixture was injected onto an Hi-Prep™ 26/60 Sephacryl S-100 HR column (GE Healthcare) pre-equilibrated in 20 mM Tris-HCl pH 8.0, 500 mM NaCl buffer. Fractions containing the $HopQ^{AD}$-C1ND complex were pooled together and concentrated to a final concentration of 30 mg/mL using a 30 kDa MW cutoff spin concentrator. Crystals were obtained in 0.03 M sodium fluoride, 0.03 M sodium bromide, 0.03 M sodium iodide, 0.1 M MES pH 6.5, 20% v/v Ethylene glycol and 10% w/v PEG 8000. Crystals were loop-mounted and flash-cooled in liquid nitrogen, and data were collected at 100 K at beamline Proxima 1 (Soleil, Gif-sur-Yvette, France). Crystals were in the C2 space group with approximate unit cell dimensions of a=118.0 Å, b=174.0 Å, c=118.1 Å, beta=118.4 and three copies of $HopQ^{AD}$-C1ND per assymetric unit. Phases were obtained by molecular replacement using the $HopQ^{AD}$ and C1ND (PDB code 4WHD) structures, and the model was refined by iterative cycles of manual rebuilding and maximum likelihood refinement using Refmac5. Table 2 summarizes the crystal parameters, data processing and structure refinement statistics.

Amino Acid Sequence Alignment

The amino acid sequence alignment of the N-terminal domains of human, mouse and rat-CEACAM1 and human CEACAMs (1, 5, 6 and 8) was performed using CLC main Workbench (CLC bio).

Luciferase Reporter Assays

CHO-CEACAM1-L cells transfected with various luciferase reporter and control constructs (Clontech) were infected with *H. pylori* for 5 h and analyzed by luciferase assay using the Dual-Luciferase Reporter Assay System according to the manufactures instruction (Promega, USA). Briefly, cells were harvested by passive lysis, the protein concentration was measured with Precision Red (Cytoskeleton, USA) and the lysates were equalized by adding passive lysis buffer.

The luciferase activity was measured by using a Plate Luminometer (MITHRAS LB940 from Berthold, Germany).

Animal Experiments

Specific pathogen free, 120-150 gr male Sprague dawley rats, 4 weeks old, were obtained from Charles River Laboratories, Sulzfeld, Germany. Animals were randomly distributed into the different experimental groups by animal care takers not involved in the experiments, and criteria for the exclusion of animals were pre-established. Investigator blinding was performed for all assessment of outcome and data, histology was performed by an independent investigator in a blinded manner. Animals were challenged twice intragastrically in groups of 8 with ~$1\times10^9$ live *H. pylori* in 2 interval days. The experiments were performed in the specific pathogen-free unit of Zentrum für Präklinische Forschung Klinikum r. d. Isar der TU München, according to the allowance and guidelines of the ethical committee and state veterinary office (Regierung von Oberbayern, 55.2-1.54-2532-160-12).

Statistical Analysis

For in vitro experiments, normal distribution was determined by Shapiro-Wilk test. All data were analyzed with two-tailed Student t-test and one-way ANOVA with post hoc Bonferroni test (comparing more than two groups) using Graph Pad Prism Software. Data are shown as means±s.e.m or s.d. for at least three independent experiments. P values<0.05 were considered significant. For animal studies, power calculation was performed based on previous animal experiments to achieve two sided significance of 0.05 while using lowest possible numbers to comply with the ethical guidelines for experimental animals.

REFERENCES

1. Apostolopoulos, V. et al., 2013. Targeting antigens to dendritic cell receptors for vaccine development. Journal of Drug Delivery, 2013:869718.
2. Belogolova, E. et al., 2013. *Helicobacter pylori* outer membrane protein HopQ identified as a novel T4SS-associated virulence factor. Cell Microbiol. 15, pp. 1896-1912.
3. Blaser, M. J. et al., 1995. Infection with *Helicobacter pylori* strains possessing cagA is associated with an increased risk of developing adenocarcinoma of the stomach. Cancer Research, 55(10), pp. 2111-2115.
4. Cao, P. & Cover, T. L., 2002. Two different families of hopQ alleles in *Helicobacter pylori*. Journal of Clinical Microbiology, 40, pp. 4504-4511.
5. Forman, D., 1996. *Helicobacter pylori* and gastric cancer. Scandinavian Journal of Gastroenterology. Supplement, 214, pp. 31-3-discussion 40-3.
6. Fox, J. G., 2002. The non-*Helicobacter pylori* helicobacters: their expanding role in gastrointestinal and systemic diseases. Gut, 50, pp. 273-283.
7. Fox, J. G. et al., 1998. Hepatic *Helicobacter* species identified in bile and gallbladder tissue from Chileans with chronic cholecystitis. Gastroenterology, 114, pp. 755-763.
8. Gao, W. et al., 2010. The evolution of *Helicobacter pylori* antibiotics resistance over 10 years in Beijing, China. *Helicobacter,* 15(5), pp. 460-466.
9. Gómez-Gascón, L. et al., 2012. Exploring the pansurfome of *Streptococcus suis*: looking for common protein antigens. Journal of Proteomics, 75(18), pp. 5654-5666.
10. Graham, D. Y. & Shiotani, A., 2005. The time to eradicate gastric cancer is now. Gut, 54(6), pp. 735-738.
11. Hytonen, J. et al., 2006. Use of flow cytometry for the adhesion analysis of *Streptococcus pyogenes* mutant strains to epithelial cells: investigation of the possible role of surface pullulanase and cysteine protease, and the transcriptional regulator Rgg. BMC Microbiol., 6, 18, doi:10.1186/1471-2180-6-18.
12. Jemal, A. et al., 2011. Global cancer statistics. CA: a cancer journal for clinicians, 61(2), pp. 69-90.
13. Kalali, B. et al., 2014. *H. pylori* virulence factors: influence on immune system and pathology. Mediators of Inflammation, 2014:426309.
14. Koebnik, R. et al., 2000. Structure and function of bacterial outer membrane proteins: barrels in a nutshell. Molecular Microbiology, 37(2), pp. 239-253.
15. Matsukura, N. et al., 2002. Association between *Helicobacter bilis* in bile and biliary tract malignancies: *H. bilis* in bile from Japanese and Thai patients with benign and malignant diseases in the biliary tract. Jpn J Cancer Res., 93(7), pp. 842-7.
16. Mori, J. et al., 2012. Chimeric flagellin as the self-adjucanting antigen for the activation of immune response against *Helicobacter pylori*. Vaccine, 30(40), pp. 5856-5863.
17. Nomura, A. et al., 1994. *Helicobacter pylori* infection and the risk for duodenal and gastric ulceration. Annals of Internal Medicine, 120(12), pp. 977-981.
18. Parsonnet, J. et al., 1991. *Helicobacter pylori* infection and the risk of gastric carcinoma. New England Journal of Medicine, 325(16), pp. 1127-1131.
19. Perez-Perez, G. I. et al., 2004. Epidemiology of *Helicobacter pylori* infection. *Helicobacter,* 9 Suppl 1, pp. 1-6.
20. Pisani, P. et al., 2008. Cross-Reactivity between Immune Responses to *Helicobacter bilis* and *Helicobacter pylori* in a Population in Thailand at High Risk of Developing Cholangiocarcinoma. Clin Vaccine Immunol., 15(9), pp. 1363-1368.
21. Shiota, S. et al., 2010. Population-based strategies for *Helicobacter pylori*-associated disease management: a Japanese perspective. Expert Review of Gastroenterology & Hepatology, 4(2), pp. 149-156.
22. Singer, B. B. et al., 2014. Soluble CEACAM8 interacts with CEACAM1 inhibiting TLR2-triggered immune responses. PLoS One, 9, e94106.
23. Sioud, M. et al., 2013. A novel peptide carrier for efficient targeting of antigens and nucleic acids to dendritic cells. FASEB J., 27(8), pp. 3272-3283.
24. Song, H. et al., 2015. A novel chimeric flagellum fused with the multi-epitope vaccine CTB-UE prevents *Helicobacter pylori*-induced gastric cancer in a BALB/c mouse model. Appl Microbiol Biotechnol., 99(22), pp. 9495-9502.
25. Tchoupa, A. K. et al., 2014. Signaling by epithelial members of the CEACAM family—mucosal docking sites for pathogenic bacteria. Cell Commun Signal, 12:27.
26. United States Centers for Disease Control and Prevention (2011). "A CDC framework for preventing infectious diseases", accessed 20 Dec. 2012.

The invention claimed is:

1. A method of treating a disease or disorder caused by or associated with *H. pylori*, the method comprising the step of administering an inhibitor of an interaction between *Helicobacter pylori* HopQ and a member of the carcinoembryonic antigen-related cell adhesion molecule (CEACAM) family,
   wherein the inhibitor is selected from the group consisting of
   (a) (poly-)peptide ligands binding to an extracellular domain of *H. pylori* HopQ; and
   (b) nucleic acid molecules encoding the (poly-)peptide ligands of (a);
   wherein the extracellular domain of *H. pylori* HopQ is the insertion domain, loop A, loop B, loop C or loop D of *H. pylori* HopQ, wherein
   loop A is located between helix H3 and strand S1 of *H. pylori* HopQ;
   loop B is located between strand S2 and helix H4 of *H. pylori* HopQ;
   loop C is located between helix H5 and helix H6 of *H. pylori* HopQ; and
   loop D is located between helix H7 and helix H8 of *H. pylori* HopQ,
   wherein the inhibitor inhibits binding of *H. pylori* HopQ to an extracellular domain of the member of the CEACAM family, and/or
   wherein the inhibitor inhibits binding to the N-domain of the member of the CEACAM family.

2. The method of claim 1, wherein the inhibitor inhibits binding of *H. pylori* HopQ to the member of the CEACAM family and/or HopQ-CEACAM-mediated signaling.

3. The method of claim 1, wherein the member of the CEACAM family is selected from the group consisting of human CEACAM family members, non-human primate CEACAM family members and rat CEACAM family members.

4. The method of claim 1, wherein the disease or disorder caused by or associated with *H. pylori* is selected from the group consisting of *H. pylori* infection and gastroduodenal disorders caused by *H. pylori*.

5. The method of claim 1, wherein the member of the CEACAM family is selected from the group consisting of CEACAM1, CEACAM3, CEACAM5 and CEACAM6.

6. The method of claim 4, wherein the gastroduodenal disorders caused by *H. pylori* are selected from the group consisting of gastritis, chronic gastritis, gastric atrophy, gastric or duodenal ulcer, stomach cancer and MALT lymphoma.

* * * * *